(12) United States Patent
Carroll et al.

(10) Patent No.: US 8,158,663 B2
(45) Date of Patent: Apr. 17, 2012

(54) COMPOUNDS AS CANNABINOID RECEPTOR LIGANDS AND USES THEREOF

(75) Inventors: William A. Carroll, Evanston, IL (US); Michael J. Dart, Highland Park, IL (US); Tongmei Li, Lake Bluff, IL (US); Arturo Perez-Medrano, Grayslake, IL (US); Sridhar Peddi, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 1160 days.

(21) Appl. No.: 11/954,956

(22) Filed: Dec. 12, 2007

(65) Prior Publication Data
US 2008/0153883 A1    Jun. 26, 2008

Related U.S. Application Data

(60) Provisional application No. 60/876,604, filed on Dec. 22, 2006.

(51) Int. Cl.
*A61K 31/426* (2006.01)
*C07D 277/38* (2006.01)
(52) U.S. Cl. ........................ 514/371; 548/195
(58) Field of Classification Search .................. 548/195; 514/371
See application file for complete search history.

(56) References Cited

FOREIGN PATENT DOCUMENTS

| | | |
|---|---|---|
| CA | 2587667AA | 5/2006 |
| EP | 1219612 A1 | 7/2002 |
| WO | WO-03097605 A1 | 11/2003 |
| WO | WO-2005058887 A1 | 6/2005 |
| WO | WO-2007140385 A2 | 12/2007 |
| WO | WO-2007140439 A2 | 12/2007 |

OTHER PUBLICATIONS

Andreani et al., "Ring-opened, etc.," Collect. Czech. Chem. Commun., 64, 1999, pp. 299-312.*
Viallet et al., "2-Aminothiazoline, etc.," CA 93:8074 (1980).*
"IUPAC Commission on Nomenclature of Organic Chemistry Rules for the Nomenclature of Organic Chemistry, Section E: Stereochemistry (Recommendations 1974)," Pure Appl Chem, 1976, 13-30, vol. 45.
Ansell M.F. and Mason J.S., "The Synthesis of (+/−)-10a-Homo-11a-carbathromboxaneA1, a Stable Thromboxane A Analogue," J Chem Soc Perkin Trans I, 1984, 1061-1068.
Arevalo-Martin, A., et al., "Therapeutic Action of Cannabinoids in a Murine Model of Multiple Sclerosis," Journal of Neuroscience, 2003, 2511-2516, vol. 23, No. 7.
Benito, C, et al., "A Glial Endogenous Cannabinoid System Is Upregulated in the Brains of Macaques with Simian Immunodeficiency Virus-Induced Encephalitis," Journal of Neuroscience, 2005, 2530-2536, vol. 25-Issue 10.
Benito, C. et al., "Cannabinoid CB2 Receptors and Fatty Acid Amide Hydrolase Are Selectively Overexpressed in Neuritic Plaque-Associated Glia in Alzheimer's Disease Brains," Journal of Neuroscience, 2003, 11136-11141, vol. 23-Issue 35.
Berge, S.M. et al., "Journal of Pharmaceutical Sciences, Pharmaceutical Salts," J Pharmaceutical Sciences, 1977, 1-19, vol. 66.
Bouchard, J-F et al., "Contribution of endocannabinoids in the endothelial protection afforded by ischemic preconditioning in the isolated rat heart", Life Sciences, 2003, 1859-1870, vol. 72.
Boyle, W.J. et al., "Osteoclast differentiation and activation," (Binary/Image), 2003, 337-342, vol. 423.
Brennan, T.J. et al., "Characterization of a rat model of incisional pain," (Binary/Image), 1996, 493-501, vol. 64.
Bruson H.A. and Eastes J.W., "Action of Sulfuric Acid upon Unsaturated Isothiocyanates: Mercaptothiazolines," J. Am. Chem. Soc, 1937, 2011-2013, vol. 59-Issue 10.
Buckley, N.E. et al., "Immunomodulation by cannabinoids is absent in mice deficient for the cannabinoid CB receptor," European Journal of Pharmacology, 2000, 141-149, vol. 396.
Carrier, E.J. et al., "Endocannabinoids in Neuroimmunology and Stress," Current Drug Targets CNS and Neurological Disorders, 2005, 657-665, vol. 4.
Casanova, M.L. et al., "Inhibition of skin tumor growth and angiogenesis in vivo by activation of cannabinoid receptors," Journal of Clinical Investigation, 2003, 43-50, vol. 111.
Chaplan, S.R. et al., "Quantitative assessment of tactile allodynia in the rat paw," Journal of Neuroscience Methods, 1994, 55-63, vol. 53.
Cichewicz, D.L. et al., "Synergistic interactions between cannabinoid and opioid analgesics," Life Sciences, 2004, 1317-1324, vol. 74.
Clayton, N. et al., "CB1 and CB2 cannabinoid receptors are implicated in inflammatory pain," (Binary/Image), 2002, 253-260, vol. 96.
Dixon, W.J. "Efficient analysis of experimental observations," Annual Review of Pharmacology and Toxicology, 1980, 441-462, vol. 20.
Filippo, C.D. et al., "Cannabinoid CB2 receptor activation reduces mouse myocardial ischemia-reperfusion injury: involvement of cytokine/chemokines and PMN," Journal of Leukocyte Biology, 2004, 453-459, vol. 75.
Galiégue, et al., "Expression of central and peripheral cannabinoid receptors in human immune tissues and leukocyte subpopulations," European Journal of Biochemistry, 1995, 54-61, vol. 232.
Golech, S.A. et al., "Human brain endothelium: coexpression and function of vannilloid and endocannabinoid receptors," Molecular Brain Research, 2004, 87-92, vol. 132.
Greene, T.W. et al., "Protective Groups in Organic Synthesis", 1999, 3 rd Ed, 494-653.
Grotenhermen, F. et al., "IACM 2nd Conference on Cannabinoids in Medicine," Expert Opinion in Pharmacotherapy, 2003, 2367-2371, vol. 4-Issue 12.

(Continued)

*Primary Examiner* — Patricia Morris
(74) *Attorney, Agent, or Firm* — Nancy J. Gettel; Sonali Srivastava

(57) ABSTRACT

The present invention relates to thiazolidinylidene containing compounds of formula (I)

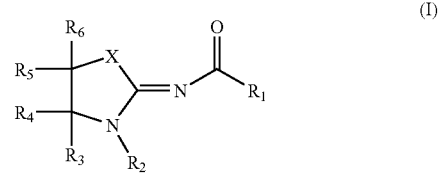

wherein $R_1$, $R_2$, $R_3$, $R_4$, $R_5$, $R_6$, and X are as defined in the specification, compositions comprising such compounds, and methods of treating conditions and disorders using such compounds and compositions.

7 Claims, No Drawings

OTHER PUBLICATIONS

Hanus, L. et al., "HU-308: A specific agonist for CB 2, a peripheral cannabinoid receptor," Proceedings of the National Academy of Science, 1999, 14228-14233, vol. 96.

Hohmann, A.G. et al., "Selective Activation of Cannabinoid CB2 Receptors Suppresses Hyperalgesia Evoked by Intradermal Capsaicin," Journal of Pharmacology and Experimental Therapeutics, 2004, 446-453, vol. 308.

Ibrahim, M.M. et al., "Activation of CB2 cannabinoid receptors by AM1241 inhibits experimental neuropathic pain: Pain inhibition by receptors not present in the CNS," Proceedings of the National Academy of Science, 2003, 10529-10533, vol. 100-Issue 18.

Ibrahim, M.M. et al., "CB2 cannabinoid receptor activation produces antinociception by stimulating peripheral release of endogenous opioids," Proceedings of the National Academy of Science, 2005, 3093-3098, vol. 102-Issue 8.

Idris, A.I. et al., "Regulation of bone mass, bone loss and osteoclast activity by cannabinoid receptors," Nature Medicine, 2005, 774-779, vol. 11-Issue 7.

Ihenetu, K. et al., "Inhibition of interleukin-8 release in the human colonic epithelial cell line HT-29 by cannabinoids," European Journal of Pharmacology, 2003, 207-215, vol. 458.

International Search Report for application No. PCT/US2007/0087175, Mailed on Aug. 4, 2008, 4 pages.

Julien, B, et al., "Antifibrogenic Role of the Cannabinoid Receptor CB2 in the Liver," Gastroenterology, 2005, 742-755, vol. 128.

Karsak, M, et al., "Cannabinoid receptor type 2 gene is associated with human osteoporosis," Human Molecular Genetics, 2005, 3389-3396, vol. 14-Issue 22.

Kim, S.H. and Chung, J.M. "An experimental model for peripheral neuropathy produced by segmental spinal nerve ligation in the rat," (Binary/Image), 1992, 355-363, vol. 50-Issue 3.

Kreutzberg, G W "Microglia: a sensor for pathological events in the CNS," Trends in Neuroscience, 1996, 312-318, vol. 19.

Lepicier, P. et al., "Endocannabinoids protect the rat isolated heart against ischaemia," British Journal of Pharmacology, 2003, 805-815, vol. 139.

Lotersztajn, S. et al., "Hepatic Fibrosis: Molecular Mechanisms and Drug Targets," Annual Review of Pharmacology and Toxicology, 2005, 605-628, vol. 45.

Malan, T.P. et al., "CB2 cannabinoid receptor-mediated peripheral antinociception," (Binary/Image), 2001, 239-245, vol. 93.

Maresz, K, et al., "Modulation of the cannabinoid CB2 receptor in microglial cells in response to inflammatory stimuli," Journal of Neurochemistry, 2005, 437-445, vol. 95.

Mathison, R, et al., "Effects of cannabinoid receptor-2 activation on accelerated gastrointestinal transit in lipopolysaccharide-treated rats," British Journal of Pharmacology, 2004, 1247-1254, vol. 142.

McKallip, R.J. et al., "Targeting CB2 cannabinoid receptors as a novel therapy to treat malignant lymphoblastic disease," (Binary/Image), 2002, 637-634, vol. 100.

Molina-Holgado, F. et al., "Endogenous Interleukin-1 Receptor Antagonist Mediates Anti-Inflammatory and Neuroprotective Actions of Cannabinoids in Neurons and Glia," Journal of Neuroscience, 2003, 6470-6474, vol. 23-Issue 16.

Nackley, A.G. et al., "Selective activation of cannabinoid CB2 receptors suppresses spinal fos protein expression and pain behavior in a rat model of inflammation," Neuroscience, 2003, 747-757, vol. 119.

Ni, X. et al., "Win 55212-2, a cannabinoid receptor agonist, attenuates leukocyte/endothelial interactions in an experimental autoimmune encephalomyelitis model," Multiple Sclerosis, 2004, 158-164, vol. 10.

Nunez, E. et al., "Cannabinoid CB2 Receptors Are Expressed by Perivascular Microglial Cells in the Human Brain: An Immunohistochemical Study," Synapse, 2004, 208-213, vol. 53.

Partch, Ret al., "2-Oxaadamantane-1-N,N,N-trimethylmethanaminium Iodide:1 Synthesis and Potential for Muscarinic Activity," Croatia Chemical Acta, 1985, 661-669, vol. 58-Issue 4.

Patel, J.J. et al., "Inhibition of guinea-pig and human sensory nerve activity and the cough reflex in guinea-pigs by cannabinoid (CB2) receptor activation," British Journal of Pharmacology, 2003, 261-268, vol. 140.

Pertwee, R.G. "Cannabinoids and multiple sclerosis," Pharmacology and Therapeutics, 2002, 165-174, vol. 95.

Prescott, et al., "Lipid Vesicles as Carriers for Introducing Biologically Active Materials into Cells," Methods in Cell Biology, 1976, 33-71, vol. 14, Academic Press.

Quartilho, A. et al., "Inhibition of Inflammatory Hyperalgesia by Activation of Peripheral CB2 Cannabinoid Receptors," Anesthesiology, 2003, 955-960, vol. 99.

Ralston, S.H. "Genetic determinants of susceptibility to osteoporosis," Current Opinion in Pharmacology, 2003, 286-290, vol. 3.

Ramirez, B.G. et al., "Prevention of Alzheimer's Disease Pathology by Cannabinoids: Neuroprotection Mediated by Blockade of Microglial Activation," Journal of Neuroscience, 2005, 1904-1913, vol. 25-Issue 8.

Sanchez C. et al., "Inhibition of Glioma Growth in Vivo by Selective Activation of the CB2 Cannabinoid Receptor1," Cancer Research, 2001, 5784-5789, vol. 61.

Steffens S. et al., "Low dose oral cannabinoid therapy reduces progression of atherosclerosis in mice," (Binary/Image), 2005, 782-786, vol. 434.

Valenzano K.J. et al., "Pharmacological and pharmacokinetic characterization of the cannabinoid receptor 2 agonist, GW405833, utilizing rodent models of acute and chronic pain, anxiety, ataxia and catalepsy," Neuropharmacology, 2005, 658-672, vol. 48.

Walter L. et al., "Cannabinoids and neuroinflammation," Pharmacology, 2004, 775-785, vol. 141.

Warhurst A.C. et al., "Interferon ? induces differential upregulation of a and β chemokine secretion in colonic epithelial cell lines," (Binary/Image), 1998, 208-213, vol. 42.

Watkins L.R. et al, "Glial activation: a driving force for pathological pain," Trends in Neuroscience, 2001, 450-455, vol. 24-Issue 8.

Weyer et al., "Blutzuckersenkende Chinolin-8-carboxamidoalkyl-benzol sulfonamid derivate", Arzneimittel-Forschung, 1974, vol. 24, 269-275.

Williams K. et al., "Central nervous system perivascular cells are immunoregulatory cells that connect the CNS with the peripheral immune system," (Binary/Image), 2001, 156-164, vol. 36.

Wright K. et al., "Differential Expression of Cannabinoid Receptors in the Human Colon: Cannabinoids Promote Epithelial Wound Healing," Gastroenterology, 2005, 437-453, vol. 129.

Yoshihara S. et al., "Cannabinoid Receptor Agonists Inhibit Sensory Nerve Activation in Guinea Pig Airways", American Journal of Respiratory and Critical Care Medicine, 2004, 941-946, vol. 170.

Yoshihara S. et al., "Endogenous Cannabinoid Receptor Agonists Inhibit Neurogenic Inflammations in Guinea Pig Airways" Allergy and Immunology, 2005, 80-87, vol. 138.

Yoshihara S. et al., "The Cannabinoid Receptor Agonist WIN 55212-2 Inhibits Neurogenic Inflammations in Airway Tissues," Journal of Pharmacological Sciences, 2005, 77-82, vol. 98-Issue 1.

Zimmer, A et al., "Increased mortality, hypoactivity, and hypoalgesia in cannabinoid CB1 receptor knockout mice," Proceedings of the National Academy of Science, 1999, 5780-5785, vol. 96.

Joshi, et al., "Comparison of Antinociceptive Actoins of Standard Analgesics in Attenuating Capsaicin and Nerve-Injury-Induced Mechanical Hypersensitivity," Neuroscience, 2006, vol. 143, pp. 587-596.

Meyers, et al., "Oxazolines. XX. Synthesis of Achiral and Chiral Thiiranes and Olefins by Reaction of Carbonyl Compounds with 2-(Alkylthio)-2-oxazolines," Journal of Organic Chemistry, 1976, vol. 41 (10), pp. 1735-1742.

* cited by examiner

COMPOUNDS AS CANNABINOID RECEPTOR LIGANDS AND USES THEREOF

This application claims priority to U.S. patent application Ser. No. 60/876,604, filed Dec. 22, 2006 and is incorporated herein by reference.

TECHNICAL FIELD

The present invention relates to thiazolidinylidene containing compounds, compositions comprising such compounds, and methods of treating conditions and disorders using such compounds and compositions.

BACKGROUND OF THE INVENTION (−)-$\Delta^9$-Tetrahydrocannabinol ($\Delta^9$-THC), the major psychoactive constituent of marijuana, exerts a broad range of biological effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in preclinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic).

Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-op pain) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds of the present invention are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties. Therefore, compounds that interact with $CB_2$ receptors offer a unique pharmacotherapy for the treatment of immune and inflammatory disorders.

Accordingly, the need exists to further explore and develop $CB_2$ receptor ligands that exhibit immunomodulatory and anti-inflammatory properties. These $CB_2$ receptors ligands will offer a unique pharmacotherapy for the treatment of immune and inflammatory disorders.

SUMMARY

The present invention generally provides thiazolidinylidene containing compounds and pharmaceutical compositions and methods for the treatment of disorders using these compounds and pharmaceutical compositions.

In one embodiment, the present invention provides compounds of formula (I), or a pharmaceutically acceptable salt or prodrug thereof,

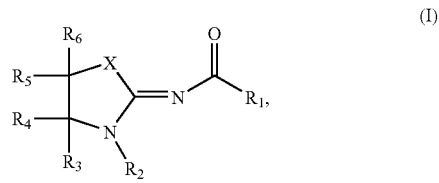

wherein

X is S or O;

$R_1$ is (a) phenyl substituted with 1, 2, 3, 4, or 5 substituents as represented by $R_j$, (b) naphthyl, cycloalkyl, heterocycle, or (c) formula (i), (ii), (iii), or (iv)

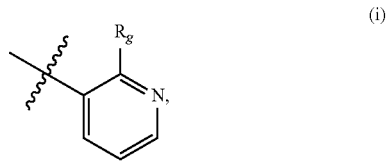

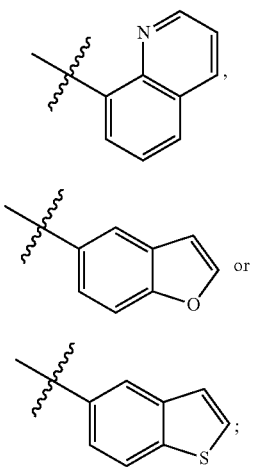

wherein each of the naphthyl, cycloalkyl, heterocycle or formula (i), (ii), (iii), or (iv) is optionally further substituted with 1, 2, or 3 substituents as represented by $R_j$;

$R_j$ and $R_g$, at each occurrence, are each independently alkenyl, alkoxy, alkoxyalkoxy, alkoxyalkoxyalkyl, alkoxyalkyl, alkoxycarbonyl, alkoxycarbonylalkyl, alkyl, alkylcarbonyl, alkylcarbonylalkyl, alkylcarbonyloxy, alkylsulfinyl, alkylsulfinylalkyl, alkyl-S(O)$_2$—, alkyl-S(O)$_2$-alkyl-, cyanoalkyl, formyl, =N—O(alkyl), =N—OH, alkylthio, alkylthioalkyl, alkynyl, carboxy, carboxyalkyl, cyano, halogen, haloalkyl, haloalkoxy, hydroxy, hydroxyalkyl, nitro, $R_hR_k$—N—, ($R_mR_n$N)carbonyl, cycloalkyloxy, heterocycleoxy, cycloalkylalkoxy, cycloalkyl, or morpholinyl;

$R_2$ is alkyl, alkoxy-($C_2$-$C_6$ alkylene)-, alkoxyalkoxy-($C_2$-$C_6$ alkylene)-, alkenyl, alkynyl, arylalkyl, cycloalkylalkyl, cycloalkyloxyalkyl, cycloalkylalkoxyalkyl, cyanoalkyl, nitroalkyl, haloalkyl, haloalkoxyalkyl, heteroarylalkyl, heterocyclealkyl, heterocycleoxyalkyl, hydroxyalkyl, $R_aR_bN$—($C_2$-$C_6$ alkylene)-, $R_cS$—($C_2$-$C_6$ alkylene)-, $R_c$—SO$_2$-alkylene-, $R_c$, —C(O)-alkylene-, $R_dC$(=N—OR$_f$)—($C_2$-$C_6$ alkylene)-, $R_dR_eN$—SO$_2$-alkylene-, or $R_dR_eN$—C(O)-alkylene-;

$R_3$ and $R_4$ are each independently hydrogen, alkyl, cycloalkyl, haloalkyl, heterocycle, or hydroxyalkyl or $R_3$ and $R_4$ taken together with the carbon atom to which they are attached form a monocyclic cycloalkyl or a monocyclic heterocyclic ring wherein the monocyclic heterocycle ring contains at least one oxygen;

$R_5$ and $R_6$ are each independently hydrogen, alkyl, aryl, cycloalkyl, haloalkyl, heteroaryl, heterocycle, or hydroxyalkyl; or $R_5$ and $R_6$ taken together with the carbon atom to which they are attached form a monocyclic cycloalkyl ring or a monocyclic heterocyclic ring; or $R_3$ and $R_5$ taken together with the atoms to which they are attached form a monocyclic cycloalkyl or a monocyclic heterocyclic ring provided that the monocyclic heterocyclic ring is saturated and contains at least one oxygen;

$R_a$ and $R_b$, at each occurrence, are each independently hydrogen, alkyl, haloalkyl, alkylcarbonyl, alkylsulfonyl, aryl, arylcarbonyl, arylsulfonyl, or cycloalkyl;

$R_c$, at each occurrence, is independently alkyl, haloalkyl, aryl, or arylalkyl;

$R_d$ and $R_e$, at each occurrence, are each independently hydrogen, alkyl, haloalkyl, aryl, or arylalkyl;

$R_f$ is hydrogen, alkyl, or haloalkyl;

$R_h$ and $R_k$, at each occurrence, are each independently hydrogen, alkyl, haloalkyl, alkylcarbonyl, alkylsulfonyl, aryl, arylcarbonyl, arylsulfonyl, or cycloalkyl; and $R_m$ and $R_n$, at each occurrence, are each independently hydrogen, alkyl, haloalkyl, aryl, or arylalkyl.

In another embodiment, the present invention provides a method for treating pain (for example, neuropathic pain or nociceptive pain) in a mammal in need of such treatment. The method comprises administering to the mammal a therapeutically effective amount of a compound of formula (I) or a pharmaceutically acceptable salt thereof.

In yet another embodiment, the present invention provides a method for treating a disorder selected from the group consisting of inflammatory disorders, immune disorders, neurological disorders, cancers of the immune system, respiratory disorders, and cardiovascular disorders in a mammal in need of such treatment. The method comprises administering to the mammal a therapeutically effective amount of a compound of formula (I) or a pharmaceutically acceptable salt thereof.

Another embodiment of the present invention relates to a method for providing neuroprotection in a mammal in need of such treatment. The method comprises administering to the mammal a therapeutically effective amount of a compound of formula (I) or a pharmaceutically acceptable salt thereof.

In another embodiment, the present invention provides a pharmaceutical composition comprising a therapeutically effective amount of a compound of the invention or a pharmaceutically acceptable salt thereof, in combination with one or more pharmaceutically acceptable carriers. The composition is preferably useful for the treatment of the disease conditions described above.

Further, the present invention provides the use of a compound of formula (I) or a pharmaceutically acceptable salt thereof, in the manufacture of a medicament for the treatment of the disease conditions described above.

These and other objects of the invention are provided in the Definition of the Terms and the Detailed Description. These objects should not be deemed to narrow the scope of the invention defined by the claims.

DETAILED DESCRIPTION

Compounds of formula (I) are disclosed in this invention,

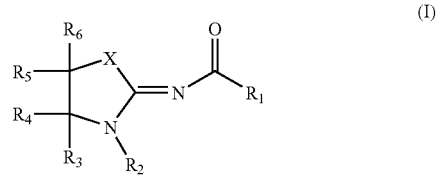

wherein X, $R_1$, $R_2$, $R_3$, $R_4$, $R_5$, and $R_6$ are as defined above in the Summary of the Invention and below in the Detailed Description. Compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

A. DEFINITIONS

As used in the specification and the appended claims, unless specified to the contrary, the following terms have the meaning indicated:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkyl" as used herein, means an alkoxyalkoxy group, as defined herein, appended to the parent molecular moiety through an alkylene group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

The term "alkoxyalkyl" as used herein, means an alkoxy group, as defined herein, appended to the parent molecular moiety through an alkylene group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkylene group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkyl" as used herein, means a straight or branched chain saturated hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl (3-methylbutyl), neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkylene group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain saturated hydrocarbon of from 1 to 10 carbon atoms. The term $C_2$-$C_6$ alkylene means a divalent group derived from a straight or branched chain saturated hydrocarbon of from 2 to 6 carbon atoms Representative examples of alkylene include, but are not limited to, —$CH_2$—, —$CH(CH_3)$—, —$C(CH_3)_2$—, —$CH_2CH_2$—, —$CH_2CH_2CH_2$—, —$CH_2CH_2CH_2CH_2$—, —$CH_2CH_2CH_2CH_2CH_2$—, —$CH_2CH(CH_3)CH_2$—, and —$CH_2C(CH_3)_2CH_2$—.

The term "alkylsulfinyl" as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl" as used herein, means an alkylsulfinyl group, as defined herein, appended to the parent molecular moiety through an alkylene group, as defined herein. Representative examples of alkylsulfinylalkyl include, but are not limited to, methylsulfinylmethyl and ethylsulfinylmethyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkylthioalkyl" as used herein, means an alkylthio group, as defined herein, appended to the parent molecular moiety through an alkylene group, as defined herein. Representative examples of alkylthioalkyl include, but are not limited to, methylthiomethyl and 2-(ethylthio)ethyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means phenyl, a bicyclic aryl or a tricyclic aryl. The bicyclic aryl is naphthyl, or a phenyl fused to a monocyclic cycloalkyl, or a phenyl fused to a monocyclic cycloalkenyl. Representative examples of bicyclic aryls include, but are not limited to, dihydroindenyl, indenyl, naphthyl, dihydronaphthalenyl, and tetrahydronaphthalenyl. The tricyclic aryl is exemplified by a bicyclic aryl fused to a monocyclic cycloalkyl, or a bicyclic aryl fused to a monocyclic cycloalkenyl, or a bicyclic aryl fused to a phenyl. Representative examples of tricyclic aryls include, but are not limited to, anthracene, phenanthrene, dihydroanthracenyl, fluorenyl, 1,2-dihydroacenaphthylenyl, and tetrahydrophenanthrenyl. The phenyl, bicyclic and tricyclic aryls are attached to the parent molecular moiety through any carbon atom contained within the phenyl, bicyclic and tricyclic aryls respectively.

The term "arylalkyl" as used herein, means an aryl group, as defined herein, appended to the parent molecular moiety through an alkylene group, as defined herein. Representative examples of arylalkyl include, but are not limited to, benzyl, 2-phenylethyl, 3-phenylpropyl, and 2-naphth-2-ylethyl.

The term "carbonyl" as used herein, means a —C(O)— group.

The term "carboxy" as used herein, means a —CO$_2$H group.

The term "carboxyalkyl" as used herein, means a carboxy group, as defined herein, appended to the parent molecular moiety through an alkylene group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkylene group, as defined herein. Representative examples of cyanoalkyl include, but are not limited to, cyanomethyl, 2-cyanoethyl, and 3-cyanopropyl.

The term "cycloalkenyl" as used herein, means a monocyclic or bicyclic ring system containing zero heteroatoms in the ring. The monocyclic cycloalkenyl has three, four, five, six, seven, eight, nine, or ten carbon atoms and zero heteroatoms. The three or four-membered ring systems have one double bond, the five- or six-membered ring systems have one or two double bonds, and the seven- or eight-membered ring systems have one, two or three double bonds. Representative examples of monocyclic ring systems include, but are not limited to, 2-cyclohexen-1-yl, 3-cyclohexen-1-yl, 2,4-cyclohexadien-1-yl and 3-cyclopenten-1-yl. Bicyclic ring systems are exemplified by a monocyclic cycloalkenyl ring fused to a monocyclic cycloalkyl ring, or a monocyclic cycloalkenyl ring fused to a monocyclic cycloalkenyl ring. Representative examples of bicyclic ring systems include, but are not limited to 3a, 4, 5, 6, 7, 7a-hexahydro-1H-indenyl, 4,5,6,7-tetrahydro-3aH-indene, and octahydronaphthalenyl. The monocyclic or the bicyclic cycloalkenyls are appended to the parent molecular moiety through any substitutable carbon atom within the monocyclic or the bicyclic cycloalkenyls respectively. The monocyclic and bicyclic cycloalkenyl groups of the present invention may contain one or two alkylene bridges of 1, 2, 3, or 4 carbon atoms, each of which linking two non adjacent carbon atoms of the group.

The term "cycloalkyl" as used herein, means a monocyclic, or a bicyclic ring system, or a spirocyclic cycloalkyl. The monocyclic cycloalkyl is a carbocyclic ring system containing 3, 4, 5, 6, 7, or 8 carbon atoms, zero heteroatoms and zero double bonds. Examples of monocyclic ring systems include cyclopropyl, cyclobutyl, cyclopentyl, cyclohexyl, cycloheptyl, and cyclooctyl. Bicyclic cycloalkyls are exemplified by a monocyclic cycloalkyl ring fused to a monocyclic cycloalkyl ring. Representative examples of bicyclic ring systems include, but are not limited to, bicyclo[4.1.0]heptane, bicyclo[6.1.0]nonane, octahydroindene, and decahydronaphthalene. Spirocyclic cycloalkyl is exemplified by a monocyclic cycloalkyl ring wherein two of the substituents on the same carbon atom of the ring, together with said carbon atom, form a 4-, 5-, or 6-membered monocyclic cycloalkyl. An example of a spirocyclic cycloalkyl is spiro[2.5]octane. The monocyclic, bicyclic and spirocyclic cycloalkyl groups of the present invention can be appended to the parent molecular moiety through any substitutable carbon atom of the groups. The monocyclic and bicyclic cycloalkyl groups of the present invention may contain one or two alkylene bridges of 1, 2, 3, or 4 carbon atoms, each of which linking two non adjacent carbon atoms of the group. Examples of such a bridged system include, but are not limited to, adamantane (tricyclo[3.3.1.1$^{3,7}$]decane) and bicyclo[2.2.1]heptane.

The term "cycloalkylalkyl," as used herein, means a cycloalkyl group appended to the parent molecular moiety through an alkylene group, as defined herein.

The term "cycloalkylalkoxy," as used herein, means a cycloalkylalkyl group appended to the parent molecular moiety through an oxygen atom.

The term "cycloalkylalkoxyalkyl," as used herein, means a cycloalkylalkoxy group appended to the parent molecular moiety through an alkylene group, as defined herein.

The term "cycloalkyloxy," as used herein, means a cycloalkyl group appended to the parent molecular moiety through an oxygen atom.

The term "cycloalkyloxyalkyl," as used herein, means a cycloalkyloxy group appended to the parent molecular moiety through an alkylene group, as defined herein.

The term "formyl" as used herein, means a —C(O)H group.

The term "formylalkyl" as used herein, means a formyl group, as defined herein, appended to the parent molecular moiety through an alkylene group, as defined herein. Representative examples of formylalkyl include, but are not limited to, formylmethyl and 2-formylethyl.

The term "halo" or "halogen" as used herein, means —Cl, —Br, —I, or —F.

The term "haloalkoxy" as used herein, means an alkoxy group, as defined herein, in which one, two, three, four, five, or six hydrogen atoms are replaced by halogen. Representative examples of haloalkoxy include, but are not limited to, trifluoromethoxy, difluoromethoxy, 2,2,2-trifluoroethoxy, and 2,2-difluoroethoxy.

The term "haloalkyl," as used herein, means at least one halogen, as defined herein, appended to the parent molecular moiety through an alkylene group, as defined herein. Representative examples of haloalkyl include, but are not limited to, chloromethyl, 2-fluoroethyl, trifluoromethyl, pentafluoroethyl, 4,4,4-trifluorobutyl, and 2-chloro-3-fluoropentyl.

The term "heteroaryl," as used herein, means a monocyclic heteroaryl or a bicyclic heteroaryl. The monocyclic heteroaryl is a 5 or 6 membered ring containing at least one heteroatom independently selected from the group consisting of O, N, and S. The 5-membered ring contains two double bonds, and one, two, three, or four heteroatoms as ring atoms. The 6-membered ring contains three double bonds, and one, two, three or four heteroatoms as ring atoms. Representative examples of monocyclic heteroaryl include, but are not limited to, furanyl (including furan-2-yl), imidazolyl, isoxazolyl, isothiazolyl, oxadiazolyl (including 1,2,4-oxadiazol-3-yl), oxazolyl, pyridinyl (including pyridin-2-yl, pyridin-3-yl, pyridin-4-yl), pyridazinyl, pyrimidinyl, pyrazinyl, pyrazolyl, pyrrolyl, tetrazolyl, thiadiazolyl, thiazolyl (including 1,3-thiazol-4-yl), thienyl (including thien-2-yl), triazolyl, and triazinyl. The bicyclic heteroaryl is exemplified by a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl include, but are not limited to, benzofuranyl, benzoxadiazolyl, 1,3-benzothiazolyl, benzimidazolyl, benzodioxolyl, benzothienyl, chromenyl, cinnolinyl, furopyridinyl, indolyl, indazolyl, isoindolyl, isoquinolinyl, naphthyridinyl, oxazolopyridine, quinolinyl, thienopyridinyl and thienopyridinyl. The monocyclic and the bicyclic heteroaryl groups are connected to the parent molecular moiety through any substitutable carbon atom or any substitutable nitrogen atom contained within the groups.

The term "heteroarylalkyl," as used herein, means a heteroaryl group appended to the parent molecular moiety through an alkylene group, as defined herein.

The term "heterocycle" or "heterocyclic" as used herein, refers to a monocyclic, bicyclic, tricyclic, or a spirocyclic ring system containing at least one heteroatom. The monocyclic heterocycle is a 3, 4, 5, 6, 7, or 8-membered ring containing at least one heteroatom in the ring, independently selected from the group consisting of O, N, and S. The 3 or 4 membered ring contains one heteroatom selected from the group consisting of O, N and S, and optionally one double bond. The 5-membered ring contains zero or one double bond, and one, two or three heteroatoms in the ring selected from the group consisting of O, N and S. The 6, 7, or 8-membered ring contains zero, one, or two double bonds, and one, two, or three heteroatoms in the ring selected from the group consisting of O, N and S. Representative examples of monocyclic heterocycle include, but are not limited to, azetidinyl, azepanyl, aziridinyl, diazepanyl, 1,3-dioxanyl, 1,4-dioxanyl, 1,3-dioxolanyl (including 1,3-dioxolan-4-yl), 4,5-dihydroisoxazol-5-yl, 3,4-dihydropyranyl (including 3,4-dihydro-2H-pyran-6-yl), 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl (including oxetan-2-yl), piperazinyl, piperidinyl, pyranyl, pyrazolinyl, pyrazolidinyl, pyrrolinyl, pyrrolidinyl, tetrahydrofuranyl (including tetrahydrofuran-2-yl, tetrahydrofuran-3-yl), tetrahydropyranyl (including tetrahydro-2H-pyran-2-yl, tetrahydro-2H-pyran-3-yl, tetrahydro-2H-pyran-4-yl), tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle of the present invention is exemplified by a monocyclic heterocycle fused to a phenyl group, or a monocyclic heterocycle fused to a monocyclic cycloalkyl group, or a monocyclic heterocycle fused to a monocyclic cycloalkenyl group, or a monocyclic heterocycle fused to a monocyclic heterocycle group. Representative examples of bicyclic heterocycle include, but are not limited to, 1,3-benzodioxol-4-yl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. Spirocyclic heterocycle means a 4,5-, 6-, 7-, or 8-membered monocyclic heterocycle ring wherein two of the substituents on the same carbon atom form a 3-, 4-, 5-, or 6-membered monocyclic ring selected from the group consisting of cycloalkyl and heterocycle, each of which is optionally substituted with 1, 2, 3, 4, or 5 alkyl groups. One example of a spiroheterocycle is 5-oxaspiro[3,4]octane. The tricyclic heterocycle is a bicyclic heterocycle fused to a phenyl, or a bicyclic heterocycle fused to a monocyclic cycloalkyl, or a bicyclic heterocycle fused to a monocyclic cycloalkenyl, or a bicyclic heterocycle fused to a monocyclic heterocycle. Representative examples of tricyclic heterocycle include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl. The monocyclic, bicyclic, tricyclic, and spirocyclic heterocycle groups are connected to the parent molecular moiety through any substitutable carbon atom or any substitutable nitrogen atom contained within the group. The monocyclic and bicyclic heterocycle groups of the present invention may contain one or two alkylene bridges of 1, 2, 3, or 4 carbon atoms, each linking two non-adjacent atoms of the group. Examples of such a bridged heterocycle include, but are not limited to, oxatricyclo[3.3.1.1$^{3,7}$]decane (oxaadamantane) and oxabicyclo[2.2.1]heptane.

The term "heterocycleoxy," as used herein, means a heterocycle group appended to the parent molecular moiety through an oxygen atom.

The term "heterocycleoxyalkyl," as used herein, means a heterocycleoxy group appended to the parent molecular moiety through an alkylene group, as defined herein.

The term "heterocyclealkyl," as used herein, means a heterocycle group appended to the parent molecular moiety through an alkylene group, as defined herein.

The aryl, cycloalkyl, cycloalkenyl, heterocycle, or heteroaryl moieties of this invention, as a substituent, or as part of a substituent, unless otherwise noted, is each independently unsubstituted or substituted with 1, 2, 3, 4, 5, or 6 substituents as described herein below, unless otherwise noted. The optional substituents are selected from the group consisting of alkenyl, alkoxy, alkoxyalkoxy, alkoxyalkoxyalkyl, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfinyl, alkylsulfinylalkyl, alkyl-S(O)$_2$—, alkyl-S(O)$_2$-alkyl-, alkyl-S—, alkyl-S-alkyl-, alkynyl, carboxy, carboxyalkyl, cyano, cyanoalkyl, formyl, formylalkyl, halogen, haloalkyl, haloalkoxy, hydroxy, hydroxyalkyl, oxo, —SH, N(O)$_2$, =N—O(alkyl), =N—OH, NZ$_1$Z$_2$-alkylene-O—, —NZ$_1$Z$_2$, and (NZ$_3$Z$_4$) carbonyl.

The term "hydroxy" as used herein, means an —OH group.

The term "hydroxyalkyl" as used herein, means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "hydroxy-protecting group" or "O-protecting group" means a substituent that protects hydroxyl groups against undesirable reactions during synthetic procedures. Examples of hydroxy-protecting groups include, but are not limited to, substituted methyl ethers, for example, methoxymethyl, benzyloxymethyl, 2-methoxyethoxymethyl, 2-(trimethylsilyl)-ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates. Commonly used hydroxy-protecting groups are disclosed in T. W. Greene and P. G. M. Wuts, Protective Groups in Organic Synthesis, 3rd edition, John Wiley & Sons, New York (1999).

The term "mercapto" as used herein, means a —SH group.

The term "nitrogen protecting group" as used herein, means those groups intended to protect an amino group against undesirable reactions during synthetic procedures. Preferred nitrogen protecting groups are acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl).

The term "nitro" as used herein, means a —NO$_2$ group.

The term "NZ$_1$Z$_2$" as used herein, means two groups, Z$_1$ and Z$_2$, which are appended to the parent molecular moiety through a nitrogen atom. Z$_1$ and Z$_2$ are each independently hydrogen, alkyl, alkoxyalkyl, alkylcarbonyl, aryl, arylalkyl, or formyl. In certain instances within the present invention, $Z_1$ and $Z_2$ taken together with the nitrogen atom to which they are attached form a heterocyclic ring. Representative examples of $NZ_1Z_2$ include, but are not limited to, amino, methylamino, acetylamino, acetylmethylamino, phenylamino, benzylamino, azetidinyl, pyrrolidinyl and piperidinyl.

The term "$NZ_3Z_4$" as used herein, means two groups, $Z_3$ and $Z_4$, which are appended to the parent molecular moiety through a nitrogen atom. $Z_3$ and $Z_4$ are each independently hydrogen, alkyl, haloalkyl, aryl and arylalkyl. Representative examples of $NZ_3Z_4$ include, but are not limited to, amino, methylamino, phenylamino and benzylamino.

The term "$(NZ_3Z_4)$carbonyl" as used herein, means a $NZ_3Z_4$ group, as defined herein, appended to the parent molecular moiety through a carbonyl group, as defined herein. Representative examples of $(NZ_3Z_4)$carbonyl include, but are not limited to, aminocarbonyl, (methylamino)carbonyl, (dimethylamino)carbonyl, and (ethylmethylamino)carbonyl.

The term "oxo" as used herein, means a $=O$ moiety.

The term "sulfinyl" as used herein, means a $—S(O)—$ group.

Compounds of the invention have the formula (I) as described above.

Particular values of variable groups in compounds of formula (I) are as follows. Such values may be used where appropriate with any of the other values, definitions, claims or embodiments defined hereinbefore or hereinafter.

In compounds of formula (I), $R_1$ is as described in the Summary. In one embodiment, $R_1$ is phenyl substituted with 1, 2, 3, 4, or 5 substituents as represented by $R_j$. Examples of the substituents as represented by $R_j$ include, but are not limited to, alkoxy (for example, methoxy), alkyl (for example, methyl), halogen (for example, Cl, Br, F), haloalkoxy (for example, trifluoromethoxy, 2,2,2-trifluoroethoxy), formyl, cyano, $=N—O(alkyl)$, $=N—OH$, and $—NZ_1Z_2$ wherein $Z_1$ and $Z_2$ are as described in the Definitions. In another embodiment, $R_1$ is optionally substituted cycloalkyl (for example, adamantyl). In yet another embodiment, $R_1$ is heterocycle (for example, oxatricyclo[3.3.1.1$^{3,7}$]decan-1-yl, 3,4-dihydro-2H-pyranyl, tetrahydro-2H-pyranyl), optionally substituted as described in the Summary. Examples of the optional substituents of the cycloalkyl and heterocycle of $R_1$ include, but are not limited to, alkyl (for example, methyl) and oxo. In a further embodiment, $R_1$ is formula (i), (ii), (iii), or (iv), particularly, $R_1$ has formula (II) or (iii), wherein each of the formulae is optionally further substituted as disclosed in the Summary X is O or S. Certain compounds of the invention include those wherein X is O. Yet others include those wherein X is S.

$R_2$ has values as disclosed in the Summary. Examples of compounds of formula (I) include those wherein $R_2$ is alkyl. Examples of $R_2$ as alkyl include, but are not limited to, n-butyl, n-propyl, n-pentyl, 3-methylbutyl, iso-butyl, and neopentyl. Other compounds of formula (I) include, but are not limited to, those wherein $R_2$ is alkoxy-$(C_2-C_6$ alkylene) such as 2-methoxyethyl. Yet other examples of compounds of formula (I) include, but are not limited to, those wherein $R_2$ is arylalkyl. Particularly, $R_2$ is phenylmethyl wherein the phenyl moiety is optionally substituted as described in the Definitions, for example, the phenyl moiety is optionally substituted with 1 or 2 halogen (for example, F). Further examples of compounds of formula (I) include, but are not limited to, those wherein $R_2$ is cycloalkylalkyl (for example, cyclobutylmethyl) wherein the cycloalkyl moiety is optionally substituted as described in the Definitions. Yet other examples of compounds of formula (I) include, but are not limited to, those wherein $R_2$ is haloalkyl (for example, 4,4,4-trifluorobutyl). In yet other embodiment, $R_2$ is heteroarylalkyl wherein the heteroaryl moiety is optionally substituted. Examples of the heteroaryl moiety of the heteroarylalkyl include, but are not limited to, thienyl, 1,3-thiazolyl, pyridinyl, 1,2,4-oxadiazolyl, furanyl, each of which is optionally substituted. In yet another embodiment, $R_2$ is heterocyclealkyl wherein the heterocycle moiety is optionally substituted. Examples of the heterocycle moiety of the heterocyclealkyl include, but are not limited to, tetrahydrofuranyl (including tetrahydrofuran-2-yl), tetrahydro-2H-pyranyl (including tetrahydro-2H-pyran-3-yl, tetrahydro-2H-pyran-2-yl), oxetanyl (including oxetan-2-yl), and 1,3-dioxolanyl (including 1,3-dioxolan-4-yl), each of which is optionally substituted as disclosed in the Definitions, for example, each of which is optionally substituted with 1, 2, 3, or 4 substituents selected from the group consisting of alkyl (for example, methyl) and oxo.

$R_3$ and $R_4$ have values as disclosed in the Summary. In one embodiment, $R_3$ and $R_4$ are each independently hydrogen or alkyl (for example, methyl).

$R_5$ and $R_6$ have values as disclosed in the Summary. In one embodiment, $R_5$ and $R_6$ are each independently hydrogen, alkyl (for example, methyl, ethyl, isopropyl, tert-butyl, propyl), or optionally substituted aryl (for example, phenyl optionally substituted with halogen). In another embodiment, $R_5$ and $R_6$ together with the carbon atoms to which they are attached form a monocyclic cycloalkyl or a monocyclic heterocyclic ring, each of which is optionally substituted as described in the Definitions. In yet another embodiment, $R_5$ and $R_6$ together with the carbon atoms to which they are attached form an optionally substituted monocyclic cycloalkyl ring (for example, cyclobutyl, cyclopentyl, cyclohexyl).

In yet another embodiment, $R_4$ and $R_6$ are each independently hydrogen or alkyl (for example, methyl), and $R_3$ and $R_5$ together with the atoms to which they are attached form an optionally substituted monocyclic cycloalkyl or an optionally substituted monocyclic heterocyclic ring provided that the monocyclic heterocyclic ring is saturated and contains at least one oxygen. In yet another embodiment, $R_4$ and $R_6$ are hydrogen, and $R_3$ and $R_5$ together with the atoms to which they are attached form an optionally substituted monocyclic cycloalkyl ring (for example, cyclohexyl).

It is appreciated that the present invention contemplates compounds of formula (I) with combinations of the above embodiments, including particular, more particular and preferred embodiments.

Accordingly, one aspect of the invention provides compounds of formula (I) wherein X is S; $R_1$ is phenyl substituted with 1, 2, 3, 4, or 5 substituents as represented by $R_j$; $R_5$ and $R_6$ are each independently hydrogen, alkyl, or aryl; $R_3$ and $R_4$ are each independently hydrogen or alkyl; and $R_2$ is alkyl or haloalkyl.

Another aspect of the invention provides compounds of formula (I) wherein X is S; $R_1$ is phenyl substituted with 1, 2, 3, 4, or 5 substituents as represented by $R_j$; $R_5$ and $R_6$ are each independently hydrogen, alkyl, or aryl; $R_3$ and $R_4$ are each independently hydrogen or alkyl; and $R_2$ is alkoxy-$(C_2-C_6$ alkylene)-.

Yet another aspect of the invention provides compounds of formula (I) wherein X is S; $R_1$ is phenyl substituted with 1, 2, 3, 4, or 5 substituents as represented by $R_j$; $R_5$ and $R_6$ are each independently hydrogen, alkyl, or aryl; $R_3$ and $R_4$ are each independently hydrogen or alkyl; and $R_2$ is heterocyclealkyl.

A further aspect of the invention is directed to compounds of formula (I) wherein X is S; $R_1$ is phenyl substituted with 1, 2, 3, 4, or 5 substituents as represented by $R_j$; $R_5$ and $R_6$ are each independently hydrogen, alkyl, or aryl; $R_3$ and $R_4$ are each independently hydrogen or alkyl; and $R_2$ is cycloalkylalkyl.

Still another aspect of the invention is directed to compounds of formula (I) wherein X is S; $R_1$ is phenyl substituted with 1, 2, 3, 4, or 5 substituents as represented by $R_j$; $R_5$ and $R_6$ are each independently hydrogen, alkyl, or aryl; $R_3$ and $R_4$ are each independently hydrogen or alkyl; and $R_2$ is arylalkyl. Another aspect of the invention is directed to compounds of formula (I) wherein X is S; $R_1$ is phenyl substituted with 1, 2, 3, 4, or 5 substituents as represented by $R_j$; $R_5$ and $R_6$ are each independently hydrogen, alkyl, or aryl; $R_3$ and $R_4$ are each independently hydrogen or alkyl; and $R_2$ is heteroarylalkyl.

Yet another aspect of the invention provides compounds of formula (I) wherein X is S; $R_1$ is phenyl substituted with 1, 2, 3, 4, or 5 substituents as represented by $R_j$; $R_5$ and $R_6$ taken together with the carbon atom to which they are attached form a monocyclic cycloalkyl ring or a monocyclic heterocyclic ring; $R_3$ and $R_4$ are each independently hydrogen or alkyl; and $R_2$ is alkyl. Yet another aspect of the invention provides compounds of formula (I) wherein X is S; $R_1$ is phenyl substituted with 1, 2, 3, 4, or 5 substituents as represented by $R_j$; $R_5$ and $R_6$ taken together with the carbon atom to which they are attached form a monocyclic cycloalkyl ring or a monocyclic heterocyclic ring; $R_3$ and $R_4$ are each independently hydrogen or alkyl; and $R_2$ is heterocyclealkyl.

Yet another aspect of the invention provides compounds of formula (I) wherein X is S; $R_1$ is phenyl substituted with 1, 2, 3, 4, or 5 substituents as represented by $R_j$; $R_3$ and $R_5$ taken together with the atoms to which they are attached form a monocyclic cycloalkyl or a monocyclic heterocyclic ring provided that the monocyclic heterocyclic ring is saturated and contains at least one oxygen; $R_4$ and $R_6$ are each independently hydrogen or alkyl; and $R_2$ is alkyl.

Within each group of compounds of formula (I) as described herein above, $R_j$ has values as disclosed in the Summary. Examples of the substituents as represented by $R_j$ include, but are not limited to, alkoxy (for example, methoxy), alkyl (for example, methyl), halogen (for example, Cl, Br, F), haloalkoxy (for example, trifluoromethoxy, 2,2,2-trifluoroethoxy), formyl, cyano, =N—O(alkyl), =N—OH, and —$NZ_1Z_2$ wherein $Z_1$ and $Z_2$ are as described in the Definitions.

Yet another aspect of the invention provides compounds of formula (I) wherein X is S; $R_1$ is formula (i), (ii), (iii), or (iv)

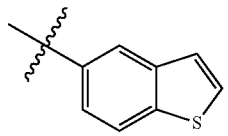

each of the formula (i), (ii), (iii), or (iv) is optionally further substituted with 1, 2, or 3 substituents as represented by $R_j$; $R_5$ and $R_6$ are each independently hydrogen, alkyl, or aryl; or $R_5$ and $R_6$ taken together with the carbon atom to which they are attached form a monocyclic cycloalkyl ring; $R_3$ and $R_4$ are each independently hydrogen or alkyl; and $R_2$ is alkyl.

A further aspect of the invention provides compounds of formula (I) wherein X is S; $R_1$ is each of the formula (i), (ii), (iii), or (iv) is optionally further substituted with 1, 2, or 3 substituents as represented by $R_j$; $R_5$ and $R_6$ are each independently hydrogen, alkyl, or aryl; or $R_5$ and $R_6$ taken together with the carbon atom to which they are attached form a monocyclic cycloalkyl ring; $R_3$ and $R_4$ are each independently hydrogen or alkyl; and $R_2$ is heterocyclealkyl.

A further aspect of the invention provides compounds of formula (I) wherein X is S; $R_1$ is heterocycle, optionally further substituted with 1, 2, or 3 substituents as represented by $R_j$; $R_5$ and $R_6$ are each independently hydrogen, alkyl, or aryl; $R_3$ and $R_4$ are each independently hydrogen or alkyl; $R_2$ is alkyl; and $R_j$ is as disclosed in the Summary. For example, $R_j$ is alkyl (e.g. methyl) or oxo.

Yet a further aspect of the invention is directed to compounds of formula (I) wherein X is S; $R_1$ is heterocycle, optionally further substituted with 1, 2, or 3 substituents as represented by $R_j$; $R_5$ and $R_6$ taken together with the carbon atom to which they are attached form a monocyclic cycloalkyl ring; $R_3$ and $R_4$ are each independently hydrogen or alkyl; $R_2$ is heterocyclealkyl, and $R_j$ is as disclosed in the Summary. For example, $R_j$ is alkyl (e.g. methyl) or oxo.

Still another aspect of the invention is directed to compounds of formula (I) wherein X is S; R₁ is

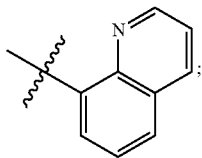

(ii)

wherein formula (II) is optionally further substituted as described in the Summary; R₅ and R₆ are each independently hydrogen, alkyl or aryl; R₃ and R₄ are each independently hydrogen or alkyl; R$_j$ is alkoxy or halogen; and R₂ is alkyl.

Still another aspect of the invention is directed to compounds of formula (I) wherein X is S; and R₁ is

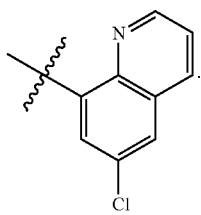

Other compounds of the present invention includes, but are not limited to, those of formula (I) wherein X is S; R₁ is cycloalkyl, optionally further substituted with 1, 2, or 3 substituents as represented by R$_j$; R₅ and R₆ are each independently hydrogen, alkyl, or aryl; R₃ and R₄ are each independently hydrogen or alkyl; R₂ is alkyl; and R$_j$ is as disclosed in the Summary. For example, R$_j$ is alkyl (e.g. methyl) or oxo.

Yet other aspect of the invention is directed to compounds of formula (I) wherein X is O; R₁ is phenyl substituted with 1, 2, 3, 4, or 5 substituents as represented by R$_j$; R₅ and R₆ are each independently hydrogen, alkyl, or aryl; R₃ and R₄ are each independently hydrogen or alkyl; d R₂ is alkyl or haloalkyl, and R$_j$ is as disclosed in the Summary. Examples of the substituents as represented by R$_j$ include, but are not limited to, alkoxy (for example, methoxy), alkyl (for example, methyl), halogen (for example, Cl, Br, F), haloalkoxy (for example, trifluoromethoxy, 2,2,2-trifluoroethoxy), formyl, cyano, =N—O(alkyl), =N—OH, and —NZ₁Z₂ wherein Z₁ and Z₂ are as described in the Definitions.

Exemplary compounds of formula (I) include, but are not limited to:

5-chloro-2-methoxy-N-[(2Z)-3-(2-methoxyethyl)-5,5-dimethyl-1,3-thiazolidin-2-ylidene]benzamide;
N-[(2Z)-3-butyl-5,5-dimethyl-1,3-thiazolidin-2-ylidene]-5-chloro-2-methoxybenzamide;
N-[(2Z)-3-butyl-5-tert-butyl-1,3-thiazolidin-2-ylidene]-5-chloro-2-methoxybenzamide;
N-[(2Z)-3-butyl-5-tert-butyl-1,3-thiazolidin-2-ylidene]-4-chloro-2-methoxybenzamide;
4-bromo-N-[(2Z)-3-butyl-5-tert-butyl-1,3-thiazolidin-2-ylidene]-2-methoxybenzamide;
N-[(2Z)-3-butyl-5-tert-butyl-1,3-thiazolidin-2-ylidene]-5-chloro-2-(trifluoromethoxy)benzamide;
N-[(2Z)-3-butyl-5-propyl-1,3-thiazolidin-2-ylidene]-5-chloro-2-methoxybenzamide;
N-[(2Z)-3-butyl-5-ethyl-5-methyl-1,3-thiazolidin-2-ylidene]-5-chloro-2-methoxybenzamide;
N-[(2Z)-3-butyl-5-methyl-1,3-thiazolidin-2-ylidene]-5-chloro-2-methoxybenzamide;
N-[(2Z)-3-butyl-5-(4-fluorophenyl)-1,3-thiazolidin-2-ylidene]-5-chloro-2-methoxybenzamide;
N-[(2Z)-3-butyl-5-tert-butyl-5-methyl-1,3-thiazolidin-2-ylidene]-5-chloro-2-methoxybenzamide;
N-[(2Z)-3-butyl-5-tert-butyl-5-methyl-1,3-thiazolidin-2-ylidene]-4-chloro-2-methoxybenzamide;
4-bromo-N-[(2Z)-3-butyl-5-methyl-1,3-thiazolidin-2-ylidene]-2-methoxybenzamide;
N-[(2Z)-3-butyl-5-methyl-1,3-thiazolidin-2-ylidene]-6-chloroquinoline-8-carboxamide;
N-[(2Z)-3-butyl-1-thia-3-azaspiro[4.4]non-2-ylidene]-5-chloro-2-methoxybenzamide;
N-[(2Z)-3-butyl-1-thia-3-azaspiro[4.5]dec-2-ylidene]-5-chloro-2-methoxybenzamide;
trans-N-[(2Z)-3-butyl-4,5-dimethyl-1,3-thiazolidin-2-ylidene]-5-chloro-2-methoxybenzamide;
cis-N-[(2Z)-3-butyl-4,5-dimethyl-1,3-thiazolidin-2-ylidene]-5-chloro-2-methoxybenzamide;
N-[(2Z)-3-butyl-5,5-dimethyl-1,3-thiazolidin-2-ylidene]-2,2-dimethyl-4-oxo-3,4-dihydro-2H-pyran-6-carboxamide;
N-[(2Z)-3-butyl-5,5-dimethyl-1,3-thiazolidin-2-ylidene]-2,2-dimethyltetrahydro-2H-pyran-4-carboxamide;
5-chloro-N-{(2Z)-5,5-dimethyl-3-[(2R)-tetrahydrofuran-2-ylmethyl]-1,3-thiazolidin-2-ylidene}-2-methoxybenzamide;
5-chloro-N-{(2Z)-5,5-dimethyl-3-[(2R)-tetrahydrofuran-2-ylmethyl]-1,3-thiazolidin-2-ylidene}-2-(2,2,2-trifluoroethoxy)benzamide;
5-chloro-N-{(2Z)-5,5-dimethyl-3-[(2S)-tetrahydrofuran-2-ylmethyl]-1,3-thiazolidin-2-ylidene}-2-methoxybenzamide;
5-chloro-N-[(2Z)-3-(2,4-difluorobenzyl)-5,5-dimethyl-1,3-thiazolidin-2-ylidene]-2-methoxybenzamide;
5-chloro-N-[(2Z)-3-(3-fluorobenzyl)-5,5-dimethyl-1,3-thiazolidin-2-ylidene]-2-methoxybenzamide;
5-chloro-N-[(2Z)-5,5-dimethyl-3-(oxetan-2-ylmethyl)-1,3-thiazolidin-2-ylidene]-2-methoxybenzamide;
5-chloro-N-[(2Z)-3-isobutyl-5,5-dimethyl-1,3-thiazolidin-2-ylidene]-2-methoxybenzamide;
5-chloro-N-[(2Z)-3-(cyclobutylmethyl)-5,5-dimethyl-1,3-thiazolidin-2-ylidene]-2-methoxybenzamide;
N-[(2Z)-3-butyl-5,5-dimethyl-1,3-thiazolidin-2-ylidene]-5-chloro-2-(trifluoromethoxy)benzamide;
4-bromo-N-[(2Z)-3-butyl-5,5-dimethyl-1,3-thiazolidin-2-ylidene]-2-methoxybenzamide;
N-[(2Z)-3-butyl-5,5-dimethyl-1,3-thiazolidin-2-ylidene]adamantane-1-carboxamide;
N-[(2Z)-3-butyl-5,5-dimethyl-1,3-thiazolidin-2-ylidene]-2-oxatricyclo[3.3.1.1$^{3,7}$]decane-1-carboxamide;
N-[(2Z)-3-butyl-5,5-dimethyl-1,3-thiazolidin-2-ylidene]-4-chloro-2-methoxybenzamide;
N-[(2Z)-3-butyl-5,5-dimethyl-1,3-thiazolidin-2-ylidene]-6-chloroquinoline-8-carboxamide;
trans-N-[(2Z)-3-butylhexahydro-1,3-benzothiazol-2(3H)-ylidene]-5-chloro-2-methoxybenzamide;
N-[(2Z)-3-butyl-5-methyl-1,3-thiazolidin-2-ylidene]-5-chloro-2-methoxybenzamide
N-[(2Z)-3-butyl-5-isopropyl-1,3-thiazolidin-2-ylidene]-5-chloro-2-methoxybenzamide;
N-[(2Z)-3-butyl-5-ethyl-1,3-thiazolidin-2-ylidene]-5-chloro-2-methoxybenzamide;
5-chloro-N-[(2Z)-5,5-dimethyl-3-neopentyl-1,3-thiazolidin-2-ylidene]-2-methoxybenzamide;

N-[(2Z)-3-butyl-5,5-diethyl-1,3-thiazolidin-2-ylidene]-5-chloro-2-methoxybenzamide;

5-chloro-N-[(2Z)-5,5-dimethyl-3-propyl-1,3-thiazolidin-2-ylidene]-2-methoxybenzamide;

5-chloro-N-[(2Z)-3-(2-fluorobenzyl)-5,5-dimethyl-1,3-thiazolidin-2-ylidene]-2-methoxybenzamide;

5-chloro-N-[(2Z)-3-(2,6-difluorobenzyl)-5,5-dimethyl-1,3-thiazolidin-2-ylidene]-2-methoxybenzamide;

5-chloro-N-[(2Z)-3-(4-fluorobenzyl)-5,5-dimethyl-1,3-thiazolidin-2-ylidene]-2-methoxybenzamide;

5-chloro-N-[(2Z)-5,5-dimethyl-3-pentyl-1,3-thiazolidin-2-ylidene]-2-methoxybenzamide;

5-chloro-N-[(2Z)-3-(3,4-difluorobenzyl)-5,5-dimethyl-1,3-thiazolidin-2-ylidene]-2-methoxybenzamide;

5-chloro-N-[(2Z)-3-(2,5-difluorobenzyl)-5,5-dimethyl-1,3-thiazolidin-2-ylidene]-2-methoxybenzamide;

5-chloro-N-[(2Z)-3-(3,5-difluorobenzyl)-5,5-dimethyl-1,3-thiazolidin-2-ylidene]-2-methoxybenzamide;

5-chloro-N-[(2Z)-5,5-dimethyl-3-(3-methylbutyl)-1,3-thiazolidin-2-ylidene]-2-methoxybenzamide;

5-chloro-N-[(2Z)-3-(2,3-difluorobenzyl)-5,5-dimethyl-1,3-thiazolidin-2-ylidene]-2-methoxybenzamide;

5-chloro-N-[(2Z)-5,5-dimethyl-3-(4,4,4-trifluorobutyl)-1,3-thiazolidin-2-ylidene]-2-methoxybenzamide;

N-[(2Z)-3-butyl-5,5-dimethyl-1,3-thiazolidin-2-ylidene]-1-benzofuran-5-carboxamide;

N-[(2Z)-3-butyl-1-thia-3-azaspiro[4.4]non-2-ylidene]-1-benzofuran-5-carboxamide;

N-[(2Z)-3-butyl-1-thia-3-azaspiro[4.4]non-2-ylidene]-2-methyl-1-benzofuran-5-carboxamide;

2,2-dimethyl-4-oxo-N-{(2Z)-3-[(2S)-tetrahydrofuran-2-ylmethyl]-1-thia-3-azaspiro[4.5]dec-2-ylidene}-3,4-dihydro-2H-pyran-6-carboxamide;

N-[(2Z)-3-butyl-5,5-dimethyl-1,3-thiazolidin-2-ylidene]-2-methyl-1-benzofuran-5-carboxamide;

N-{(2Z)-3-[(2S)-tetrahydrofuran-2-ylmethyl]-1-thia-3-azaspiro[4.5]dec-2-ylidene}-1-benzofuran-5-carboxamide;

2,2-dimethyl-4-oxo-N-{(6Z)-7-[(2R)-tetrahydrofuran-2-ylmethyl]-5-thia-7-azaspiro[3.4]oct-6-ylidene}-3,4-dihydro-2H-pyran-6-carboxamide;

N-{(6Z)-7-[(2R)-tetrahydrofuran-2-ylmethyl]-5-thia-7-azaspiro[3.4]oct-6-ylidene}-1-benzofuran-5-carboxamide;

5-chloro-2-methoxy-N-{(6Z)-7-[(2R)-tetrahydrofuran-2-ylmethyl]-5-thia-7-azaspiro[3.4]oct-6-ylidene}benzamide;

N-[(6Z)-7-butyl-5-thia-7-azaspiro[3.4]oct-6-ylidene]-5-chloro-2-methoxybenzamide;

4-bromo-N-[(6Z)-7-butyl-5-thia-7-azaspiro[3.4]oct-6-ylidene]-2-methoxybenzamide;

4-bromo-2-methoxy-N-{(6Z)-7-[(2R)-tetrahydrofuran-2-ylmethyl]-5-thia-7-azaspiro[3.4]oct-6-ylidene}benzamide;

5-chloro-N-[(2Z)-5,5-dimethyl-3-(tetrahydrofuran-3-ylmethyl)-1,3-thiazolidin-2-ylidene]-2-methoxybenzamide;

5-chloro-N-[(2Z)-5,5-dimethyl-3-(tetrahydro-2H-pyran-3-ylmethyl)-1,3-thiazolidin-2-ylidene]-2-methoxybenzamide;

5-chloro-N-[(2Z)-5,5-dimethyl-3-(tetrahydro-2H-pyran-2-ylmethyl)-1,3-thiazolidin-2-ylidene]-2-methoxybenzamide;

5-chloro-N-((2Z)-5,5-dimethyl-3-{[(2R)-5-oxotetrahydrofuran-2-yl]methyl}-1,3-thiazolidin-2-ylidene)-2-methoxybenzamide;

5-chloro-N-((2Z)-3-{[(4S)-2,2-dimethyl-1,3-dioxolan-4-yl]methyl}-5,5-dimethyl-1,3-thiazolidin-2-ylidene)-2-methoxybenzamide;

N-[(2Z)-3-butyl-4,4-dimethyl-1,3-thiazolidin-2-ylidene]-5-chloro-2-methoxybenzamide;

4-bromo-N-[(2Z)-3-butyl-4,4-dimethyl-1,3-thiazolidin-2-ylidene]-2-methoxybenzamide;

5-chloro-N-[(2Z)-5,5-dimethyl-3-(1,2,4-oxadiazol-3-ylmethyl)-1,3-thiazolidin-2-ylidene]-2-methoxybenzamide;

5-chloro-N-{(2Z)-3-[(5-chlorothien-2-yl)methyl]-5,5-dimethyl-1,3-thiazolidin-2-ylidene}-2-methoxybenzamide;

5-chloro-N-[(2Z)-5,5-dimethyl-3-(1,3-thiazol-4-ylmethyl)-1,3-thiazolidin-2-ylidene]-2-methoxybenzamide;

5-chloro-N-[(2Z)-5,5-dimethyl-3-(pyridin-4-ylmethyl)-1,3-thiazolidin-2-ylidene]-2-methoxybenzamide;

5-chloro-N-[(2Z)-5,5-dimethyl-3-(pyridin-3-ylmethyl)-1,3-thiazolidin-2-ylidene]-2-methoxybenzamide;

5-chloro-N-[(2Z)-5,5-dimethyl-3-(pyridin-2-ylmethyl)-1,3-thiazolidin-2-ylidene]-2-methoxybenzamide;

5-chloro-N-[(2Z)-3-(2-furylmethyl)-5,5-dimethyl-1,3-thiazolidin-2-ylidene]-2-methoxybenzamide;

5-chloro-N-{(2Z)-3-[(5-fluoropyridin-3-yl)methyl]-5,5-dimethyl-1,3-thiazolidin-2-ylidene}-2-methoxybenzamide;

5-chloro-N-{(2Z)-3-[(2-fluoropyridin-3-yl)methyl]-5,5-dimethyl-1,3-thiazolidin-2-ylidene}-2-methoxybenzamide;

5-chloro-N-{(2Z)-3-[(6-fluoropyridin-3-yl)methyl]-5,5-dimethyl-1,3-thiazolidin-2-ylidene}-2-methoxybenzamide;

5-chloro-N-[(2Z)-5,5-dimethyl-3-(2-pyridin-2-ylethyl)-1,3-thiazolidin-2-ylidene]-2-methoxybenzamide;

5-chloro-N-[(2Z)-3-(3-furylmethyl)-5,5-dimethyl-1,3-thiazolidin-2-ylidene]-2-methoxybenzamide;

5-chloro-N-[(2Z)-5,5-dimethyl-3-(thien-3-ylmethyl)-1,3-thiazolidin-2-ylidene]-2-methoxybenzamide; and (Z)-N-(5-tert-butyl-3-butyloxazolidin-2-ylidene)-5-chloro-2-methoxybenzamide.

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The present invention contemplates various stereoisomers and mixtures of various ratios thereof. These stereoisomers and mixtures of various ratios thereof are included within the scope of this invention. Individual stereoisomers of compounds of the present invention may be prepared synthetically from commercially available starting materials containing asymmetric or chiral centers or by preparation of racemic mixtures followed by resolution well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers can exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen double bond are designated as being of Z or E configuration and substituents around a cycloalkyl or heterocycle are designated as being of cis or trans configuration.

For example, compounds of general formula (I) wherein $R_3$ and $R_5$ form a cyclohexyl ring as depicted in formula (II)

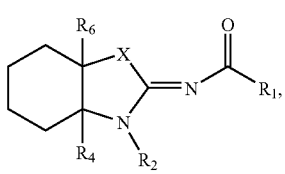

(II)

wherein $R_4$, $R_6$, $R_2$, X, and $R_1$ have values as disclosed for formula (I) in the Summary and the Detailed Description sections, may exhibit cis ((IIa), (IIb), or mixtures thereof) or trans ((IIc), (IId), or mixtures thereof) configuration.

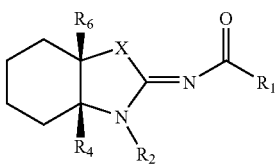

(IIa)

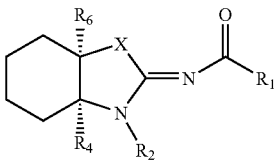

(IIb)

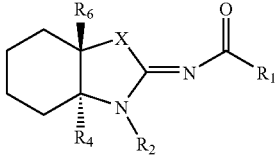

(IIc)

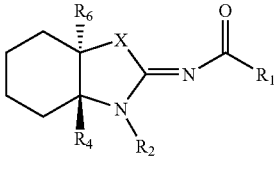

(IId)

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

C. BIOLOGICAL DATA (i) In Vitro Methods—$CB_2$ and $CB_1$ Radioligand Binding Assays:

The $CB_1$ and $CB_2$ radioligand binding assays described herein are utilized to determine the selectivity of compounds of the present invention for binding to $CB_2$ relative to $CB_1$ receptors.

HEK293 cells stably expressing human $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 5 μg/well for human $CB_2$) into wells of a deep well plate containing ([$^3$H] CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 90 min incubation at 30° C., binding reaction was terminated by the addition of 300 μl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations of displacing ligands selected from the range of 0.01 nM to 10 μM. The addition of 10 μM unlabeled CP-55,940 (Tocris, Ellisville, Mo.) was used to assess nonspecific binding.

HEK293 cells stably expressing rat $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 20 μg/well for rat $CB_2$) into wells of a deep well plate containing [$^3$H]CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 45 min incubation at 30° C., binding reaction was terminated by the addition of 300 μl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H] CP-55,940 and five concentrations of displacing ligands selected from the range of 0.01 nM to 10 μM. The addition of 10 μM unlabeled CP-55,940 (Tocris, Ellisville, Mo.) was used to assess nonspecific binding.

Compounds of the invention tested were found to bind to $CB_2$ receptors with $K_i$ of less than about 1,000 nM, preferably less than 400 nM, more preferably less than 200 nM, and most preferably lower than 100 nM.

HEK293 human $CB_1$ membranes were purchased from Perkin Elmer. Binding was initiated by the addition of membranes (8-12 μg per well) into wells (Scienceware 96-well DeepWell plate, VWR, West Chester, Pa.) containing [$^3$H] CP-55,940 (120 Ci/mmol, Perkin Elmer, Boston, Mass.) and a sufficient volume of assay buffer (50 mM Tris, 2.5 mM EDTA, 5 mM $MgCl_2$, and 0.5 mg/mL fatty acid free BSA, pH 7.4) to bring the total volume to 250 μL. After incubation (30° C. for 90 minutes), binding was terminated by the addition of 300 μL per well of cold assay buffer and rapid vacuum filtration (FilterMate Cell Harvester, Perkin Elmer, Boston, Mass.) through a UniFilter-96 GF/C filter plate (Perkin Elmer, Boston, Mass.) (pre-soaked in 0.3% PEI at least 3 hours), followed by five washes with cold assay buffer. The bound activity was counted in the TopCount using Microscint-20 (both from Perkin Elmer, Boston, Mass.). Competition experiments were conducted with 1 nM [$^3$H]CP-55,940 and five concentrations (1 nM to 10 µM) of displacing ligands. The addition of 10 µM unlabeled CP-55,940 (Tocris, Ellisville, Mo.) was used to assess nonspecific binding. The compounds of the present invention tested were found to bind to $CB_1$ receptors with $K_i$ of about 10 fold to about 1000 fold higher than that for $CB_2$ receptors. These results demonstrate that the compounds of the present invention tested preferably bind to $CB_2$ vs. $CB_1$ receptors, and therefore are selective ligands for the $CB_2$ receptor.

(ii) In Vivo Data:

Animals

Adult male Sprague-Dawley rats (250-300 g body weight, Charles River Laboratories, Portage, Mich.) were used. Animal handling and experimental protocols were approved by the Institutional Animal Care and Use Committee (IACUC) at Abbott Laboratories. For all surgical procedures, animals were maintained under halothane anesthesia (4% to induce, 2% to maintain), and the incision sites were sterilized using a 10% povidone-iodine solution prior to and after surgeries.

Incision Model of Postoperative Pain

A skin incision model of postoperative pain was produced using the procedures described in Brennan et al., 1996, Pain, 64, 493. All rats were anesthetized with isofluorane delivered via a nose cone. Right hind paw incision was performed following sterilization procedures. The plantar aspect of the left hind paw was placed through a hole in a sterile plastic drape. A 1-cm longitudinal incision was made through the skin and fascia of the plantar aspect of the hind paw, starting 0.5 cm from the proximal edge of the heel and extending towards the toes, the plantar muscle was elevated and incised longitudinally leaving the muscle origin and insertion points intact. The skin was then closed with two mattress sutures (5-0 nylon). After surgery, animals were then allowed to recover for 2 hours, at which time tactile allodynia was assessed as described below. To evaluate the anti-nociceptive effects, animals were i.p. administered vehicle or test compound 90 minutes following skin incision and tactile allodynia was assessed 30 minutes after compound administration.

Tactile allodynia was measured using calibrated von Frey filaments (Stoelting, Wood Dale, Ill.) as described in Chaplan, S. R., F. W. Bach, J. W. Porgrel, J. M. Chung and T. L. Yaksh, 1994, Quantitative assessment of tactile allodynia in the rat paw, J. Neurosci. Methods, 53, 55. Rats were placed into inverted individual plastic cage (20×12.5×20 cm) on top of a suspended wire mesh grid, and acclimated to the test chambers for 20 minutes. The von Frey filaments were applied perpendicularly from underneath the cage through openings in the wire mesh floor directly to an area within 1-3 mm (immediately adjacent) of the incision, and then held in this position for approximately 8 seconds with enough force to cause a slight bend in the filament. Positive responses included an abrupt withdrawal of the hind paw from the stimulus, or flinching behavior immediately following removal of the stimulus. A 50% withdrawal threshold was determined using an up-down procedure as described in Dixon, W. J., 1980, Efficient analysis of experimental observations, Ann. Rev. Pharmacol. Toxicol., 20, 441.

Certain compounds of the present invention tested showed a statistically significant change in paw withdrawal latency versus a saline vehicle at less than about 300 micromoles/kg in the incision model of postoperative pain. In a more preferred embodiment, compounds of the present invention tested showed efficacy at less than about 50 micromoles/kg in the incision model of postoperative pain.

Spinal Nerve Ligation Model of Neuropathic Pain

A model of spinal nerve ligation-induced (SNL model) neuropathic pain can be produced using the procedure originally described in Kim, S. H. and J. M. Chung, 1992, An experimental model for peripheral neuropathy produced by segmental spinal nerve ligation in the rat, Pain, 50, 355. The left L5 and L6 spinal nerves of the rat are isolated adjacent to the vertebral column and tightly ligated with a 5-0 silk suture distal to the DRG, and care is taken to avoid injury of the L4 spinal nerve. Sham rats undergo the same procedure, but without nerve ligation. All animals are allowed to recover for at least one week and not more than three weeks prior to assessment of tactile allodynia.

Tactile allodynia is measured using calibrated von Frey filaments (Stoelting, Wood Dale, Ill.) as described in Chaplan, S. R., F. W. Bach, J. W. Porgrel, J. M. Chung and T. L. Yaksh, 1994, Quantitative assessment of tactile allodynia in the rat paw, J. Neurosci. Methods, 53, 55. Rats are placed into inverted individual plastic containers (20×12.5×20 cm) on top of a suspended wire mesh grid, and are acclimated to the test chambers for 20 minutes. The von Frey filaments are presented perpendicularly to the plantar surface of the selected hind paw, and are then held in this position for approximately 8 sec with enough force to cause a slight bend in the filament. Positive responses include an abrupt withdrawal of the hind paw from the stimulus, or flinching behavior immediately following removal of the stimulus. A 50% withdrawal threshold is determined using an up-down procedure as described in Dixon, W. J., 1980, Efficient analysis of experimental observations, Ann. Rev. Pharmacol. Toxicol., 20, 441). Only rats with a baseline threshold score of less that 4.25 g are used in this study, and animals demonstrating motor deficit are excluded. Tactile allodynia thresholds are also assessed in several control groups, including naive, sham-operated, and saline infused animals as well as in the contralateral paws of nerve-injured rats.

Capsaicin-Induced Secondary Mechanical Hypersensitivity:

Rats were allowed to acclimate to the study room for 1 hour. They were then briefly restrained, and capsaicin was administered at 10 µg in 10 µL of vehicle (10% ethanol and 2-hydroxypropyl cyclodextrin) by intraplantar injection into the center of the right hind paw. Secondary mechanical hyperalgesia was measured at the heel away from the site of injection at 180 min following capsaicin (Joshi et al 2006, Neuroscience 143, 587-596). Compounds are injected (i.p.) 30 min before testing (150 min post-capsaicin).

Tactile allodynia was measured as described above.

Certain compound of the present invention showed a statistically significant change in paw withdrawal latency versus a saline vehicle at less than about 300 micromoles/kg. In a more preferred embodiment, compound of the present invention showed efficacy of less than about 50 micromoles/kg.

D. METHODS OF USING THE COMPOUNDS

The data contained herein above demonstrates that compounds of the present invention bind to the $CB_2$ receptor. Certain compounds of the present invention were shown to have an analgesic effect in animal pain models relating to neuropathic and/or nociceptive pain.

One embodiment of the present invention provides a method for treating pain (for example, neuropathic pain or nociceptive pain) in a mammal in need of such treatment. The method comprises administering to the mammal a therapeutically effective amount of a compound of formula (I), or a pharmaceutically acceptable salt thereof.

Another embodiment of the present invention provides a method for treating a disorder selected from the group consisting of inflammatory disorders, immune disorders, neurological disorders, cancers of the immune system, respiratory disorders, and cardiovascular disorders in a mammal in need of such treatment. The method comprises administering to the mammal a therapeutically effective amount of a compound of formula (I), or a pharmaceutically acceptable salt thereof.

Yet another embodiment of the present invention relates to a method for providing neuroprotection in a mammal in need of such treatment. This method comprises administering to the mammal a therapeutically effective amount of a compound of formula (I), or a pharmaceutically acceptable salt thereof.

In addition to the data contained herein, several lines of evidence support the assertion that $CB_2$ receptors play a role in analgesia. For example, Zimmer et al. have reported that the nonselective cannabinoid agonist $\Delta^9$-THC retains some analgesic efficacy in $CB_1$ receptor knockout mice (Zimmer, A., et al., Proc. Nat. Acad. Sci., 1999, 96, 5780-5785). HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabinoid ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260). The analgesic effects induced by these $CB_2$-selective ligands are blocked by $CB_2$ and not by $CB_1$ receptor antagonists. Furthermore, at fully efficacious doses, AM-1241 and GW405833 are devoid of typical $CB_1$ receptor-mediated CNS side effects, providing evidence that modulation of $CB_2$ receptors can produce broad-spectrum pain relief with reduced side-effect liability.

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators are useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. They are quiescent and resting having a ramified morphology as long as the CNS is healthy. Microglia expresses a variety of receptors enabling them to survey the CNS and respond to pathological events. Insult or injury to the CNS leads to microglial cell activation, which is characterized by various morphological changes allowing response to the lesion. Ramifications are retracted and microglia are transformed into amoeboid-like cells with phagocytic function. They can proliferate, rapidly migrate to the site of injury, and produce and release cytokines, chemokines and complement components (Watkins L. R., et al., Trends in Neuroscience, 2001, 24(8), 450; Kreutzberg, G. W., Trends in Neuroscience, 1996, 19, 312-318). $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system. It is conceivable that $CB_2$ receptors may be more susceptible to pharmacological effects during neuroinflammation (Walter, L., Stella, N., Br. J. Pharmacol. 2004, 141, 775-785). Neuroinflammation occurs in several neurodegenerative diseases, and induction of microglial $CB_2$ receptors has been observed (Carrier, E. J., et al., Current Drug Targets —CNS & Neurological Disorders, 2005, 4, 657-665). Thus, $CB_2$ ligands may be clinically useful for the treatment of neuroinflammation.

$CB_2$ receptor expression has been detected in perivascular microglial cells within normal, healthy human cerebellum (Nunez, E., et al., Synapse, 2004, 58, 208-213). Perivascular cells are immunoregulatory cells located adjacent to CNS blood vessels and, along with parenchymal microglia and astrocytes, they play a pivotal role in maintaining CNS homeostasis and blood-brain barrier functionality (Williams, K., et al., Glia, 2001, 36, 156-164). $CB_2$ receptor expression has also been detected on cerebromicrovascular endothelial cells, which represent a main component of the blood-brain barrier (Golech, S. A., et al., Mol. Brain. Res., 2004, 132, 87-92). A recent report demonstrated that $CB_2$ receptor expression is up-regulated in the brains of macaques with simian immunodeficiency virus-induced encephalitis (Benito, C., et al., J. Neurosci. 2005, 25(10), 2530-2536). Thus, compounds that affect $CB_2$ signaling may protect the blood-brain barrier and be clinically useful in the treatment of neuroinflammation and a variety of neuroinflammatory disorders including retroviral encephalitis, which occurs with human immunodeficiency virus (HIV) infection in the CNS.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators represents a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu. Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators represents a unique approach for the treatment of liver fibrosis.

$CB_2$ receptors are involved in the neuroprotective and anti-inflammatory mechanisms induced by the interleukin-1 receptor antagonist (IL-1ra) (Molina-Holgado, F., et al., J. Neurosci., 2003, 23(16), 6470-6474). IL-1ra is an important anti-inflammatory cytokine that protects against ischemic, excitotoxic, and traumatic brain insults. $CB_2$ receptors play a role in mediating these neuroprotective effects indicating that $CB_2$ ligands are useful in the treatment of traumatic brain injury, stroke, and in mitigating brain damage.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators have utility as antitussive agents for the treatment of pulmonary inflammation, chronic cough, and a variety of airway inflammatory diseases including but not limited to asthma, chronic obstructive pulmonary disease, and pulmonary fibrosis.

Osteoporosis is a disease characterized by reduced bone mass, which leads to deterioration of bone microstructure and increased susceptibility to fracture. Age is associated with bone loss and it is estimated that 50% of all Caucasian women will have osteoporosis by the age of 80 (Ralston, S. H., Curr. Opin. Pharmacol., 2003, 3, 286-290). There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators are useful for the treatment and prevention of osteoporosis, osteoarthritis, and bone disorders.

Atherosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor are clinically useful for the treatment of atherosclorsis.

$CB_2$ receptors are expressed on malignant cells of the immune system and targeting $CB_2$ receptors to induce apoptosis may constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ modulators have utility as anticancer agents against tumors of immune origin.

Activation of $CB_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, $CB_2$ modulators have utility for the treatment or prophylaxis of cardiovascular disease and the development of myocardial infarction.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the invention can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.1 mg/kg body weight to about 100 mg/kg body weight. More preferable doses can be in the range of from about 0.3 mg/kg body weight to about 30 mg/kg body weight. If desired, the effective daily dose can be divided into multiple doses for purposes of administration. Consequently, single dose compositions may contain such amounts or submultiples thereof to make up the daily dose.

E. PHARMACEUTICAL COMPOSITIONS

The present invention further provides pharmaceutical compositions that comprise compounds of the present invention or a pharmaceutically acceptable salt or solvate thereof. The pharmaceutical compositions comprise compounds of the present invention that may be formulated together with one or more non-toxic pharmaceutically acceptable carriers.

Another aspect of the present invention is a pharmaceutical composition comprising a compound of formula (I), or a pharmaceutically acceptable salt thereof, and one or more pharmaceutically acceptable carriers, alone or in combination with one or more nonsteroidal anti-inflammatory drug (NSAID).

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

F. GENERAL SYNTHESIS

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention may be prepared by a variety of processes well known for the preparation of compounds of this class. For example, the compounds of the invention wherein the groups $R_1$, $R_2$, $R_3$, $R_4$, $R_5$, $R_6$, and X have the meanings as set forth in the summary section unless otherwise noted, can be synthesized as shown in Schemes 1-6.

Compounds of the invention were named by ACD/ChemSketch version 5.01 (developed by Advanced Chemistry Development, Inc., Toronto, ON, Canada) or were given names consistent with ACD nomenclature.

As used in the descriptions of the schemes and the examples, certain abbreviations are intended to have the following meanings: DMA for dimethylacetamide, DMAP for 4-(dimethylamino)pyridine, DMF for N,N-dimethylformamide, DMSO for dimethyl sulfoxide, EDCI for 1-(3-dimethylaminopropyl)-3-ethylcarbodiimide hydrochloride, EtOAc for ethyl acetate, $CHCl_3$ for chloroform, $CH_2Cl_2$ for dichloromethane, $CH_3CN$ for acetonitrile, HOBt for 1-hydroxybenzotriazole hydrate, HPLC for high performance liquid chromatography, MeOH for methanol, PS-BEMP for polymer bound 2-tert-butylimino-2-diethylamino-1,3-dimethyl-perhydro-1,3,2-diazaphosphorine, and THF for tetrahydrofuran.

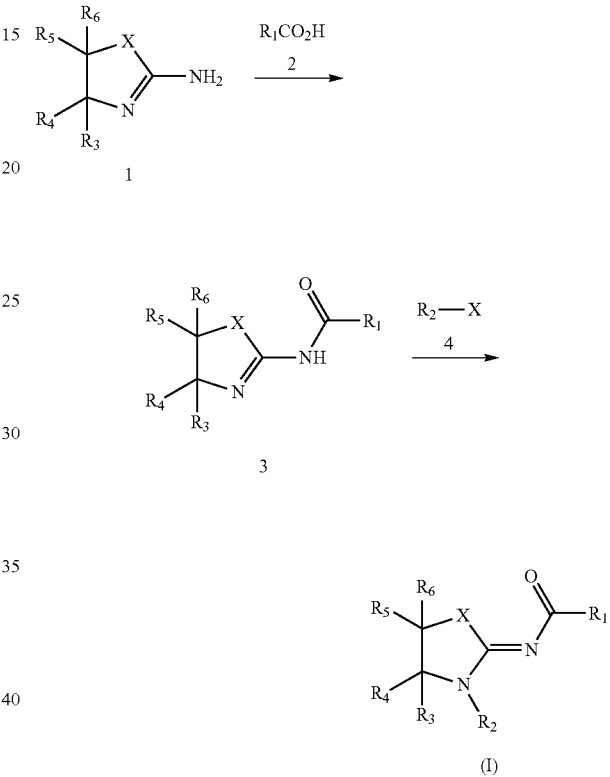

Compounds of formula (I) can be prepared utilizing general procedures as shown in Scheme 1. Compounds of formula 1 when treated with compounds of formula 2, in the presence of an acid coupling reagent, a base such as triethylamine, and optionally an auxiliary reagent provide compounds of formula 3. Examples of the acid coupling reagent include, but are not limited to, 1-(3-dimethylaminopropyl)-3-ethylcarbodiimide hydrochloride (EDCI), 1,3-dicyclohexylcarbodiimide (DCC), bis(2-oxo-3-oxazolidinyl)phosphinic chloride (BOPCl), O-(7-azabenzotriazol-1-yl)-N,N,N',N'-tetramethyluronium hexafluorophosphate (HATU), and O-benzotriazol-1-yl-N,N,N',N'-tetramethyluronium tetrafluoroborate (TBTU). Suitable auxiliary reagents include, but not limited to 1-hydroxy-7-azabenzotriazole (HOAT) and 1-hydroxybenzotriazole hydrate (HOBT). The reaction is generally conducted in a solvent such as, but not limited to, tetrahydrofuran or dichloromethane. Compounds of formula 3 when treated with a base such as sodium hydride, potassium tert-butoxide, lithium diisopropylamide or lithium bis(trimethylsilyl)amide, in a solvent such as but not limited to THF, DMF or mixtures thereof, followed by the addition of compounds of formula 4, wherein X is chloro, bromo, iodo, mesyl, or tosyl, will provide compounds of formula (I).

Scheme 2

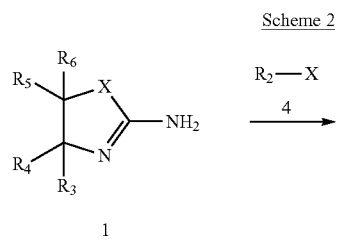

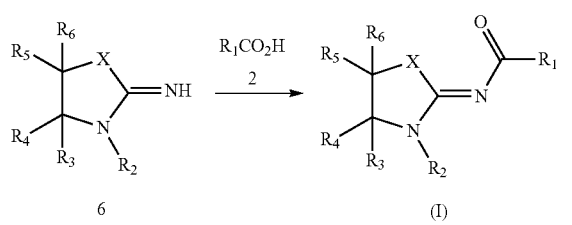

Alternatively, compounds of formula (I) may be prepared as described in Scheme 2. Compounds of formula 1 when treated with a base such as sodium hydride, potassium tert-butoxide, lithium diisopropylamide or lithium bis(trimethylsilyl)amide, in a solvent such as but not limited to THF, DMF or mixtures thereof, followed by the addition of compounds of formula 4, wherein X is chloro, bromo, iodo, mesyl, or tosyl will provide compounds of formula 6. The further treatment of compounds of formula 6 with compounds of formula 2 using methodology as outlined in Scheme 1 for the conversion of 1 to 3, will provide compounds of formula (I).

Scheme 3

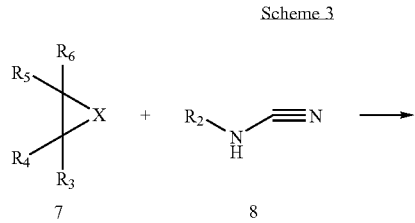

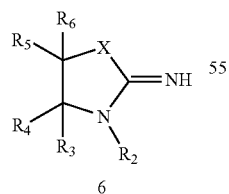

Intermediates of formula 6 can be prepared using general procedure as outlined in Scheme 3. Compounds of formula 7 when treated with compounds of formula 8 in the presence of potassium carbonate at a temperature ranging from about 25° C. to about 100° C., in a solvent such as methyl ethyl ketone, provide compounds of formula 6.

Scheme 4

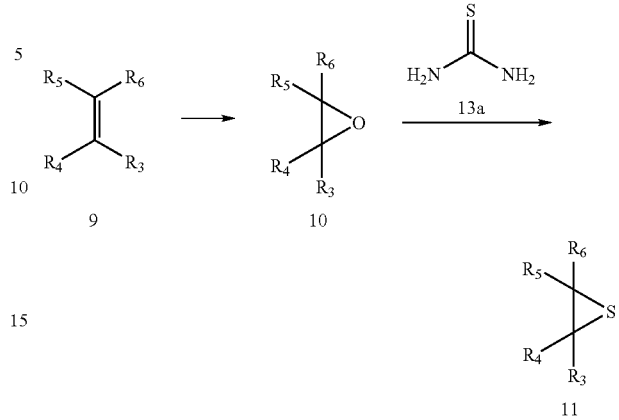

Compounds of formula 7 wherein X is S, may be prepared according to the procedure outlined in Scheme 4. Compounds of formula 9 when treated with meta-chloroperbenzoic acid in dichloromethane provide compounds of formula 10. Compounds of formula 10 when treated with compounds of formula 13a under heated conditions in a solvent such as methanol provide compounds of formula 11.

Scheme 5

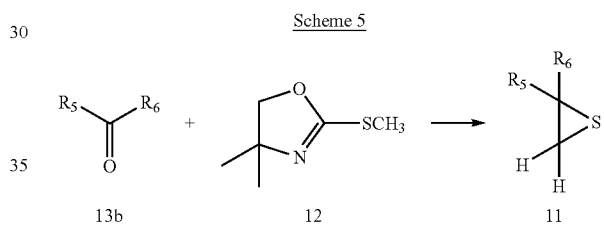

Alternatively, compounds of formula 7 wherein X is S, may be prepared according to the procedures outlined in Scheme 5. Compounds of formula 13b when treated with compounds of formula 12 (prepared according to the procedure outlined in Meyers, A. I.; Ford, Michael E., *J. Org. Chem.* 1976, 41, 1735-1742) which has been pretreated with lithium diisopropylamide in THF under nitrogen, at a temperature between about −10° C. and about −78° C. will provide compounds of formula 11.

Scheme 6

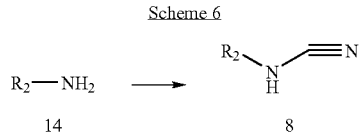

As shown in Scheme 6, intermediates of formula 8 may be prepared accordingly. Compounds of formula 14 when treated with cyanogen-bromide in the presence of sodium carbonate in ether will provide compounds of formula 8.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

Following Examples may be used for illustrative purposes and should not be deemed to narrow the scope of the invention.

G. EXAMPLES

Example 1

5-chloro-2-methoxy-N-[(2Z)-3-(2-methoxyethyl)-5,5-dimethyl-1,3-thiazolidin-2-ylidene]benzamide

Example 1A

Z-5-chloro-N-(5,5-dimethyl-4,5-dihydrothiazol-2-yl)-2-methoxybenzamide

A mixture of 5,5-dimethyl-4,5-dihydrothiazol-2-ylamine hydrochloride (250 mg, 1.50 mmol) (Bruson, H and Eastes, J. *J. Am. Chem. Soc.* 1937, 59, 2011), 5-chloro-2-methoxybenzoic acid (280 mg, 1.50 mmol), EDCI (287 mg, 1.50 mmol), HOBt (203 mg, 1.50 mmol) and triethylamine (210 μL, 1.50 mmol) in tetrahydrofuran (6 mL) was stirred at room temperature for 1 hour. The mixture was concentrated and extracted with ethyl acetate (2×30 mL). The combined organic layers were dried over $Na_2SO_4$, filtered, concentrated under reduced pressure and the residue purified by flash chromatography (silica gel, eluting with ethyl acetate/hexanes 1:1) to provide 400 mg of the title product. MS ($ESI^+$) m/z 299 $(M+H)^+$.

Example 1B 5-chloro-2-methoxy-N-[(2Z)-3-(2-methoxyethyl)-5,5-dimethyl-1,3-thiazolidin-2-ylidene]benzamide To a solution of Example 1A (398 mg, 1.33 mmol) in THF/DMF (2/1) (8 mL) was added sodium hydride (60% oil dispersion) (66.0 mg, 1.73 mmol) and the mixture was stirred at room temperature for 20 minutes. 2-Bromoethyl methyl ether (222 mg, 1.60 mmol) was added and the mixture was stirred at 70° C. for 12 hours. The mixture was cooled to room temperature diluted with ethyl acetate and washed with brine. The organic extract was dried over $MgSO_4$, filtered, concentrated under reduced pressure and purified by flash chromatography (silica gel, eluting with ethyl acetate/hexanes 1:1) to provide 235 mg of the title product. MS ($ESI^+$) m/z 357 (M+H); $^1$H NMR (300 MHz, DMSO-$d_6$) δ ppm 1.45 (s, 6H) 3.28 (s, 3H) 3.59 (t, J=5.3 Hz, 2H) 3.58 (s, 2H) 3.77 (s, 3H) 3.80 (t, J=5.3 Hz, 2H) 7.09 (d, J=8.8 Hz, 1H) 7.44 (dd, J=8.8, 2.7 Hz, 1H) 7.62 (d, J=3.1 Hz, 1H).

Example 2

N-[(2Z)-3-butyl-5,5-dimethyl-1,3-thiazolidin-2-ylidene]-5-chloro-2-methoxybenzamide

Example 2A 3-butyl-5,5-dimethylthiazolidin-2-imine

A mixture of 2,2-dimethyl-thiirane (TCI) (1.5 g, 17 mmol), N-butyl-cyanamide (1.7 g, 17 mmol) (prepared as described in Ross *J. Med. Chem.* 1979, 22; 412) and potassium carbonate (2.4 g, 17 mmol) in 2-butanone (15 mL) was heated to 80° C. overnight. The mixture was poured into water, and extracted with ethyl acetate (2×). The combined organic extracts were dried over $Na_2SO_4$, filtered, concentrated under reduced pressure to afford 2.11 g of the title compound.

Example 2B

N-[(2Z)-3-butyl-5,5-dimethyl-1,3-thiazolidin-2-ylidene]-5-chloro-2-methoxybenzamide A mixture of the compound from Example 2A (1.2 g, 6.4 mmol), 5-chloro-2-methoxy-benzoic acid (1.4 g, 7.7 mmol), EDCI (2.45 g, 12.8 mmol), HOBt (1.7 g, 12.8 mmol) and DMAP (78 mg, 0.64 mmol) in pyridine (40 mL) was stirred at room temperature for 1 hour. The mixture was concentrated under reduced pressure, diluted with water, and extracted with ethyl acetate (3×30 mL). The combined organic layers were dried over $MgSO_4$, filtered and concentrated under reduced pressure. The residue was purified by flash chromatography (silica gel, eluting with ethyl acetate/hexanes 1:3) to provide 919 mg of title compound. MS (APCI) m/z 355

(M+H)+; 1H NMR (400 MHz, DMSO-d6) δ ppm 0.92 (t, J=7.4 Hz, 3H) 1.31 (m, 2H) 1.45 (s, 6H) 1.60 (m, 2H) 3.53 (m, 2H) 3.63 (t, J=7.4 Hz, 2H) 3.77 (s, 3H) 7.09 (d, J=8.9 Hz, 1H) 7.45 (dd, J=8.9, 2.8 Hz, 1H) 7.64 (d, J=2.8 Hz, 1H).

Example 3

N-[(2Z)-3-butyl-5-tert-butyl-1,3-thiazolidin-2-ylidene]-5-chloro-2-methoxybenzamide

Example 3A 2-tert-butylthiirane

A mixture of 2-tert-butyl-oxirane (Lancaster) (860 mg 10 mmol) and thiourea (760 mg, 10 mmol) in MeOH (10 mL) was heated at 80° C. for 12 hours. The mixture was poured into water, and extracted with ether (2×). The combined organic layers were dried over MgSO4, filtered and concentrated to afford the title product.

Example 3B 5-tert-butyl-3-butylthiazolidin-2-imine

The title compound was prepared using the procedure as described in Example 2A substituting the compound from Example 3A for 2,2-dimethyl-thiirane.

Example 3C

N-[(2Z)-3-butyl-5-tert-butyl-1,3-thiazolidin-2-ylidene]-5-chloro-2-methoxybenzamide The title compound was obtained according to the procedure outlined in Example 2B by substituting the compound from Example 3B for the compound from Example 2A. 1H NMR (500 MHz, CDCl3) δ ppm 0.98 (t, J=7.3 Hz, 3H) 1.02 (s, 9H) 1.39 (m, 2H) 1.65 (m, 2H) 3.48 (m, 2H) 3.63 (m, 2H) 3.73 (m, 1H) 3.88 (s, 3H) 6.88 (d, J=8.9 Hz, 1H) 7.32 (dd, J=8.9, 2.8 Hz, 1H) 7.99 (d, J=2.8 Hz, 1H); MS (DCI/NH3) m/z 383 (M+H)+

Example 4

N-[(2Z)-3-butyl-5-tert-butyl-1,3-thiazolidin-2-ylidene]-4-chloro-2-methoxybenzamide The title compound was obtained according to the procedure outlined in Example 2B by substituting Example 3B for Example 2A and 4-chloro-2-methoxy-benzoic acid (Aldrich) for 5-chloro-2-methoxy-benzoic acid. MS (DCI/NH3) m/z 383 (M+H)+; 1H NMR (500 MHz, CDCl3) δ ppm 0.96 (t, J=7.3 Hz, 3H) 1.02 (s, 9H) 1.37 (m, 2H) 1.63 (m, 2H) 3.47 (m, 2H) 3.62 (m, 2H) 3.72 (m, 1H) 3.89 (s, 3H) 6.93 (m, 2H) 8.00 (d, J=8.9 Hz, 1H).

Example 5

4-bromo-N-[(2Z)-3-butyl-5-tert-butyl-1,3-thiazolidin-2-ylidene]-2-methoxybenzamide The title compound was obtained according to the procedure outlined in Example 2B by substituting Example 3B for Example 2A and 4-bromo-2-methoxy-benzoic acid (Apin) for 5-chloro-2-methoxy-benzoic acid. 1H NMR (500 MHz, CDCl3) δ ppm 0.96 (t, J=7.32 Hz, 3H) 1.01 (s, 9H) 1.38 (m, 2H) 3.47 (m, 2H) 3.61 (m, 2H) 3.72 (m, 1H) 3.88 (s, 3H) 7.08 (s, 1H) 7.09 (dd, J=6.1, 1.8 Hz, 1H) 7.92 (d, J=8.9 Hz, 1H); MS (DCI/NH3) m/z 427 (M+H)+.

Example 6

N-[(2Z)-3-butyl-5-tert-butyl-1,3-thiazolidin-2-ylidene]-5-chloro-2-(trifluoromethoxy)benzamide

Example 6A 5-chloro-2-(trifluoromethoxy)benzoic Acid

A 1.6 M solution of butyllithium in hexanes (26.5 mmol, 16.5 mL) was added to a 0° C. solution of diisopropylamine (2.65 g, 26.5 mmol) in tetrahydrofuran (50 mL). The solution was cooled to −100° C., and 1-chloro-4-(trifluoromethoxy)benzene (Matrix) (5.0 g, 26.5 mmol) was added. After 2 h at −100° C., the mixture was poured onto an excess of freshly crushed dry ice. After evaporation of the volatiles, the residue was dissolved in a 1 M aqueous solution (50 mL) of sodium hydroxide, washed with diethyl ether (2×15 mL), and acidified to pH 1 by the addition of concentrated hydrochloric acid (7 mL). The aqueous layers were extracted with diethyl ether (3×30 mL). The combined organic extracts were dried (MgSO4), filtered and concentrated to afford the title product. 1H NMR (300 MHz, DMSO-d6) δ ppm 7.54 (dd, J=8.8, 1.0 Hz, 1H) 7.78 (dd, J=8.8, 2.7 Hz, 1H) 7.92 (d, J=2.7 Hz, 1H).

Example 6B

N-[(2Z)-3-butyl-5-tert-butyl-1,3-thiazolidin-2-ylidene]-5-chloro-2-(trifluoromethoxy)benzamide The title compound was obtained according to the procedure outlined in Example 2B by substituting Example 3B for Example 2A and Example 6A for 5-chloro-2-methoxy-benzoic acid. MS (DCI/NH3) m/z 437 (M+H)+; 1H NMR (500 MHz, CDCl3) δ ppm 0.96 (t, J=7.3 Hz, 3H) 1.02 (s, 9H) 1.36 (m, 2H) 3.52 (m, 2H) 3.65 (m, 2H) 3.72 (m, 1H) 7.21 (dd, J=8.9, 0.9 Hz, 1H) 7.39 (dd, J=8.9, 2.8 Hz, 1H) 8.02 (d, J=2.8 Hz, 1H).

Example 7

N-[(2Z)-3-butyl-5-propyl-1,3-thiazolidin-2-ylidene]-5-chloro-2-methoxybenzamide

Example 7A 2-propylthiirane

The title compound was prepared using the procedure as described in Example 3A substituting 2-propyl-oxirane for 2-tert-butyl-oxirane.

Example 7B 3-butyl-5-propylthiazolidin-2-imine

The title compound was prepared using the procedure as described in Example 2A substituting Example 7A for 2,2-dimethyl-thiirane.

Example 7C

N-[(2Z)-3-butyl-5-propyl-1,3-thiazolidin-2-ylidene]-5-chloro-2-methoxybenzamide

The title compound was obtained according to the procedure outlined in Example 2B by substituting Example 7B for Example 2A. MS (DCI/NH$_3$) m/z 369 (M+H)$^+$; $^1$H NMR (500 MHz, CDCl$_3$) ppm 0.94 (t, J=7.3 Hz, 3H) 0.98 (t, J=7.3 Hz, 3H) 1.34-1.43 (m, 2H) 1.43-1.52 (m, 2H) 1.60-1.67 (m, 2H) 1.66-1.73 (m, 2H) 3.35 (dd, J=10.7, 6.41 Hz, 1H) 3.49-3.58 (m, 1H) 3.64-3.73 (m, 2H) 3.74 (dd, J=10.7, 7.9 Hz, 1H) 3.85-3.90 (m, 3H) 6.88 (d, J=8.9 Hz, 1H) 7.32 (dd, J=8.9, 2.75 Hz, 1H) 7.98 (d, J=2.8 Hz, 1H).

Example 8

N-[(2Z)-3-butyl-5-ethyl-5-methyl-1,3-thiazolidin-2-ylidene]-5-chloro-2-methoxybenzamide

Example 8A 2-ethyl-2-methylthiirane

The title compound was prepared using the procedure as described in Example 3A substituting 2-ethyl-2-methyl-oxirane for 2-tert-butyl-oxirane.

Example 8B 3-butyl-5-ethyl-5-methylthiazolidin-2-imine

The title compound was prepared using the procedure described in Example 2A substituting Example 8A for 2,2-dimethyl-thiirane.

Example 8C

N-[(2Z)-3-butyl-5-ethyl-5-methyl-1,3-thiazolidin-2-ylidene]-5-chloro-2-methoxybenzamide The title compound was obtained according to the procedure outlined in Example 2B by substituting Example 8B for Example 2A. MS (DCI/NH$_3$) m/z 369 (M+H)$^+$; $^1$H NMR (500 MHz, CDCl$_3$) δ ppm 0.98 (t, J=7.6 Hz, 3H) 1.03 (t, J=7.3 Hz, 3H) 1.35-1.44 (m, 2H) 1.45-1.49 (m, 3H) 1.60-1.69 (m, 2H) 1.69-1.87 (m, 2H) 3.40 (dd, J=48.21, 10.7 Hz, 2H) 3.62-3.76 (m, 2H) 3.84-3.90 (m, 3H) 6.87 (d, J=8.9 Hz, 1H) 7.32 (dd, J=8.9, 3.1 Hz, 1H) 7.98 (d, J=2.75 Hz, 1H).

Example 9

N-[(2Z)-3-butyl-5-methyl-1,3-thiazolidin-2-ylidene]-5-chloro-2-methoxybenzamide

Example 9A 3-butyl-5-methylthiazolidin-2-imine

The title compound was prepared using the procedure described in Example 2A substituting 2-methyl-thiirane for 2,2-dimethyl-thiirane.

Example 9B

N-[(2Z)-3-butyl-5-methyl-1,3-thiazolidin-2-ylidene]-5-chloro-2-methoxybenzamide

The title compound was obtained according to the procedure outlined in Example 2B by substituting Example 9A for Example 2A. MS (DCI/NH$_3$) m/z 341 (M+H)$^+$; $^1$H NMR (500 MHz, CDCl$_3$) δ ppm 0.98 (t, J=7.3 Hz, 3H) 1.35-1.42 (m, 2H) 1.43 (d, J=6.7 Hz, 3H) 1.65 (m, 2H) 3.30 (dd, J=11.0, 6.1 Hz, 1H) 3.57-3.79 (m, 4H) 3.88 (s, 3H) 6.88 (d, J=8.9 Hz, 1H) 7.32 (dd, J=8.9, 2.8 Hz, 1H) 7.98 (d, J=2.8 Hz, 1H).

Example 10

N-[(2Z)-3-butyl-5-(4-fluorophenyl)-1,3-thiazolidin-2-ylidene]-5-chloro-2-methoxybenzamide

Example 10A 2-(4-Fluoro-phenyl)-thiirane

A mixture of 2-(4-fluoro-phenyl)-oxirane (1.38 g, 10.0 mmol), thiourea (760 mg, 10.0 mmol) and silica gel (200 mg) in CH$_2$Cl$_2$ (10 mL) was stirred at room temperature for 12 hours. Water (20 mL) was added to the suspension and the mixture was extracted with CH$_2$Cl$_2$ (2×20 mL). The combined organic layers were dried over MgSO$_4$, filtered and concentrated to provide the title product.

Example 10B

3-Butyl-5-(4-fluoro-phenyl)-thiazolidin-2-ylidene-amine

The title compound was prepared using the procedure described in Example 2A substituting Example 10A for 2,2-dimethyl-thiirane.

Example 10C

N-[(2Z)-3-butyl-5-(4-fluorophenyl)-1,3-thiazolidin-2-ylidene]-5-chloro-2-methoxybenzamide The title compound was obtained according to the procedure outlined in Example 2B by substituting Example 10B for Example 2A. $^1$H NMR (500 MHz, CDCl$_3$) δ ppm 0.99 (t, J=7.3 Hz, 3H) 1.41 (m, 2H) 1.66 (m, 2H) 3.65 (dd, J=11.3, 7.3 Hz, 1H) 3.75 (m, 2H) 3.89 (s, 3H) 3.99 (dd, J=11.0, 8.24 Hz, 1H) 4.69 (t, J=7.9 Hz, 1H) 6.89 (d, J=8.9 Hz, 1H) 7.04 (t, J=8.5 Hz, 2H) 7.36 (m, 3H) 8.03 (d, J=2.8 Hz, 1H); MS (DCI/NH$_3$) m/z 421 (M+H)$^+$.

Example 11

N-[(2Z)-3-butyl-5-tert-butyl-5-methyl-1,3-thiazolidin-2-ylidene]-5-chloro-2-methoxybenzamide

Example 11A 2-tert-Butyl-2-methyl-oxirane

To a solution of 2,3,3-trimethyl-but-1-ene (5.0 g, 51 mmol) in CH$_2$Cl$_2$ (200 mL) was added drop wise a solution of 3-chloroperbenzoic acid (13.7 g, 61 mmol) in CH$_2$Cl$_2$ (100 mL). The mixture was stirred for 16 hours at room temperature then diluted with saturated Na$_2$SO$_3$ (100 mL). The layers were separated and the organic phase was washed with saturated Na$_2$CO$_3$ (100 mL) then water. The separated organic extract was dried over MgSO$_4$ filtered and concentrated to provide the desired product. $^1$H NMR (500 MHz, CDCl$_3$) δ ppm 0.95 (s, 9H) 1.29 (s, 3H) 2.43 (d, J=4.6 Hz, 1H) 2.80 (d, J=4.9 Hz, 1H)

Example 11B 2-tert-Butyl-2-methyl-thiirane

The title compound was prepared using the procedure as described in Example 3A substituting the product from Example 11A for 2-tert-butyl-oxirane.

Example 11C

3-Butyl-5-tert-butyl-5-methyl-thiazolidin-2-ylidene-amine

The title compound was prepared using the procedure described in Example 2A substituting Example 11B for 2,2-dimethyl-thiirane.

Example 11D

N-[(2Z)-3-butyl-5-tert-butyl-5-methyl-1,3-thiazolidin-2-ylidene]-5-chloro-2-methoxybenzamide The title compound was obtained according to the procedure outlined in Example 2B by substituting Example 11C for Example 2A. MS (DCI/NH$_3$) m/z 397 (M+H)$^+$; $^1$H NMR (500 MHz, CDCl$_3$) δ ppm 0.99 (t, J=7.3 Hz, 3H) 1.07 (s, 9H) 1.41 (m, 2H) 1.52 (s, 3H) 1.66 (m, 2H) 3.18 (d, J=11.3 Hz, 1H) 3.60 (m, 1H) 3.70 (d, J=11.3 Hz, 1H) 3.81 (dt, J=13.4, 7.6 Hz, 1H) 3.87 (s, 3H) 6.87 (d, J=8.9 Hz, 1H) 7.31 (dd, J=8.9, 2.8 Hz, 1H) 7.99 (d, J=2.8 Hz, 1H).

Example 12

N-[(2Z)-3-butyl-5-tert-butyl-5-methyl-1,3-thiazolidin-2-ylidene]-4-chloro-2-methoxybenzamide The title compound was obtained according to the procedure outlined in Example 2B by substituting Example 11C for Example 2A and 4-chloro-2-methoxy-benzoic acid for 5-chloro-2-methoxy-benzoic acid. MS (DCI/NH$_3$) m/z 397 (M+H)$^+$; $^1$H NMR (500 MHz, CDCl$_3$) δ ppm 0.97 (t, J=7.3 Hz, 3H) 1.07 (s, 9H) 1.39 (m, 2H) 1.52 (s, 3H) 1.65 (m, 2H) 3.16 (d, J=11.3 Hz, 1H) 3.58 (dt, J=13.4, 7.3 Hz, 1H) 3.69 (d, J=11.3 Hz, 1H) 3.80 (dt, J=13.4, 7.6 Hz, 1H) 3.89 (s, 3H) 6.94 (m, 2H) 7.99 (d, J=8.9 Hz, 1H).

Example 13

4-bromo-N-[(2Z)-3-butyl-5-methyl-1,3-thiazolidin-2-ylidene]-2-methoxybenzamide

The title compound was obtained according to the procedure outlined in Example 2B by substituting Example 9A for Example 2A and 4-bromo-2-methoxy-benzoic acid for 5-chloro-2-methoxy-benzoic acid. MS (DCI/NH$_3$) m/z 385 (M+H)$^+$; $^1$H NMR (500 MHz, CDCl$_3$) δ ppm 0.96 (t, J=7.3 Hz, 3H) 1.37 (m, 2H) 1.42 (d, J=6.7 Hz, 3H) 1.63 (m, 2H) 3.29 (dd, J=10.7, 5.80 Hz, 1H) 3.67 (m, 4H) 3.88 (s, 3H) 7.08 (s 1H) 7.10 (d, J=1.8 Hz, 1H) 7.91 (d, J=8.2 Hz, 1H).

Example 14

N-[(2Z)-3-butyl-5-methyl-1,3-thiazolidin-2-ylidene]-6-chloroquinoline-8-carboxamide The title compound was obtained according to the procedure outlined in Example 2B by substituting Example 9A for Example 2A and 6-chloro-quinoline-8-carboxylic acid (Weyer et al, *Arzneim. Forsch* 1974, 24, 269) for 5-chloro-2-methoxy-benzoic acid. MS (DCI/NH$_3$) m/z 362 (M+H)$^+$; $^1$H NMR (500 MHz, CDCl$_3$) δ ppm 0.95 (t, J=7.3 Hz, 3H) 1.37 (m, 2H) 1.47 (d, J=6.71 Hz, 3H) 1.65 (m, 2H) 3.34 (dd, J=10.7, 6.10 Hz, 1H) 3.70 (m, 3H) 3.79 (dd, J=10.7, 7.6 Hz, 1H) 7.40 (dd, J=8.5, 4.3 Hz, 1H) 7.82 (d, J=2.4 Hz, 1H) 8.04 (d, J=2.4 Hz, 1H) 8.06 (dd, J=8.2, 1.8 Hz, 1H) 9.02 (dd, J=4.3, 1.8 Hz, 1H).

Example 15

N-[(2Z)-3-butyl-1-thia-3-azaspiro[4.4]non-2-ylidene]-5-chloro-2-methoxybenzamide

Example 15A

1-Oxa-spiro[2.4]heptane

The title compound was prepared using the procedure as described in Example 11A substituting methylene-cyclopentane (Aldrich) for 2,3,3-trimethyl-but-1-ene.

Example 15B

1-Thia-spiro[2.4]heptane

A mixture of Example 15A (1.0 g, 10 mmol) and thiourea (760 mg, 10 mmol) in H$_2$O (20 mL) was stirred at room temperature for 12 hours. The mixture was extracted with CH$_2$Cl$_2$ (2×). The combined organic layers were dried over MgSO$_4$, filtered and concentrated to afford the title product.

Example 15C 3-butyl-1-thia-3-aza spiro[4.4]non-2-ylideneamine

The title compound was prepared according to the procedure outlined in Example 2A substituting Example 15B for 2,2-dimethyl-thiirane.

Example 15D

N-[(2Z)-3-butyl-1-thia-3-azaspiro[4.4]non-2-ylidene]-5-chloro-2-methoxybenzamide The title compound was obtained according to the procedure outlined in Example 2B by substituting Example 15C for Example 2A. MS (DCI/NH$_3$) m/z 381 (M+H)$^+$; $^1$H NMR (500 MHz, CDCl$_3$) δ ppm 0.98 (t, J=7.6 Hz, 3H) 1.40 (m, 2H) 1.65 (m, 2H) 1.85 (m, 4H) 2.07 (m, 2H) 3.51 (m, 2H) 3.71 (t, J=7.3 Hz, 2H) 3.87 (s, 3H) 6.87 (d, J=8.9 Hz, 1H) 7.32 (dd, J=8.9, 2.8 Hz, 1H) 7.98 (d, J=2.8 Hz, 1H).

Example 16

N-[(2Z)-3-butyl-1-thia-3-azaspiro[4.5]dec-2-ylidene]-5-chloro-2-methoxybenzamide

Example 16A 1-oxa-spiro[2.5]octane

The title compound was prepared according to the procedure outlined in Example 11A substituting methylene-cyclohexane (Aldrich) for 2,3,3-trimethyl-but-1-ene.

Example 16B

1-Thia-spiro[2.5]octane

The title compound was prepared according to the procedure outlined in Example 15B substituting Example 16A for Example 15A.

Example 16C

3-butyl-1-thia-3-aza-spiro[4.5]dec-2-ylideneamine

The title compound was prepared according to the procedure outlined in Example 2A substituting Example 16B for 2,2-dimethyl-thiirane.

Example 16D

N-[(2Z)-3-butyl-1-thia-3-azaspiro[4.5]dec-2-ylidene]-5-chloro-2-methoxybenzamide The title compound was obtained according to the procedure outlined in Example 2B by substituting Example 16C for Example 2A. MS (DCI/NH$_3$) m/z 395 (M+H)$^+$; $^1$H NMR (500 MHz, CDCl$_3$) δ ppm 0.98 (t, J=7.4 Hz, 3H) 1.40 (m, 2H) 1.65 (m, 10H) 1.95 (m, 2H) 3.41 (s, 2H) 3.67 (t, J=7.4 Hz, 2H) 3.86 (s, 3H) 6.86 (d, J=8.6 Hz, 1H) 7.30 (dd, J=8.6, 2.8 Hz, 1H) 7.96 (d, J=2.8 Hz, 1H).

Example 17 trans-N-[(2Z)-3-butyl-4,5-dimethyl-1,3-thiazolidin-2-ylidene]-5-chloro-2-methoxybenzamide

Example 17A cis-2,3-Dimethyl-thiirane

The title compound was prepared according to the procedure outlined in Example 15B substituting cis-2,3-epoxybutane (Aldrich) for Example 15A.

Example 17B trans-3-butyl-4,5-dimethylthiazolidin-2-imine

The title compound was prepared according to the procedure outlined in Example 2A substituting Example 17A for 2,2-dimethyl-thiirane.

Example 17C trans-N-[(2Z)-3-butyl-4,5-dimethyl-1,3-thiazolidin-2-ylidene]-5-chloro-2-methoxybenzamide The title compound was obtained according to the procedure outlined in Example 2B by substituting Example 17B for Example 2A. MS (DCI/NH$_3$) m/z 355 (M+H)$^+$; $^1$H NMR (500 MHz, CDCl$_3$) δ ppm 0.99 (t, J=7.3 Hz, 3H) 1.32 (d, J=6.4 Hz, 3H) 1.39 (m, 2H) 1.40 (d, J=7.0 Hz, 3H) 1.65 (m, 2H) 3.17 (m, 2H) 3.54 (m, 1H) 3.88 (s, 3H) 4.11 (m, 1H) 6.88 (d, J=8.9 Hz, 1H) 7.32 (dd, J=8.9, 2.75 Hz, 1H) 7.98 (d, J=2.8 Hz, 1H).

Example 18 cis-N-[(2Z)-3-butyl-4,5-dimethyl-1,3-thiazolidin-2-ylidene]-5-chloro-2-methoxybenzamide

Example 18A trans-2,3-Dimethyl-thiirane

The title compound was prepared using the procedure described in Example 15B substituting trans-2,3-epoxybutane (Aldrich) for Example 15A.

Example 18B cis-3-butyl-4,5-dimethyl-thiazolidin-2-imine

The title compound was prepared using the procedure described in Example 2A substituting Example 18A for 2,2-dimethyl-thiirane.

Example 18C cis-N-[(2Z)-3-butyl-4,5-dimethyl-1,3-thiazolidin-2-ylidene]-5-chloro-2-methoxybenzamide The title compound was obtained according to the procedure outlined in Example 2B by substituting Example 18B for Example 2A. MS (DCI/NH$_3$) m/z 355 (M+H)$^+$; $^1$H NMR (500 MHz, CDCl$_3$) δ ppm 0.98 (t, J=7.6 Hz, 3H) 1.22 (d, J=6.4 Hz, 3H) 1.33 (d, J=6.7 Hz, 3H) 1.40 (m, 2H) 1.66 (m, 2H) 3.16 (ddd, J=16.2, 8.2, 5.8 Hz, 1H) 3.71 (m, 1H) 3.87 (m, 1H) 3.87 (s, 3H) 4.13 (m, 1H) 6.87 (d, J=8.9 Hz, 1H) 7.32 (dd, J=8.9, 2.8 Hz, 1H) 7.96 (d, J=2.8 Hz, 1H).

Example 19

N-[(2Z)-3-butyl-5,5-dimethyl-1,3-thiazolidin-2-ylidene]-2,2-dimethyl-4-oxo-3,4-dihydro-2H-pyran-6-carboxamide The title compound was obtained according to the procedure outlined in Example 2B by substituting 6,6-dimethyl-4-oxo-5,6-dihydro-4H-pyran-2-carboxylic acid (Aldrich) for 5-chloro-2-methoxy-benzoic acid. MS (DCI/NH$_3$) m/z 339 (M+H)$^+$; $^1$H NMR (500 MHz, CDCl$_3$) δ ppm 0.97 (t, J=7.3 Hz, 3H) 1.37 (m, 2H) 1.50 (s, 6H) 1.51 (s, 6H) 1.61 (m, 2H) 2.53 (s, 2H) 3.42 (s, 2H) 3.68 (t, J=7.0 Hz, 2H) 6.46 (s, 1H).

Example 20

N-[(2Z)-3-butyl-5,5-dimethyl-1,3-thiazolidin-2-ylidene]-2,2-dimethyltetrahydro-2H-pyran-4-carboxamide The title compound was obtained according to the procedure outlined in Example 2B by substituting 2,2-dimethyl-tetrahydro-pyran-4-carboxylic acid (Princeton) for 5-chloro-2-methoxy-benzoic acid. MS (DCI/NH$_3$) m/z 327 (M+H)$^+$; $^1$H NMR (500 MHz, CDCl$_3$) δ ppm 0.97 (t, J=7.3 Hz, 3H) 1.22 (s, 3H) 1.24 (s, 3H) 1.36 (m, 2H) 1.48 (s, 6H) 1.58 (m, 3H) 1.69 (m, 2H) 1.82 (t, J=16.17 Hz, 2H) 3.35 (s, 2H) 3.63 (t, J=6.7 Hz, 2H) 3.69 (td, J=12.2, 2.4 Hz, 1H) 3.79 (ddd, J=11.9, 5.2, 1.5 Hz, 1H).

Example 21

5-chloro-N-{(2Z)-5,5-dimethyl-3-[(2R)-tetrahydro-furan-2-ylmethyl]-1,3-thiazolidin-2-ylidene}-2-methoxybenzamide

Example 21A (R)-tetrahydro-furan-2-ylmethyl-cyanamide

To a stirred mixture of cyanogen bromide (2.2 g, 20.8 mmol) and anhydrous $Na_2CO_3$ (4.2 g, 39.6 mmol) in dry ether (30 mL) cooled between −20 and −10° C. was added (R)-(tetrahydro-furan-2-yl)-methylamine (Aldrich) (2.0 g, 9.8 mmol) over 10 minutes. Stirring was continued for an additional 1.5 hours at −20 to −10° C. Then the mixture was filtered and concentrated to provide 2.21 g of the title product. MS (DCI/NH$_3$) m/z 127 (M+H)$^+$

Example 21B (R)-5,5-Dimethyl-3-(tetrahydro-furan-2-ylmethyl)-thiazolidin-2-ylideneamine 2,2-Dimethyl-thiirane was treated with Example 21A according to the procedure described in Example 2A to provide the title product.

Example 21C 5-chloro-N-{(2Z)-5,5-dimethyl-3-[(2R)-tetrahydro-furan-2-ylmethyl]-1,3-thiazolidin-2-ylidene}-2-methoxybenzamide Example 21B was treated with 5-chloro-2-methoxy-benzoic acid according to the method of Example 2B to provide the title product as a white solid. MS (DCI/NH$_3$) m/z 383 (M+H)$^+$; $^1$H NMR (500 MHz, CDCl$_3$) δ ppm 1.51 (d, J=3.7 Hz, 6H) 1.56-1.74 (m, 2H) 1.84-1.99 (m, 2H) 1.98-2.10 (m, 1H) 3.52 (d, J=11.1 Hz, 1H) 3.59 (dd, J=14.1, 6.8 Hz, 1H) 3.66 (d, J=11.1 Hz, 1H) 3.77 (dd, J=14.1, 7.7 Hz, 1H) 3.84-3.92 (m, 1H) 3.85-3.88 (m, 3H) 4.01 (dd, J=14.1, 3.4 Hz, 1H) 4.13-4.21 (m, 1H) 6.87 (d, J=8.9 Hz, 1H) 7.32 (dd, J=8.9, 2.8 Hz, 1H) 7.92 (d, J=2.8 Hz, 1H).

Example 22

5-chloro-N-{(2Z)-5,5-dimethyl-3-[(2R)-tetrahydro-furan-2-ylmethyl]-1,3-thiazolidin-2-ylidene}-2-(2,2,2-trifluoroethoxy)benzamide

Example 22A (R,Z)-5-chloro-N-(5,5-dimethyl-3-((tetrahydrofuran-2-yl)methyl)thiazolidin-2-ylidene)-2-fluorobenzamide Example 21B was treated with 5-chloro-2-fluoro-benzoic acid (Aldrich) according to the method of Example 2B to provide the title product as a white solid. MS (DCI/NH$_3$) m/z 371 (M+H)$^+$.

Example 22B 5-chloro-N-{(2Z)-5,5-dimethyl-3-[(2R)-tetrahydro-furan-2-ylmethyl]-1,3-thiazolidin-2-ylidene}-2-(2,2,2-trifluoroethoxy)benzamide A mixture of the product from Example 22A (230 mg, 0.62 mmol) and 2,2,2-trifluoro-ethanol (50 μL, 1.24 mmol) in THF (4 mL) was treated with a 1 M solution of potassium tert-butoxide in THF (1.24 mL, 1.24 mmol). The mixture was stirred at room temperature for 3 hours then poured into water, and extracted with ethyl acetate (2×). The combined organic layers were dried, filtered concentrated, and the residue was purified by flash chromatography (silica gel, eluting with EtOAc/Hexane (1:3)) to provide 189 mg of the title product. MS (DCI/NH$_3$) m/z 451 (M+H)$^+$; $^1$H NMR (400 MHz, DMSO-d$_6$) δ ppm 1.45 (s, 6H) 1.56 (m, 1H) 1.83 (m, 2H) 1.92 (m, 1H) 3.64 (m, 4H) 3.77 (m, 2H) 4.11 (m, 1H) 4.73 (dd, J=17.8, 8.9 Hz, 2H) 7.20 (d, J=8.9 Hz, 1H) 7.50 (dd, J=8.9, 2.8 Hz, 1H) 7.69 (d, J=2.76 Hz, 1H).

Example 23

5-chloro-N-{(2Z)-5,5-dimethyl-3-[(2S)-tetrahydrofuran-2-ylmethyl]-1,3-thiazolidin-2-ylidene}-2-methoxybenzamide

Example 23A (S)-((tetrahydro-furan-2-yl)methyl)-cyanamide

The title compound was prepared using the procedure described in Example 21A substituting (S)-(tetrahydro-furan-2-yl)-methylamine (Aldrich) for (R)-(tetrahydro-furan-2-yl)-methylamine.

Example 23B (S)-5,5-dimethyl-3-(tetrahydro-furan-2-ylmethyl)-thiazolidin-2-ylideneamine 2,2-Dimethyl-thiirane was treated with Example 23A according to the procedure described in Example 2A to provide the title product.

Example 23C 5-chloro-N-{(2Z)-5,5-dimethyl-3-[(2S)-tetrahydrofuran-2-ylmethyl]-1,3-thiazolidin-2-ylidene}-2-methoxybenzamide Example 23B was treated with 5-chloro-2-methoxy-benzoic acid according to the method of Example 2B to provide the title product as a white solid. MS (DCI/NH$_3$) m/z 383 (M+H)$^+$; $^1$H NMR (400 MHz, CDCl$_3$) δ ppm 1.38 (m, 1H) 1.50 (s, 3H) 1.51 (s, 3H) 1.92 (m, 2H) 2.04 (m, 1H) 3.52 (d, J=11.1 Hz, 1H) 3.59 (dd, J=13.8, 6.8 Hz, 1H) 3.65 (d, J=11.1 Hz, 1H) 3.77 (m, 1H) 3.86 (s, 3H) 3.88 (m, 1H) 4.01 (dd, J=14.1, 3.4 Hz, 1H) 4.16 (m, 1H) 6.87 (d, J=8.9 Hz, 1H) 7.32 (dd, J=8.9, 2.8 Hz, 1H) 7.92 (d, J=2.8 Hz, 1H).

Example 24

5-chloro-N-[(2Z)-3-(2,4-difluorobenzyl)-5,5-dimethyl-1,3-thiazolidin-2-ylidene]-2-methoxybenzamide To a solution of Example 1A (70 mg, 0.23 mmol) in dry THF/DMF (2:1) (6 mL) was added sodium hydride (14 mg, 0.35 mmol). The mixture was stirred at room temperature for 10 minutes followed by the dropwise addition of 1-bromomethyl-2,4-difluoro-benzene (Aldrich) (57 mg, 0.28 mmol). The mixture was heated to 65° C. for 12 hours after which the mixture was poured into water, and extracted with ethyl acetate (2×). The combined organic layers were dried over MgSO$_4$, filtered and purified by HPLC on a Waters Symmetry C8 column (40 mm×100 mm, 7 μm particle size) using a gradient of 10% to 100% acetonitrile:ammonium acetate (10 mM) over 15 minutes at a flow rate of 70 mL/minute to provide the title product. MS (DCI/NH$_3$) m/z 425 (M+1)$^+$; $^1$H NMR (500 MHz, DMSO-d$_6$) δ ppm 1.41 (s, 6H) 3.47 (s, 2H) 3.77 (s, 3H) 4.88 (s, 2H) 7.10 (d, J=8.9 Hz, 1H) 7.13 (td, J=8.5, 2.4 Hz, 1H) 7.30 (td, J=10.4, 2.8 Hz, 1H) 7.46 (dd, J=8.9, 3.1 Hz, 1H) 7.50 (dd, J=15.3, 8.5 Hz, 1H) 7.64 (d, J=2.8 Hz, 1H).

Example 25

5-chloro-N-[(2Z)-3-(3-fluorobenzyl)-5,5-dimethyl-1,3-thiazolidin-2-ylidene]-2-methoxybenzamide The title compound was prepared according to the procedure as described in Example 24 substituting 1-bromomethyl-3-fluoro-benzene (Aldrich) for 1-bromomethyl-2,4-difluoro-benzene. MS (DCI/NH$_3$) m/z 407 (M+H)$^+$; $^1$H NMR (500 MHz, CDCl$_3$) δ ppm 1.46 (s, 6H) 3.31 (s, 2H) 3.87 (s, 3H) 4.90 (s, 2H) 6.89 (d, J=8.85 Hz, 1H) 7.02 (td, J=8.5, 2.4 Hz, 1H) 7.06 (d, J=9.5 Hz, 1H) 7.11 (d, J=7.6 Hz, 1H) 7.33 (m, 2H) 7.95 (d, J=2.8 Hz, 1H).

Example 26

5-chloro-N-[(2Z)-5,5-dimethyl-3-(oxetan-2-ylmethyl)-1,3-thiazolidin-2-ylidene]-2-methoxybenzamide To a solution of product from Example 1A (300 mg, 1.0 mmol) in dry THF/DMF (1:1) (20 mL) was added potassium tert-butoxide (95%) (177 mg, 1.5 mmol). The mixture was stirred at room temperature for 10 minutes followed by the dropwise addition of toluene-4-sulfonic acid oxetan-2-ylmethyl ester (290 mg, 1.2 mmol). The mixture was heated to 85° C. for 12 hours after which the mixture was poured into water, and extracted with ethyl acetate (2×). The combined organic layers were dried over MgSO$_4$, filtered and purified by HPLC to provide 96 mg of the title product. MS (DCI/NH$_3$) m/z 369 (M+H)$^+$; $^1$H NMR (500 MHz, CDCl$_3$) δ ppm 1.51 (s, 3H) 1.56 (s, 3H) 2.62 (m, 1H) 2.71 (m, 1H) 3.58 (d, J=11.0 Hz, 1H) 3.69 (d, J=11.0 Hz, 1H) 3.87 (s, 3H) 3.96 (m, 2H) 4.52 (dt, J=9.2, 5.8 Hz, 1H) 4.70 (m, 1H) 5.14 (m, 1H) 6.87 (d, J=8.9 Hz, 1H) 7.32 (dd, J=8.9, 2.8 Hz, 1H) 7.87 (d, J=2.8 Hz, 1H).

Example 27

5-chloro-N-[(2Z)-3-isobutyl-5,5-dimethyl-1,3-thiazolidin-2-ylidene]-2-methoxybenzamide Example 1A was treated with 1-bromo-2-methyl-propane according to the method outlined in Example 24. MS (DCI/NH$_3$) m/z 355 (M+H)$^+$; $^1$H NMR (500 MHz, CDCl$_3$) δ ppm 0.99 (d, J=6.8 Hz, 6H) 1.52 (s, 6H) 1.54 (m, 1H) 2.11 (m, 1H) 3.42 (s, 2H) 3.51 (d, J=7.4 Hz, 1H) 3.87 (s, 3H) 6.87 (d, J=8.9 Hz, 1H) 7.32 (dd, J=8.9, 2.8 Hz, 1H) 7.94 (d, J=2.8 Hz, 1H).

Example 28

5-chloro-N-[(2Z)-3-(cyclobutylmethyl)-5,5-dimethyl-1,3-thiazolidin-2-ylidene]-2-methoxybenzamide Example 1A was treated with 1-bromomethyl-cyclobutane according to the method outlined in Example 24 to provide the title product. MS (DCI/NH$_3$) m/z 383 (M+H)$^{+1}$; $^1$H NMR (500 MHz, CDCl$_3$) δ ppm 1.48 (s, 6H) 1.85 (m, 2H) 1.95 (m, 2H) 2.10 (m, 2H) 2.71 (m, 1H) 3.37 (s, 2H) 3.75 (d, J=7.6 Hz, 2H) 3.87 (s, 3H) 6.88 (d, J=8.9 Hz, 1H) 7.32 (dd, J=8.9, 2.8 Hz, 1H) 7.96 (d, J=2.8 Hz, 1H).

Example 29

N-[(2Z)-3-butyl-5,5-dimethyl-1,3-thiazolidin-2-ylidene]-5-chloro-2-(trifluoromethoxy)benzamide To a solution of Example 2A (150 mg, 0.8 mmol) in THF (10 mL) was added N-(3-dimethylaminopropyl)-N-ethylcarbodiimide hydrochloride (0.19 g, 1.0 mmol), 1-hydroxybenzotriazole (0.14 g, 1.0 mmol), triethylamine (0.45 mL, 3.2 mmol) and Example 6A (240 mg, 1.0 mmol). The mixture was stirred overnight at room temperature and then diluted with ethyl acetate, washed with 1 M aqueous NaHCO$_3$, dried (Na$_2$SO$_4$), filtered and concentrated. The residue was purified by preparative HPLC on a waters Symmetry C8 column (40 mm×100 mm, 7 μm particle size) using a gradient of 10% to 100% acetonitrile:ammonium acetate (10 mM) over 15 minutes at a flow rate of 70 mL/minute to provide the title product. MS (ESI$^+$) m/z 409 (M+H)$^+$; $^1$H NMR (300 MHz, DMSO-d$_6$) δ ppm 0.92 (t, J=7.3 Hz, 3H), 1.22-1.39 (m, 2H), 1.46 (s, 6H), 1.52-1.72 (m, 2H), 3.59 (s, 2H), 3.67 (t, J=7.3 Hz, 2H), 7.45 (d, J=8.8 Hz, 1H), 7.67 (dd, J=8.6, 2.9 Hz, 1H), 7.93 (d, J=2.7 Hz, 1H); Anal. Calculated for C$_{17}$H$_{20}$ClF$_3$N$_2$O$_2$S: C, 49.94; H, 4.93; N, 6.85. Found: C, 50.03; H, 5.03; N, 6.86.

Example 30

4-bromo-N-[(2Z)-3-butyl-5,5-dimethyl-1,3-thiazolidin-2-ylidene]-2-methoxybenzamide Example 2A and 4-bromo-2-methoxybenzoic acid were processed as described for Example 29 to provide the title compound. MS (ESI$^+$) m/z 399 (M+H)$^+$; $^1$H NMR (300 MHz, DMSO-d$_6$) δ ppm 0.91 (t, J=7.3 Hz, 3H), 1.29 (t, 2H), 1.44 (s, 6H), 1.51-1.69 (m, 2H), 3.51 (s, 2H), 3.63 (t, J=7.1 Hz, 2H), 3.79 (s, 3H), 7.16 (dd, J=8.1, 1.7 Hz, 1H), 7.25 (d, J=2.0 Hz, 1H), 7.62 (d, J=8.1 Hz, 1H); Anal. Calculated for C$_{17}$H$_{23}$BrN$_2$O$_2$S: C, 51.13; H, 5.81; N, 7.01. Found: C, 50.73; H, 5.84; N, 7.20.

Example 31

N-[(2Z)-3-butyl-5,5-dimethyl-1,3-thiazolidin-2-ylidene]adamantane-1-carboxamide

To a solution of Example 2A (149 mg, 0.8 mmol) in THF (10 mL) was added triethylamine (0.4 mL) and adamantane-1-carbonyl chloride (0.2 g, 1 mmol). The mixture was heated to reflux overnight and then concentrated under reduced pressure. The residue was diluted with ethyl acetate, washed with 1 M NaHCO$_3$, dried (Na$_2$SO$_4$), filtered and concentrated. The residue was purified by column chromatography (SiO$_2$, 0-100% ethyl acetate:hexanes) to provide 25 mg of the title compound. MS (ESI⁺) m/z 349 (M+H)⁺; ¹H NMR (300 MHz, DMSO-d₆) δ ppm 0.92 (t, J=7.3 Hz, 3H), 1.19-1.36 (m, 2H), 1.39 (s, 6H), 1.51-1.61 (m, 2H), 1.61-1.73 (m, 6H), 1.74-1.81 (m, 6H), 1.89-2.02 (m, 3H), 3.40-3.44 (m, 2H), 3.55-3.64 (m, 2H); Anal. Calculated for $C_{20}H_{32}N_2OS$: C, 68.92; H, 9.25; N, 8.04. Found: C, 68.94; H, 8.73; N, 8.02.

Example 32

N-[(2Z)-3-butyl-5,5-dimethyl-1,3-thiazolidin-2-ylidene]-2-oxatricyclo[3.3.1.1$^{3,7}$]decane-1-carboxamide Example 32A 2-Oxa-tricyclo[3.3.1.1$^{3,7}$]decane-1-carboxylic Acid To a solution of 2-oxa-tricyclo[3.3.1.1$^{3,7}$]decane-1-carboxylic acid methyl ester (Richard, Partch; William, Brewster; Bruce, Stokes, *Croatia Chemical Acta* (1969), 58(4), 661-669) (2.5 g, 12.6 mmol) in methanol/water (1:1, 100 mL) was added aqueous 5 N NaOH solution (3.8 mL, 19 mmol). The mixture was stirred at room temperature for 3 hours and then extracted with methylene chloride to remove unreacted starting material. The aqueous layer was acidified (pH2) with 6 N HCl and then extracted with methylene chloride. This organic extract was dried (Na₂SO₄), filtered and concentrated to provide 1.92 g of the title compound as white crystalline solid. MS (ESI⁺) m/z 183 (M+H)⁺.

Example 32B

N-[(2Z)-3-butyl-5,5-dimethyl-1,3-thiazolidin-2-ylidene]-2-oxatricyclo[3.3.1.1$^{3,7}$]decane-1-carboxamide Example 32A and Example 2A were processed as described for Example 29 to provide the title compound. MS (ESI⁺) m/z 351 (M+H)⁺; ¹H NMR (300 MHz, DMSO-d₆) δ ppm 0.92 (t, J=7.3 Hz, 3H), 1.26 (t, 2H), 1.41 (s, 6H), 1.51-1.66 (m, 4H), 1.74-2.00 (m, 8H), 2.05-2.21 (m, 2H), 3.44 (s, 2H), 3.59 (t, J=7.0 Hz, 2H), 4.04 (t, 1H); Anal. Calculated for $C_{19}H_{30}N_2O_2S$: C, 65.1; H, 8.63; N, 7.99. Found: C, 64.77; H, 8.67; N, 7.82.

Example 33

N-[(2Z)-3-butyl-5,5-dimethyl-1,3-thiazolidin-2-ylidene]-4-chloro-2-methoxybenzamide Example 2A and 4-chloro-2-methoxybenzoic acid were processed as described for Example 29 to obtain the title compound. MS (ESI⁺) m/z 355 (M+H)⁺; ¹H NMR (300 MHz, DMSO-d₆) δ ppm 0.91 (t, J=7.5 Hz, 3H) 1.21-1.37 (m, 2H) 1.40-1.49 (m, 6H) 1.50-1.68 (m, 2H) 3.51 (s, 2H) 3.63 (t, J=7.1 Hz, 2H) 3.79 (s, 3H) 7.02 (dd, J=8.3, 1.9 Hz, 1H) 7.12 (d, J=2.0 Hz, 1H) 7.70 (d, J=8.48 Hz, 1H).

Example 34

N-[(2Z)-3-butyl-5,5-dimethyl-1,3-thiazolidin-2-ylidene]-6-chloroquinoline-8-carboxamide Example 2A and 6-chloro-quinoline-8-carboxylic acid (Weyer et al, *Arzneim. Forsch* 1974, 24, 269) were processed as described for Example 29 to obtain the title compound. MS (ESI⁺) m/z 376 (M+H)⁺; ¹H NMR (300 MHz, DMSO-d₆) δ ppm 0.86 (t, J=7.3 Hz, 3H) 1.19-1.34 (m, 2H) 1.50 (s, 6H) 1.51-1.63 (m, 2H) 3.55-3.58 (m, 2H) 3.61 (t, J=6.0 Hz, 2H) 7.60 (dd, J=8.5, 4.1 Hz, 1H) 7.73 (d, J=2.7 Hz, 1H) 8.15 (d, J=2.4 Hz, 1H) 8.37 (dd, J=8.5, 1.7 Hz, 1H) 8.91 (dd, J=4.2, 1.9 Hz, 1H).

Example 35 trans-N-[(2Z)-3-butylhexahydro-1,3-benzothiazol-2(3H)-ylidene]-5-chloro-2-methoxybenzamide Example 35A 3-butylhexahydrobenzo[d]thiazol-2(3H)-imine The title compound was prepared according to the procedure outlined in Example 2A substituting cyclohexene sulfide (Aldrich) for 2,2-dimethyl-thiirane. MS (ESI⁺) m/z 213 (M+H)⁺.

Example 35B trans-N-[(2Z)-3-butylhexahydro-1,3-benzothiazol-2(3H)-ylidene]-5-chloro-2-methoxybenzamide Example 35A and 5-chloro-2-methoxy-benzoic acid were processed according to the procedure outlined in Example 2B to provide the title product as a white solid. MS (ESI⁺) m/z 381 (M+H)⁺; ¹H NMR (300 MHz, DMSO-d₆) δ ppm 0.96 (t, J=7.3 Hz, 3H) 1.28-1.50 (m, 4H) 1.55-1.69 (m, 4H) 1.84-2.04 (m, 2H) 2.08-2.20 (m, 1H) 2.22-2.33 (m, 1H) 3.02 (dt, J=11.9, 3.4 Hz, 1H) 3.13-3.26 (m, 1H) 3.31-3.44 (m, 1H) 3.87 (s, 3H) 3.91-3.98 (m, 1H) 6.88 (d, J=8.8 Hz, 1H) 7.32 (dd, J=8.8, 2.7 Hz, 1H) 7.97 (d, J=2.7 Hz, 1H).

Example 36

N-[(2Z)-3-butyl-5,5-diethyl-1,3-thiazolidin-2-ylidene]-5-chloro-2-methoxybenzamide Example 36A 2,2-diethyloxirane The title compound was prepared according to the procedure outlined in Example 11A substituting 2-ethyl-1-butene (Aldrich) for 2,3,3-trimethyl-but-1-ene.

Example 36B 2,2-diethylthiirane

The title compound was prepared according to the procedure outlined in Example 15B substituting Example 36A for Example 15A.

Example 36C 3-butyl-5,5-diethylthiazolidin-2-imine

The title compound was prepared using the procedure described in Example 2A substituting Example 36B for 2,2-dimethyl-thiirane. MS (ESI⁺) m/z 215 (M+H)⁺.

Example 36D

N-[(2Z)-3-butyl-5,5-diethyl-1,3-thiazolidin-2-ylidene]-5-chloro-2-methoxybenzamide Example 36C and 5-chloro-2-methoxy-benzoic acid were processed according to the procedure outlined in Example 2B to provide the title product as a white solid. MS (ESI$^+$) m/z 383 (M+H)$^+$; $^1$H NMR (300 MHz, DMSO-d$_6$) δ ppm 0.91 (t, J=7.3 Hz, 9H) 1.21-1.38 (m, 2H) 1.51-1.67 (m, 2H) 1.73 (q, J=7.2 Hz, 4H) 3.53 (s, 2H) 3.61 (t, J=7.3 Hz, 2H) 3.77 (s. 3H) 7.09 (d, J=9.2 Hz, 1H) 7.44 (dd, J=8.8, 2.7 Hz, 1H) 7.64 (d, J=2.771 Hz, 1H).

Example 37

N-[(2Z)-3-butyl-5-isopropyl-1,3-thiazolidin-2-ylidene]-5-chloro-2-methoxybenzamide

Example 37A 2-isopropylthiirane

The title compound was prepared using the procedure described in Example 15B substituting 1,2-epoxy-3-methylbutane (Aldrich) for Example 15A.

Example 37B 3-butyl-5-isopropylthiazolidin-2-imine

The title compound was prepared using the procedure described in Example 2A substituting Example 37A for 2,2-dimethyl-thiirane. MS (ESI$^+$) m/z 201 (M+H)$^+$.

Example 37C

N-[(2Z)-3-butyl-5-isopropyl-1,3-thiazolidin-2-ylidene]-5-chloro-2-methoxybenzamide Example 37B and 5-chloro-2-methoxy-benzoic acid were processed according to the procedure outlined in Example 2B to provide the title product as a white solid. MS (ESI$^+$) m/z 369 (M+H)$^+$; $^1$H NMR (300 MHz, DMSO-d$_6$) δ ppm 0.93 (t, J=7.3 Hz, 3H) 0.93 (d, J=4.4 Hz, 3H) 0.95 (d, J=4.4 Hz, 3H) 1.21-1.37 (m, 2H) 1.53-1.65 (m, 2H) 1.78-1.91 (m, 1H) 3.47-3.57 (m, 2H) 3.61 (t, J=7.3 Hz, 2H) 3.75 (s, 3H) 3.78-3.88 (m, 1H) 7.09 (d, J=8.8 Hz, 1H) 7.44 (dd, J=8.8, 3.1 Hz, 1H) 7.64 (d, J=2.7 Hz, 1H).

Example 38

N-[(2Z)-3-butyl-5-ethyl-1,3-thiazolidin-2-ylidene]-5-chloro-2-methoxybenzamide

Example 38A 2-ethylthiirane

The title compound was prepared according to the procedure described in Example 15B substituting 1,2-epoxy-butane (Aldrich) for Example 15A.

Example 38B 3-butyl-5-ethylthiazolidin-2-imine

The title compound was prepared according the procedure described in Example 2A substituting Example 38A for 2,2-dimethyl-thiirane. MS (ESI$^+$) m/z 187 (M+H)$^+$.

Example 38C

N-[(2Z)-3-butyl-5-ethyl-1,3-thiazolidin-2-ylidene]-5-chloro-2-methoxybenzamide

Example 38B and 5-chloro-2-methoxy-benzoic acid were processed according to the procedure outlined in Example 2B to provide the title product as a white solid. MS (ESI$^+$) m/z 355 (M+H)$^+$; $^1$H NMR (300 MHz, DMSO-d$_6$) δ ppm 0.97 (t, J=7.3 Hz, 3H) 1.02 (t, J=7.5 Hz, 3H) 1.30-1.47 (m, 2H) 1.63 (dd, J=7.1 Hz, 2H) 1.68-1.81 (m, 2H) 3.27-3.40 (m, J=10.5 Hz, 1H) 3.40-3.52 (m, 1H) 3.60-3.80 (m, 3H) 3.88 (s, 3H) 6.88 (d, J=9.2 Hz, 1H) 7.32 (dd, J=8.8, 2.7 Hz, 1H) 7.99 (d, J=2.7 Hz, 1H).

Example 39

5-chloro-N-[(2Z)-5,5-dimethyl-3-neopentyl-1,3-thiazolidin-2-ylidene]-2-methoxybenzamide

Example 39A

N-neopentlcyanamide

The title compound was prepared according to the procedure described in Example 21A substituting neopentylamine (TCI) for (R)-(tetrahydro-furan-2-yl)-methylamine.

Example 39B 5,5-dimethyl-3-neopentylthiazolidin-2-imine

The title compound was prepared according to the procedure described in Example 2A substituting Example 39A for N-butyl-cyanamide. MS (ESI$^+$) m/z 201 (M+H)$^+$.

Example 39C 5-chloro-N-[(2Z)-5,5-dimethyl-3-neopentyl-1,3-thiazolidin-2-ylidene]-2-methoxybenzamide Example 39B and 5-chloro-2-methoxy-benzoic acid were processed according to the procedure outlined in Example 2B to provide the title product as a white solid. MS (ESI$^+$) m/z 369 (M+H)$^+$; $^1$H NMR (300 MHz, DMSO-d$_6$) δ ppm 1.05 (s, 9H) 1.53 (s, 6H) 3.49 (s, 4H) 3.86 (s, 3H) 6.87 (d, J=8.8 Hz, 1H) 7.32 (dd, J=8.8, 2.7 Hz, 1H) 7.97 (d, J=2.7 Hz, 1H).

Example 40

N-[(2Z)-3-butyl-5,5-diethyl-1,3-thiazolidin-2-ylidene]-5-chloro-2-methoxybenzamide

Example 40A 2,2-diethyl-thiirane

The title compound was prepared using the procedure as described in Example 3A substituting 2,2-diethyloxirane for 2-tert-butyl-oxirane. MS (DCI/NH$_3$) m/z 115 (M+H)$^+$

Example 40B 3-butyl-5,5-diethyl-thiazolidin-2-imine

The title compound was prepared using the procedure described in Example 2A substituting Example 40A for 2,2-dimethyl-thiirane. MS (ESI$^{30}$) m/z 215 (M+H)$^+$;

Example 40C

N-[(2Z)-3-butyl-5,5-diethyl-1,3-thiazolidin-2-ylidene]-5-chloro-2-methoxybenzamide The title compound was obtained according to the procedure outlined in Example 2B by substituting Example 40B for Example 2A. MS (ESI$^+$) m/z 383 (M+H)$^+$; $^1$H NMR (300 MHz, DMSO-D$_6$) δ ppm 0.87-0.97 (m, 9H), 1.22-1.38 (m, 2H), 1.51-1.66 (m, 2H), 1.73 (q, J=7.2 Hz, 4H), 3.53 (s, 2H), 3.61 (t, J=7.3 Hz, 2H), 3.77 (s, 3H), 7.09 (d, J=9.2 Hz, 1H), 7.44 (dd, J=8.8, 2.7 Hz, 1H), 7.64 (d, J=2.7 Hz, 1H).

Example 41

5-chloro-N-[(2Z)-5,5-dimethyl-3-propyl-1,3-thiazolidin-2-ylidene]-2-methoxybenzamide A 20 mL scintillation vial was charged with polymer bound 2-tert-butylimino-2-diethylamino-1,3-dimethyl-perhydro-1,3,2-diazaphosphorine (PS-BEMP resin) (157 mg, 0.35 mmol.). To the resin was then added Example 1A (88 mg, 0.29 mmol) dissolved in DMA (1.0 mL). To the resin-suspension was then added 1-bromopropane (43 mg, 0.35 mmol) dissolved in DMA (0.9 mL). The vial was capped and heated at 70° C. overnight on a heater-shaker. The vial was removed from the heater-shaker and the resin-suspension was filtered out. The reaction mixture was checked by LC/MS and concentrated to dryness. The residue was dissolved in 1:1 DMSO/MeOH and purified by reverse phase HPLC eluting with a gradient of acetonitrile and 10 mM ammonium acetate in water. Fractions selected by mass spectrometry were concentrated to dryness to provide the title compound to provide the title compound. $^1$H NMR (500 MHz, DMSO-D$_6$/D$_2$O) δ ppm 0.89 (t, 3H) 1.45-1.48 (m, 6H) 1.58-1.68 (m, 2H) 3.52-3.54 (m, 2H) 3.60 (t, 2H) 3.77-3.77 (m, 3H) 7.10 (d, 1H) 7.45 (dd, 1H) 7.62 (d, 1H); MS (ESI) 341 (M+H)$^+$.

Example 42

5-chloro-N-[(2Z)-3-(2-fluorobenzyl)-5,5-dimethyl-1,3-thiazolidin-2-ylidene]-2-methoxybenzamide A 20 mL scintillation vial was charged with PS-BEMP resin (157 mg, 0.35 mmol.). To the resin was then added Example 1A (88 mg, 0.29 mmol) dissolved in DMA (1.0 mL). To the resin-suspension was then added 1-(bromomethyl)-2-fluorobenzene (66 mg, 0.35 mmol) dissolved in DMA (0.9 mL). The vial was capped and heated at 70° C. overnight on a heater-shaker. The vial was removed from the heater-shaker and the resin-suspension was filtered out. The reaction mixture was checked by LC/MS and concentrated to dryness. The residue was dissolved in 1:1 DMSO/MeOH and purified by reverse phase HPLC using a method analogous to that described in Example 41 to provide the title compound. $^1$H NMR (500 MHz, DMSO-D$_6$/D$_2$O) δ ppm 1.39-1.45 (m, 6H) 3.49-3.52 (m, 2H) 3.77-3.79 (m, 3H) 4.88-4.91 (m, 2H) 7.11 (d, 1H) 7.21-7.28 (m, 2H) 7.38-7.50 (m, 3H) 7.65 (d, 1H); MS (ESI) 407 (M+H)$^+$.

Example 43

5-chloro-N-[(2Z)-3-(2,6-difluorobenzyl)-5,5-dimethyl-1,3-thiazolidin-2-ylidene]-2-methoxybenzamide A 20 mL scintillation vial was charged with PS-BEMP resin (157 mg, 0.35 mmol.). To the resin was then added Example 1A (88 mg, 0.29 mmol) dissolved in DMA (1.0 mL). To the resin-suspension was then added 2-(bromomethyl)-1,3-difluorobenzene (72 mg, 0.35 mmol) dissolved in DMA (0.9 mL). The vial was capped and heated at 70° C. overnight on a heater-shaker. The vial was removed from the heater-shaker and the resin-suspension was filtered out. The reaction mixture was checked by LC/MS and concentrated to dryness. The residue was dissolved in 1:1 DMSO/MeOH and purified by reverse phase HPLC using a method analogous to that described in Example 41 to provide the title compound. $^1$H NMR (500 MHz, DMSO-D$_6$/D$_2$O) δ ppm 1.38-1.43 (m, 6H) 3.50-3.53 (m, 2H) 3.76-3.78 (m, 3H) 4.88-4.93 (m, 2H) 7.08-7.18 (m, 3H) 7.43-7.51 (m, 2H) 7.69 (d, 1H); MS (ESI) 425 (M+H)$^+$.

Example 44

5-chloro-N-[(2Z)-3-(4-fluorobenzyl)-5,5-dimethyl-1,3-thiazolidin-2-ylidene]-2-methoxybenzamide A 20 mL scintillation vial was charged with PS-BEMP resin (157 mg, 0.35 mmol.). To the resin was then added Example 1A (88 mg, 0.29 mmol) dissolved in DMA (1.0 mL). To the resin-suspension was then added 1-(bromomethyl)-4-fluorobenzene (66 mg, 0.35 mmol) dissolved in DMA (0.9 mL). The vial was capped and heated at 70° C. overnight on a heater-shaker. The vial was removed from the heater-shaker and the resin-suspension was filtered out. The reaction mixture was checked by LC/MS and concentrated to dryness. The residue was dissolved in 1:1 DMSO/MeOH and purified by reverse phase HPLC using a method analogous to that described in Example 41 to provide the title compound. $^1$H NMR (500 MHz, DMSO-D$_6$/D$_2$O) δ ppm 1.38-1.44 (m, 6H) 3.44-3.48 (m, 2H) 3.78-3.81 (m, 3H) 4.81-4.85 (m, 2H) 7.11 (d, 1H) 7.19-7.25 (m, 2H) 7.39-7.50 (m, 3H) 7.63 (d, 1H); MS (ESI) 407 (M+H)$^+$.

Example 45

5-chloro-N-[(2Z)-5,5-dimethyl-3-pentyl-1,3-thiazolidin-2-ylidene]-2-methoxybenzamide A 20 mL scintillation vial was charged with PS-BEMP resin (157 mg, 0.35 mmol.). To the resin was then added Example 1A (88 mg, 0.29 mmol) dissolved in DMA (1.0 mL). To the resin-suspension was then added 1-chloropentane (37 mg, 0.35 mmol) dissolved in DMA (0.9 mL). The vial was capped and heated at 70° C. overnight on a heater-shaker. The vial was removed from the heater-shaker and the resin-suspension was filtered out. The reaction mixture was checked by LC/MS and concentrated to dryness. The residue was dissolved in 1:1 DMSO/MeOH and purified by reverse phase HPLC using a method analogous to that described in Example 41 to provide the title compound. $^1$H NMR (500 MHz, DMSO-D$_6$/D$_2$O) δ ppm 0.87 (t, 3H) 1.22-1.38 (m, 4H) 1.42-1.49 (m, 6H) 1.57-1.67 (m, 2H) 3.52-3.54 (m, 2H) 3.59-3.65 (m, 2H) 3.76-3.78 (m, 3H) 7.11 (d, 1H) 7.44-7.48 (m, 1H) 7.66 (d, 1H); MS (ESI), 369 (M+H)$^+$.

Example 46

5-chloro-N-[(2Z)-3-(3,4-difluorobenzyl)-5,5-dimethyl-1,3-thiazolidin-2-ylidene]-2-methoxybenzamide A 20 mL scintillation vial was charged with PS-BEMP resin (157 mg, 0.35 mmol.). To the resin was then added Example 1A (88 mg, 0.29 mmol) dissolved in DMA (1.0 mL). To the resin-suspension was then added 4-(bromomethyl)-1,2-difluorobenzene (43 mg, 0.35 mmol) dissolved in DMA (0.9 mL). The vial was capped and heated at 70° C. overnight on a heater-shaker. The vial was removed from the heater-shaker and the resin-suspension was filtered out. The reaction mixture was checked by LC/MS and concentrated to dryness. The residue was dissolved in 1:1 DMSO/MeOH and purified by reverse phase HPLC using a method analogous to that described in Example 41 to provide the title compound. $^1$H NMR (500 MHz, DMSO-D$_6$/D$_2$O) δ ppm 1.39-1.45 (m, 6H) 3.48-3.51 (m, 2H) 3.77-3.80 (m, 3H) 4.79-4.85 (m, 2H) 7.12 (d, 1H) 7.19-7.25 (m, 1H) 7.39-7.50 (m, 3H) 7.59 (d, 1H); MS (ESI) 425 (M+H)$^+$.

Example 47

5-chloro-N-[(2Z)-3-(2,5-difluorobenzyl)-5,5-dimethyl-1,3-thiazolidin-2-ylidene]-2-methoxybenzamide A 20 mL scintillation vial was charged with PS-BEMP resin (157 mg, 0.35 mmol.). To the resin was then added Example 1A (88 mg, 0.29 mmol) dissolved in DMA (1.0 mL). To the resin-suspension was then added 2-(bromomethyl)-1,4-difluorobenzene (72 mg, 0.35 mmol) dissolved in DMA (0.9 mL). The vial was capped and heated at 70° C. overnight on a heater-shaker. The vial was removed from the heater-shaker and the resin-suspension was filtered out. The reaction mixture was checked by LC/MS and concentrated to dryness. The residue was dissolved in 1:1 DMSO/MeOH and purified by reverse phase HPLC using a method analogous to that described in Example 41 to provide the title compound. $^1$H NMR (500 MHz, DMSO-D$_6$/D$_2$O) δ ppm 1.38-1.48 (m, 6H) 3.52-3.56 (m, 2H) 3.77-3.80 (m, 3H) 4.83-4.90 (m, 2H) 7.12 (d, 1H) 7.20-7.35 (m, 3H) 7.47 (dd, 1H) 7.62 (d, 1H); MS (ESI), 425 (M+H)$^+$.

Example 48

5-chloro-N-[(2Z)-3-(3,5-difluorobenzyl)-5,5-dimethyl-1,3-thiazolidin-2-ylidene]-2-methoxybenzamide A 20 mL scintillation vial was charged with PS-BEMP resin (157 mg, 0.35 mmol.). To the resin was then added Example 1A (88 mg, 0.29 mmol) dissolved in DMA (1.0 mL). To the resin-suspension was then added 1-(bromomethyl)-3,5-difluorobenzene (72 mg, 0.35 mmol) dissolved in DMA (0.9 mL). The vial was capped and heated at 70° C. overnight on a heater-shaker. The vial was removed from the heater-shaker and the resin-suspension was filtered out. The reaction mixture was checked by LC/MS and concentrated to dryness. The residue was dissolved in 1:1 DMSO/MeOH and purified by reverse phase HPLC using a method analogous to that described in Example 41 to provide the title compound. $^1$H NMR (500 MHz, DMSO-D$_6$/D$_2$O) δ ppm 1.40-1.48 (m, 6H) 3.51-3.56 (m, 2H) 3.77-3.81 (m, 3H) 4.82-4.87 (m, 2H) 7.07-7.13 (m, 3H) 7.14-7.21 (m, 1H) 7.46 (dd, 1H) 7.59 (d, 1H); MS (ESI) 425 (M+H)$^+$.

Example 49

5-chloro-N-[(2Z)-5,5-dimethyl-3-(3-methylbutyl)-1,3-thiazolidin-2-ylidene]-2-methoxybenzamide A 20 mL scintillation vial was charged with PS-BEMP resin (157 mg, 0.35 mmol.). To the resin was then added Example 1A (88 mg, 0.29 mmol) dissolved in DMA (1.0 mL). To the resin-suspension was then added 1-chloro-3-methylbutane (37 mg, 0.35 mmol) dissolved in DMA (0.9 mL). The vial was capped and heated at 70° C. overnight on a heater-shaker. The vial was removed from the heater-shaker and the resin-suspension was filtered out. The reaction mixture was checked by LC/MS and concentrated to dryness. The residue was dissolved in 1:1 DMSO/MeOH and purified by reverse phase HPLC using a method analogous to that described in Example 41 to provide the title compound. $^1$H NMR (500 MHz, DMSO-D$_6$/D$_2$O) δ ppm 0.94 (d, 6H) 1.45 (d, 6H) 1.47-1.53 (m, 2H) 1.53-1.61 (m, 1H) 3.51-3.54 (m, 2H) 3.65 (t, 2H) 3.76-3.81 (m, 3H) 7.09 (d, 1H) 7.45 (dd, 1H) 7.71 (d, 1H); MS (ESI) 369 (M+H)$^+$.

Example 50

5-chloro-N-[(2Z)-3-(2,3-difluorobenzyl)-5,5-dimethyl-1,3-thiazolidin-2-ylidene]-2-methoxybenzamide A 20 mL scintillation vial was charged with PS-BEMP resin (157 mg, 0.35 mmol.). To the resin was then added Example 1A (88 mg, 0.29 mmol) dissolved in DMA (1.0 mL). To the resin-suspension was then added 1-(bromomethyl)-2,3-difluorobenzene (72 mg, 0.35 mmol) dissolved in DMA (0.9 mL). The vial was capped and heated at 70° C. overnight on a heater-shaker. The vial was removed from the heater-shaker and the resin-suspension was filtered out. The reaction mixture was checked by LC/MS and concentrated to dryness. The residue was dissolved in 1:1 DMSO/MeOH and purified by reverse phase HPLC using a method analogous to that described in Example 41 to provide the title compound. $^1$H NMR (500 MHz, DMSO-D$_6$/D$_2$O) δ ppm 1.40-1.47 (m, 6H) 3.52-3.56 (m, 2H) 3.76-3.80 (m, 3H) 4.87-4.97 (m, 2H) 7.10 (d, 1H) 7.18-7.28 (m, 2H) 7.35-7.43 (m, 1H) 7.47 (dd, 1H) 7.62 (d, 1H); MS (ESI) 425 (M+H)$^+$.

Example 51

5-chloro-N-[(2Z)-5,5-dimethyl-3-(4,4,4-trifluorobutyl)-1,3-thiazolidin-2-ylidene]-2-methoxybenzamide A 20 mL scintillation vial was charged with PS-BEMP resin (157 mg, 0.35 mmol.). To the resin was then added Example 1A (88 mg, 0.29 mmol) dissolved in DMA (1.0 mL). To the resin-suspension was then added 4-bromo-1,1,1-trifluorobutane (67 mg, 0.35 mmol) dissolved in DMA (0.9 mL). The vial was capped and heated at 70° C. overnight on a heater-shaker. The vial was removed from the heater-shaker and the resin-suspension was filtered out. The reaction mixture was checked by LC/MS and concentrated to dryness. The residue was dissolved in 1:1 DMSO/MeOH and purified by reverse phase HPLC using a method analogous to that described in Example 41 to provide the title compound. $^1$H NMR (500 MHz, DMSO-D$_6$/D$_2$O) δ ppm 1.39-1.53 (m, 6H)

1.82-1.95 (m, 2H) 2.18-2.37 (m, 2H) 3.55-3.58 (m, 2H) 3.69 (t, 2H) 3.77-3.79 (m, 3H) 7.11 (d, 1H) 7.46 (dd, 1H) 7.64 (d, 1H); MS (ESI) 409 (M+H)$^+$.

Example 52

N-[(2Z)-3-butyl-5,5-dimethyl-1,3-thiazolidin-2-ylidene]-1-benzofuran-5-carboxamide The title compound was prepared using the procedure as described in Example 2B by substituting benzofuran-5-carboxylic acid for 5-chloro-2-methoxy-benzoic acid. $^1$H NMR (400 MHz, CDCl$_3$) δ ppm 1.01 (t, J=7.36 Hz, 3H) 1.40-1.51 (m, 2H) 1.53 (s, 6H) 1.70 (dt, J=14.42, 7.36 Hz, 2H) 3.41-3.45 (m, 2H) 3.81 (t, J=7.06 Hz, 2H) 6.84 (d, J=2.15 Hz, 1H) 7.50 (d, J=8.59 Hz, 1H) 7.64 (d, J=2.15 Hz, 1H) 8.28 (dd, J=8.59, 1.23 Hz, 1H) 8.56 (s, 1H); MS (DCI/NH$_3$) m/z 331 (M+H)$^+$.

Example 53

N-[(2Z)-3-butyl-1-thia-3-azaspiro[4.4]non-2-ylidene]-1-benzofuran-5-carboxamide The title compound was obtained according to the procedure outlined in Example 2B by substituting Example 15C for Example 2A and benzofuran-5-carboxylic acid for 5-chloro-2-methoxy-benzoic acid. $^1$H NMR (400 MHz, CDCl$_3$) δ ppm 1.01 (t, J=7.36 Hz, 3H) 1.38-1.50 (m, 2H) 1.65-1.78 (m, 4H) 1.80-1.94 (m, 4H) 2.02-2.13 (m, 2H) 3.55 (s, 2H) 3.81 (t, J=7.06 Hz, 2H) 6.84 (d, J=2.15 Hz, 1H) 7.50 (d, J=8.29 Hz, 1H) 7.64 (d, J=2.15 Hz, 1H) 8.28 (dd, J=8.59, 1.53 Hz, 1H) 8.57 (d, J=1.53 Hz, 1H); MS (DCI/NH$_3$) m/z 357 (M+H)$^+$.

Example 54

N-[(2Z)-3-butyl-1-thia-3-azaspiro[4.4]non-2-ylidene]-2-methyl-1-benzofuran-5-carboxamide The title compound was obtained according to the procedure outlined in Example 2B by substituting Example 15C for Example 2A and 2-methylbenzofuran-5-carboxylic acid for 5-chloro-2-methoxy-benzoic acid. $^1$H NMR (400 MHz, CDCl$_3$) δ ppm 1.00 (t, J=7.36 Hz, 3H) 1.38-1.50 (m, 2H) 1.65-1.77 (m, 4H) 1.78-1.93 (m, 4H) 2.03-2.13 (m, 2H) 2.46 (s, 3H) 3.54 (s, 2H) 3.80 (t, J=7.06 Hz, 2H) 6.43 (s, 1H) 7.39 (d, J=8.59 Hz, 1H) 8.20 (dd, J=8.59, 1.53 Hz, 1H) 8.42 (d, J=1.23 Hz, 1H); MS (DCI/NH$_3$) m/z 371 (M+H)$^+$.

Example 55

2,2-dimethyl-4-oxo-N-{(2Z)-3-[(2S)-tetrahydrofuran-2-ylmethyl]-1-thia-3-azaspiro[4.5]dec-2-ylidene}-3,4-dihydro-2H-pyran-6-carboxamide

Example 55A

(S)-3-((tetrahydrofuran-2-yl)methyl)-1-thia-3-azaspiro[4.5]decan-2-imine

Example 16B was treated with Example 23A according to the procedure described in Example 2A to provide the title product. MS (DCI/NH$_3$) m/z 255 (M+H)$^+$.

Example 55B

2,2-dimethyl-4-oxo-N-{(2Z)-3-[(2S)-tetrahydrofuran-2-ylmethyl]-1-thia-3-azaspiro[4.5]dec-2-ylidene}-3,4-dihydro-2H-pyran-6-carboxamide The title compound was obtained according to the procedure outlined in Example 2B by substituting Example 55A for Example 2A and 2,2-dimethyl-4-oxo-3,4-dihydro-2H-pyran-6-carboxylic acid for 5-chloro-2-methoxy-benzoic acid. $^1$H NMR (500 MHz, CDCl$_3$) δ ppm 1.49 (s, 6H) 1.55-1.64 (m, 6H) 1.63-1.73 (m, 2H) 1.84-1.98 (m, 4H) 1.98-2.09 (m, 1H) 2.52 (s, 3H) 3.56 (dd, J=14.04, 7.02 Hz, 1H) 3.64 (dd, J=54.62, 11.29 Hz, 2H) 3.75 (dd, J=13.73, 7.63 Hz, 1H) 3.85 (dd, J=15.26, 8.24 Hz, 1H) 3.93 (dd, J=13.73, 3.05 Hz, 1H) 4.10 (dq, J=7.02, 3.36 Hz, 1H) 6.42 (s, 1H); MS (DCI/NH$_3$) m/z 407 (M+H)$^+$.

Example 56

N-[(2Z)-3-butyl-5,5-dimethyl-1,3-thiazolidin-2-ylidene]-2-methyl-1-benzofuran-5-carboxamide The title compound was obtained according to the procedure outlined in Example 2B by substituting 2-methylbenzofuran-5-carboxylic acid for 5-chloro-2-methoxy-benzoic acid. $^1$H NMR (400 MHz, CDCl$_3$) δ ppm 1.01 (t, J=7.36 Hz, 3H) 1.39-1.50 (m, 2H) 1.53 (s, 6H) 1.65-1.74 (m, 2H) 2.46 (d, J=1.23 Hz, 3H) 3.43 (s, 2H) 3.80 (t, J=7.36 Hz, 2H) 6.43 (t, J=0.92 Hz, 1H) 7.39 (d, J=8.59 Hz, 1H) 8.19 (dd, J=8.59, 1.84 Hz, 1H) 8.42 (d, J=1.84 Hz, 1H); MS (DCI/NH$_3$) m/z 345 (M+H)$^+$.

Example 57

N-{(2Z)-3-[(2S)-tetrahydrofuran-2-ylmethyl]-1-thia-3-azaspiro[4.5]dec-2-ylidene}-1-benzofuran-5-carboxamide The title compound was obtained according to the procedure outlined in Example 2B by substituting Example 55A for Example 2A and benzofuran-5-carboxylic acid for 5-chloro-2-methoxy-benzoic acid. $^1$H NMR (500 MHz, CDCl$_3$) δ ppm 1.56-1.78 (m, 9H) 1.88-2.00 (m, 4H) 2.04-2.12 (m, 1H) 3.63 (dd, J=36.62, 10.98 Hz, 2H) 3.71-3.82 (m, 2H) 3.89 (q, J=8.24, 7.02 Hz, 1H) 4.05 (dd, J=13.73, 3.36 Hz, 1H) 4.18-4.26 (m, 1H) 6.83 (dd, J=2.14, 0.61 Hz, 1H) 7.49 (d, J=8.54 Hz, 1H) 7.64 (d, J=2.14 Hz, 1H) 8.26 (dd, J=8.54, 1.53 Hz, 1H) 8.54 (d, J=1.53 Hz, 1H); MS (DCI/NH$_3$) m/z 399 (M+H)$^+$.

Example 58

2,2-dimethyl-4-oxo-N-{(6Z)-7-[(2R)-tetrahydrofuran-2-ylmethyl]-5-thia-7-azaspiro[3.4]oct-6-ylidene}-3,4-dihydro-2H-pyran-6-carboxamide

Example 58A

1-oxaspiro[2.3]hexane

The title compound was prepared according to the procedure outlined in Example 11A substituting methylenecyclobutane for 2,3,3-trimethyl-but-1-ene.

Example 58B 1-thiaspiro[2.3]hexane

The title compound was prepared according to the procedure outlined in Example 15B substituting Example 58A for Example 15A.

Example 58C (R)-7-((tetrahydrofuran-2-yl)methyl)-5-thia-7-azaspiro[3.4]octan-6-imine Example 58B was treated with Example 21A according to the procedure described in Example 2A to provide the title product. MS (DCI/NH$_3$) m/z 227 (M+H)$^+$.

Example 58D 2,2-dimethyl-4-oxo-N-{(6Z)-7-[(2R)-tetrahydrofuran-2-ylmethyl]-5-thia-7-azaspiro[3.4]oct-6-ylidene}-3,4-dihydro-2H-pyran-6-carboxamide The title compound was obtained according to the procedure outlined in Example 2B by substituting Example 58C for Example 2A and 2,2-dimethyl-4-oxo-3,4-dihydro-2H-pyran-6-carboxylic acid for 5-chloro-2-methoxy-benzoic acid. $^1$H NMR (400 MHz, CDCl$_3$) δ ppm 1.50 (s, 6H) 1.54-1.57 (m, 2H) 1.57-1.66 (m, 1H) 1.85-1.95 (m, 3H) 2.23-2.34 (m, 2H) 2.41-2.50 (m, 2H) 2.51-2.54 (m, 2H) 3.57 (dd, J=14.12, 7.06 Hz, 1H) 3.76 (dd, J=15.04, 6.75 Hz, 1H) 3.83-3.90 (m, 2H) 3.93-3.95 (m, 1H) 3.96-3.99 (m, 1H) 4.06-4.14 (m, 1H) 6.43 (s, 1H); MS (DCI/NH$_3$) m/z 379 (M+H)$^+$.

Example 59

N-{(6Z)-7-[(2R)-tetrahydrofuran-2-ylmethyl]-5-thia-7-azaspiro[3.4]oct-6-ylidene}-1-benzofuran-5-carboxamide The title compound was obtained according to the procedure outlined in Example 2B by substituting Example 58C for Example 2A and benzofuran-5-carboxylic acid for 5-chloro-2-methoxy-benzoic acid. $^1$H NMR (400 MHz, CDCl$_3$) δ ppm 1.67-1.79 (m, 1H) 1.89-2.00 (m, 3H) 2.01-2.12 (m, 2H) 2.25-2.36 (m, 2H) 2.42-2.55 (m, 2H) 3.73-3.82 (m, 2H) 3.90 (dd, J=26.70, 11.05 Hz, 2H) 3.88-3.95 (m, 1H) 4.07 (dd, J=13.81, 3.38 Hz, 1H) 4.18-4.26 (m, 1H) 6.84 (dd, J=2.45, 1.23 Hz, 1H) 7.50 (dt, J=8.59, 0.92 Hz, 1H) 7.65 (d, J=2.45 Hz, 1H) 8.25 (dd, J=8.59, 1.84 Hz, 1H) 8.53 (d, J=1.53 Hz, 1H); MS (DCI/NH$_3$) m/z 371 (M+H)$^+$.

Example 60

5-chloro-2-methoxy-N-{(6Z)-7-[(2R)-tetrahydrofuran-2-ylmethyl]-5-thia-7-azaspiro[3.4]oct-6-ylidene}benzamide The title compound was obtained according to the procedure outlined in Example 2B by substituting Example 58C for Example 2A. $^1$H NMR (400 MHz, CDCl$_3$) δ ppm 1.61-1.73 (m, 1H) 1.86-2.10 (m, 4H) 2.22-2.35 (m, 2H) 2.40-2.54 (m, 2H) 3.62 (dd, J=144.12, 6.75 Hz, 1H) 3.77 (dd, J=133.81, 6.75 Hz, 1H) 3.81-3.94 (m, 4H) 3.87 (s, 3H) 3.99 (dd, J=14.12, 3.38 Hz, 1H) 4.12-4.21 (m, 1H) 6.88 (d, J=8.90 Hz, 1H) 7.32 (dd, J=8.90, 2.76 Hz, 1H) 7.92 (d, J=2.76 Hz, 1H); MS (DCI/NH$_3$) m/z 395 (M+H)$^+$.

Example 61

N-[(6Z)-7-butyl-5-thia-7-azaspiro[3.4]oct-6-ylidene]-5-chloro-2-methoxybenzamide

Example 61A 7-butyl-5-thia-7-azaspiro[3.4]octan-6-imine

The title compound was prepared according to the procedure outlined in Example 2A substituting Example 58B for 2,2-dimethyl-thiirane. MS (DCI/NH$_3$) m/z 199 (M+H)$^+$;

Example 61B

N-[(6Z)-7-butyl-5-thia-7-azaspiro[3.4]oct-6-ylidene]-5-chloro-2-methoxybenzamide The title compound was obtained according to the procedure outlined in Example 2B by substituting Example 61A for Example 2A. $^1$H NMR (500 MHz, CDCl$_3$) δ ppm 0.98 (t, J=7.32 Hz, 3H) 1.33-1.43 (m, 2H) 1.61-1.69 (m, 2H) 1.90-2.07 (m, 2H) 2.22-2.32 (m, 2H) 2.45-2.53 (m, 2H) 3.69 (s, 2H) 3.70-3.74 (m, 2H) 3.87 (s, 3H) 6.88 (d, J=8.85 Hz, 1H) 7.32 (dd, J=8.54, 2.75 Hz, 1H) 7.96 (d, J=2.75 Hz, 1H); MS (DCI/NH$_3$) m/z 367 (M+H)$^+$.

Example 62

4-bromo-N-[(6Z)-7-butyl-5-thia-7-azaspiro[3.4]oct-6-ylidene]-2-methoxybenzamide

The title compound was obtained according to the procedure outlined in Example 2B by substituting Example 61A for Example 2A and 4-bromo-2-methoxybenzoic acid for 5-chloro-2-methoxy-benzoic acid. $^1$H NMR (400 MHz, CDCl$_3$) δ ppm 0.96 (t, J=7.36 Hz, 3H) 1.32-1.44 (m, 2H) 1.59-1.69 (m, 2H) 1.89-2.07 (m, 2H) 2.21-2.32 (m, 2H) 2.49 (dd, J=21.48, 9.21 Hz, 2H) 3.71 (s, 2H) 3.69-3.78 (m, 2H) 3.87-3.92 (s, 3H) 7.07-7.10 (m, 1H) 7.10 (d, J=7.06 Hz, 1H) 7.89 (d, J=8.59 Hz, 1H); MS (DCI/NH$_3$) m/z 411 (M+H)$^+$.

Example 63

4-bromo-2-methoxy-N-{(6Z)-7-[(2R)-tetrahydrofuran-2-ylmethyl]-5-thia-7-azaspiro[3.4]oct-6-ylidene}benzamide The title compound was obtained according to the procedure outlined in Example 2B by substituting Example 58C for Example 2A and 4-bromo-2-methoxybenzoic acid for 5-chloro-2-methoxy-benzoic acid. $^1$H NMR (500 MHz, CDCl$_3$) δ ppm 1.60-1.71 (m, 2H) 1.82-2.07 (m, 5H) 2.20-2.37 (m, 2H) 2.40-2.56 (m, 2H) 3.63 (dd, J=14.04, 6.71 Hz, 1H) 3.76 (dd, J=14.04, 7.32 Hz, 1H) 3.81-3.96 (m, 2H) 3.89 (s, 3H) 3.95-4.05 (m, 1H) 4.09-4.21 (m, 1H) 7.07-7.10 (m, 2H) 7.85 (d, J=8.85 Hz, 1H); MS (DCI/NH$_3$) m/z 441 (M+H)$^+$.

Example 64

5-chloro-N-[(2Z)-5,5-dimethyl-3-(tetrahydrofuran-3-ylmethyl)-1,3-thiazolidin-2-ylidene]-2-methoxybenzamide

Example 64A

3-(tosylmethyl)tetrahydrofuran

To a solution of (tetrahydrofuran-3-yl)methanol (1.0 g, 9.8 mmol) in $CH_2Cl_2$ (5 mL) and triethylamine (1.98 g, 19.6 mmol) was added p-toluenesulfonyl chloride (2.8 g, 14.7 mmol) in portions over 15 minutes. The mixture was stirred at ambient temperature for 12 hours and was quenched with 10 mL of saturated, aqueous $NaHCO_3$. The layers were separated and the aqueous layer was extracted with $CH_2Cl_2$ (2×10 mL) The combined organic extracts were dried over anhydrous $Na_2SO_4$, filtered and concentrated under reduced pressure to afford the title compound. MS ($DCI/NH_3$) m/z 257 $(M+H)^+$.

Example 64B

5-chloro-N-[(2Z)-5,5-dimethyl-3-(tetrahydrofuran-3-ylmethyl)-1,3-thiazolidin-2-ylidene]-2-methoxybenzamide To a solution of Example 1A (200 mg, 0.67 mmol) in dry THF/DMF (2:1) (15 mL) was added potassium tert-butoxide (95%)(118 mg, 1 mmol). The mixture was stirred at room temperature for 10 minutes followed by the dropwise addition of Example 64A (192 mg, 0.8 mmol). The mixture was heated at 85° C. for 12 hours after which the mixture was poured into water, and extracted with ethyl acetate (2×). The combined organic layers were dried over $MgSO_4$, filtered and purified by HPLC on a Waters Symmetry C8 column (40 mm×100 mm, 7 μm particle size) using a gradient of 10% to 100% acetonitrile:ammonium acetate (10 mM) over 15 minutes at a flow rate of 70 mL/minute to provide the title product. $^1H$ NMR (400 MHz, $CDCl_3$) δ ppm 1.52 (s, 6H) 1.70-1.82 (m, 1H) 2.02-2.11 (m, 1H) 2.69-2.81 (m, 1H) 3.43-3.49 (m, 2H) 3.61 (dd, J=8.59, 5.83 Hz, 1H) 3.69 (dd, J=13.81, 7.67 Hz, 1H) 3.76-3.91 (m, 4H) 3.89 (s, 3H) 6.88 (d, J=8.90 Hz, 1H) 7.34 (dd, J=8.90, 2.76 Hz, 1H) 7.93 (d, J=2.76 Hz, 1H); MS ($DCI/NH_3$) m/z 383 $(M+H)^+$.

Example 65

5-chloro-N-[(2Z)-5,5-dimethyl-3-(tetrahydro-2H-pyran-3-ylmethyl)-1,3-thiazolidin-2-ylidene]-2-methoxybenzamide

Example 65A

3-(tosylmethyl)tetrahydro-2H-pyran

The title compound was obtained according to the procedure outlined in Example 64A, substituting (tetrahydro-2H-pyran-3-yl)methanol for (tetrahydrofuran-3-yl)methanol. MS ($DCI/NH_3$) m/z 288 $(M+NH_4)^+$.

Example 65B

5-chloro-N-[(2Z)-5,5-dimethyl-3-(tetrahydro-2H-pyran-3-ylmethyl)-1,3-thiazolidin-2-ylidene]-2-methoxybenzamide The title compound was prepared according to the procedure as described in Example 64B, substituting Example 65A for Example 64A. $^1H$ NMR (400 MHz, $CDCl_3$) δ ppm 1.33-1.46 (m, 1H) 1.53 (s, 6H) 1.56-1.67 (m, 1H) 1.67-1.77 (m, 1H) 1.79-1.89 (m, 1H) 2.06-2.17 (m, 1H) 3.32 (dd, J=11.05, 8.90 Hz, 1H) 3.39-3.47 (m, 2H) 3.44-3.53 (m, 1H) 3.55-3.71 (m, 2H) 3.81-3.89 (m, 2H) 3.89 (s, 3H) 6.88 (d, J=8.59 Hz, 1H) 7.34 (ddd, J=8.90, 2.76, 0.92 Hz, 2H) 7.95 (d, J=2.76 Hz, 1H); MS ($DCI/NH_3$) m/z 397 $(M+H)^+$.

Example 66

5-chloro-N-[(2Z)-5,5-dimethyl-3-(tetrahydro-2H-pyran-2-ylmethyl)-1,3-thiazolidin-2-ylidene]-2-methoxybenzamide The title compound was prepared according to the procedure as described in Example 64B, substituting 2-(bromomethyl)tetrahydro-2H-pyran for Example 64A. $^1H$ NMR (400 MHz, $CDCl_3$) δ ppm 1.25-1.38 (m, 1H) 1.50 (s, 6H) 1.50-1.56 (m, 2H) 1.60-1.71 (m, 2H) 1.83-1.91 (m, 1H) 3.40 (td, J=11.35, 4.30, 3.07 Hz, 1H) 3.45-3.55 (m, 2H) 3.67 (d, J=11.05 Hz, 2H) 3.85-3.89 (s, 3H) 3.95 (td, J=10.74, 2.45 Hz, 2H) 6.88 (d, J=8.90 Hz, 1H) 7.32 (dd, J=8.90, 2.76 Hz, 1H) 7.93 (d, J=3.07 Hz, 1H); MS ($DCI/NH_3$) m/z 397 $(M+H)^+$.

Example 67

5-chloro-N-((2Z)-5,5-dimethyl-3-{[(2R)-5-oxotetrahydrofuran-2-yl]methyl}-1,3-thiazolidin-2-ylidene)-2-methoxybenzamide

Example 67A

(R)-5-(tosylmethyl)dihydrofuran-2(3H)-one

The title compound was obtained according to the procedure outlined in Example 64A, substituting (R)-5-(hydroxymethyl)dihydrofuran-2(3H)-one for (tetrahydrofuran-3-yl)methanol. MS ($DCI/NH_3$) m/z 288 $(M+NH_4)^+$.

Example 67B

5-chloro-N-((2Z)-5,5-dimethyl-3-{[(2R)-5-oxotetrahydrofuran-2-yl]methyl}-1,3-thiazolidin-2-ylidene)-2-methoxybenzamide The title compound was prepared according to the procedure as described in Example 64B, substituting Example 67A for Example 64A. $^1H$ NMR (400 MHz, $CDCl_3$) δ ppm 1.50 (s, 6H) 1.99-2.15 (m, 1H) 2.35-2.46 (m, 1H) 2.55-2.62 (m, 2H) 3.51 (d, J=10.74 Hz, 1H) 3.62-3.73 (m, 2H) 3.87 (s, 3H) 4.20 (dd, J=14.42, 2.45 Hz, 1H) 4.81-4.90 (m, 1H) 6.89 (d, J=8.90 Hz, 1H) 7.34 (dd, J=8.90, 2.76 Hz, 1H) 7.89 (d, J=2.76 Hz, 1H); MS ($DCI/NH_3$) m/z 397 $(M+H)^+$.

Example 68

5-chloro-N-((2Z)-3-{[(4S)-2,2-dimethyl-1,3-dioxolan-4-yl]methyl}-5,5-dimethyl-1,3-thiazolidin-2-ylidene)-2-methoxybenzamide The title compound was prepared according to the procedure as described in Example 64B, substituting (R)-2,2-dimethyl-4-(tosylmethyl)-1,3-dioxolane for Example 64A. $^1H$ NMR (400 MHz, $CDCl_3$) δ ppm 1.34 (s, 3H) 1.45 (s, 3H) 1.52 (s, 6H) 3.59 (dd, J=32.83, 10.43 Hz, 2H) 3.67 (t, J=6.75 Hz, 1H) 3.74 (dd, J=8.29, 6.75 Hz, 1H) 3.87 (s, 3H) 4.04 (dd, J=14.42, 3.07 Hz, 1H) 4.10 (dd, J=8.29, 6.44 Hz, 1H) 4.43

(qd, J=6.44, 3.38 Hz, 1H) 6.88 (d, J=8.90 Hz, 1H) 7.33 (dd, J=8.90, 2.76 Hz, 1H) 7.88 (d, J=2.45 Hz, 1H); MS (DCI/NH$_3$) m/z 413 (M+H)$^+$.

Example 69

N-[(2Z)-3-butyl-4,4-dimethyl-1,3-thiazolidin-2-ylidene]-5-chloro-2-methoxybenzamide Example 69A 2-(butylamino)-2-methylpropan-1-ol A solution of 2-amino-2-methylpropan-1-ol (14 g, 157 mmol) in isopropanol (100 ml) was treated with 1-bromobutane (37 g, 272 mmol). The mixture was refluxed for 12 hrs, treated with 8 ml of concentrated HCl, then distilled to remove volatiles. The remaining residue was basified with 20% of NaOH, and extracted with Et$_2$O (2×). The Et$_2$O layers were combined and distilled to afford 6.1 g (27%) of the title compound (124-126° C. @54-56 Torr). $^1$H NMR (400 MHz, CDCl$_3$) δ ppm 0.92 (t, J=7.36 Hz, 3H) 1.06 (s, 6H) 1.10 (s, 1H) 1.29-1.50 (m, 4H) 2.49 (t, J=6.75 Hz, 2H) 3.28 (s, 2H).

Example 69B

N-(1-chloro-2-methylpropan-2-yl)butan-1-amine hydrochloride

Example 69A (5.9 g, 40.7 mmol) in chloroform (50 ml) was treated with sulfuryl dichloride (9.7 g, 81.4 mmol). The reaction mixture was stirred at rt for 30 min. then refluxed for 2 hrs. Removal of all the solvent afforded the hydrochloride salt of the title compound.

Example 69C 3-butyl-4,4-dimethylthiazolidin-2-imine

A mixture of Example 69B (40.7 mmol) and potassium thiocyanate (3.9 g, 40.7 mmol) in water (30 ml) was heated at 110° C. for 12 hrs after which the mixture was poured into water, basified with NaHCO$_3$ and extracted with ethyl acetate (2×). The combined organic layers were dried over MgSO$_4$, filtered and concentrated to afford the title compound. MS (DCI/NH$_3$) m/z 187 (M+H)$^+$.

Example 69D

N-[(2Z)-3-butyl-4,4-dimethyl-1,3-thiazolidin-2-ylidene]-5-chloro-2-methoxybenzamide The title compound was obtained according to the procedure outlined in Example 2B, substituting Example 69C for Example 2A. $^1$H NMR (500 MHz, CDCl$_3$) δ ppm 1.00 (t, J=7.32 Hz, 3H) 1.38-1.47 (m, 2H) 1.41 (s, 6H) 1.67-1.77 (m, 2H) 2.99 (s, 2H) 3.47 (t, J=7.93 Hz, 2H) 3.88 (s, 3H) 6.88 (d, J=8.85 Hz, 1H) 7.33 (dd, J=8.85, 2.75 Hz, 1H) 8.01 (d, J=3.05 Hz, 1H); MS (DCI/NH$_3$) m/z 355 (M+H)$^+$.

Example 70

4-bromo-N-[(2Z)-3-butyl-4,4-dimethyl-1,3-thiazolidin-2-ylidene]-2-methoxybenzamide The title compound was obtained according to the procedure outlined in Example 2B, substituting Example 69C for Example 2A and substituting 4-bromo-2-methoxybenzoic acid for 5-chloro-2-methoxy-benzoic acid. $^1$H NMR (500 MHz, CDCl$_3$) δ ppm 0.97 (t, J=7.32 Hz, 3H) 1.35-1.45 (m, 2H) 1.42 (s, 6H) 1.65-1.75 (m, 2H) 2.98 (s, 2H) 3.46 (t, J=7.63 Hz, 2H) 3.87-3.91 (s, 3H) 7.09 (s, 1H) 7.10 (dd, J=7.02, 1.83 Hz, 1H) 7.90 (d, J=8.54 Hz, 1H); MS (DCI/NH$_3$) m/z 399 (M+H)$^+$.

Example 71

5-chloro-N-[(2Z)-5,5-dimethyl-3-(1,2,4-oxadiazol-3-ylmethyl)-1,3-thiazolidin-2-ylidene]-2-methoxybenzamide To a solution of Example 1A (100 mg, 0.34 mmol) in dry THF/DMF (2:1) (15 mL) was added potassium t-butoxide (56.3 mg, 0.5 mmol). The mixture was stirred at room temperature for 10 minutes followed by the portion-wise addition of 3-(chloromethyl)-1,2,4-oxadiazole (43.6 mg, 0.37 mmol) and tetrabutylammonium iodide (49.4 mg, 0.14 mmol). The mixture was heated to 95° C. for 12 hours after which the mixture was poured into water, and extracted with ethyl acetate (2×). The combined organic layers were dried over MgSO$_4$, filtered and purified by HPLC on a Waters Symmetry C8 column (40 mm×100 mm, 7 µm particle size) using a gradient of 10% to 100% acetonitrile:ammonium acetate (10 mM) over 15 minutes at a flow rate of 70 mL/minute to provide the 14.6 mg (12%) of title product. $^1$H NMR (500 MHz, CDCl$_3$) δ ppm 1.55 (s, 6H) 3.55 (s, 2H) 3.87 (s, 3H) 5.11 (s, 2H) 6.87 (d, J=8.85 Hz, 1H) 7.33 (dd, J=8.85, 2.75 Hz, 1H) 7.98 (d, J=2.75 Hz, 1H) 8.74 (s, 1H); MS (DCI/NH$_3$) m/z 381 (M+1)$^+$.

Example 72

5-chloro-N-{(2Z)-3-[(5-chlorothien-2-yl)methyl]-5,5-dimethyl-1,3-thiazolidin-2-ylidene}-2-methoxybenzamide The title compound was prepared according to the procedure as described in Example 71, substituting 2-chloro-5-(chloromethyl)thiophene for 3-(chloromethyl)-1,2,4-oxadiazole. $^1$H NMR (400 MHz, CDCl$_3$) δ ppm 1.49 (s, 6H) 3.36 (s, 2H) 3.89 (s, 3H) 4.94 (s, 2H) 6.79 (dd, J=13.50, 3.68 Hz, 2H) 6.90 (d, J=8.90 Hz, 1H) 7.35 (dd, J=8.59, 2.76 Hz, 1H) 8.04 (d, J=2.76 Hz, 1H); MS (DCI/NH$_3$) m/z 429 (M+11).

Example 73

5-chloro-N-[(2Z)-5,5-dimethyl-3-(1,3-thiazol-4-ylmethyl)-1,3-thiazolidin-2-ylidene]-2-methoxybenzamide The title compound was prepared according to the procedure as described in Example 71, substituting 4-(chloromethyl)thiazole hydrochloride for 3-(chloromethyl)-1,2,4-oxadiazole. $^1$H NMR (400 MHz, CDCl$_3$) δ ppm 1.49 (s, 6H) 3.54 (s, 2H) 3.87 (s, 3H) 5.05 (s, 2H) 6.89 (d, J=8.90 Hz, 1H) 7.33 (dd, J=8.59, 2.76 Hz, 1H) 7.38 (d, J=2.15 Hz, 1H) 7.97 (d, J=2.76 Hz, 1H) 8.78 (d, J=1.84 Hz, 1H); MS (DCI/NH$_3$) m/z 396 (M+1)$^+$.

Example 74

5-chloro-N-[(2Z)-5,5-dimethyl-3-(pyridin-4-ylmethyl)-1,3-thiazolidin-2-ylidene]-2-methoxybenzamide The title compound was prepared according to the procedure as described in Example 71, substituting 4-(bromomethyl)pyridine hydrobromide for 3-(chloromethyl)-1,2,4-oxadiazole. $^1$H NMR (400 MHz, CDCl$_3$) δ ppm 1.49 (s, 6H) 3.51 (s, 2H) 3.86 (s, 3H) 5.00 (s, 2H) 6.87 (d, J=8.90 Hz, 1H) 7.23 (dd, J=6.44, 4.91 Hz, 1H) 7.32 (dd, J=8.90, 2.76 Hz, 1H) 7.40 (d, J=7.67 Hz, 1H) 7.69 (td, J=7.98, 1.84 Hz, 1H) 7.92 (d, J=3.07 Hz, 1H) 8.57 (dd, J=4.91, 0.92 Hz, 1H); MS (DCI/NH$_3$) m/z 390 (M+H)$^+$.

Example 75

5-chloro-N-[(2Z)-5,5-dimethyl-3-(pyridin-3-ylmethyl)-1,3-thiazolidin-2-ylidene]-2-methoxybenzamide The title compound was prepared according to the procedure as described in Example 71, substituting 3-(bromomethyl)pyridine hydrobromide for 3-(chloromethyl)-1,2,4-oxadiazole. $^1$H NMR (500 MHz, CDCl$_3$) δ ppm 1.47 (s, 6H) 3.32 (s, 2H) 3.88 (s, 3H) 4.92 (s, 2H) 6.90 (d, J=8.85 Hz, 1H) 7.31 (dd, J=8.24, 4.58 Hz, 1H) 7.34 (dd, J=8.85, 2.75 Hz, 1H) 7.73 (dt, J=7.93, 2.14 Hz, 1H) 7.96 (d, J=2.75 Hz, 1H) 8.59 (dd, J=4.88, 1.53 Hz, 1H) 8.60 (d, J=1.83 Hz, 1H); MS (DCI/NH$_3$) m/z 390 (M+H)$^+$.

Example 76

5-chloro-N-[(2Z)-5,5-dimethyl-3-(pyridin-2-ylmethyl)-1,3-thiazolidin-2-ylidene]-2-methoxybenzamide The title compound was prepared according to the procedure as described in Example 71, substituting 2-(bromomethyl)pyridine hydrobromide for 3-(chloromethyl)-1,2,4-oxadiazole. $^1$H NMR (400 MHz, CDCl$_3$) δ ppm 1.50 (s, 6H) 3.32 (s, 2H) 3.86 (s, 3H) 4.91 (s, 2H) 6.88 (d, J=8.90 Hz, 1H) 7.24 (d, J=5.83 Hz, 1H) 7.24 (dd, J=4.30, 1.53 Hz, 1H) 7.33 (dd, J=8.90, 2.76 Hz, 1H) 7.91 (d, J=2.76 Hz, 1H) 8.62 (d, J=6.14 Hz, 1H) 8.62 (dd, J=4.60, 1.84 Hz, 1H); MS (DCI/NH$_3$) m/z 390 (M+H)$^+$.

Example 77

5-chloro-N-[(2Z)-3-(2-furylmethyl)-5,5-dimethyl-1,3-thiazolidin-2-ylidene]-2-methoxybenzamide

Example 77A furan-2-ylmethyl methanesulfonate

To the solution of furan-2-ylmethanol (500 mg, 5.1 mmol) in CH$_2$Cl$_2$ (10 mL) and triethylamine (1.54 g, 15.3 mmol) at 0° C. was added dropwise methanesulfonyl chloride (695 mg, 6.1 mmol). The mixture was stirred at 0° C. for 15 min and was quenched with 10 mL of water. The layers were separated and the aqueous layer was extracted with CH$_2$Cl$_2$ (1×10 mL). The combined organic extracts were dried over anhydrous Na$_2$SO$_4$, filtered and concentrated under reduced pressure to afford the title compound.

Example 77B 5-chloro-N-[(2Z)-3-(2-furylmethyl)-5,5-dimethyl-1,3-thiazolidin-2-ylidene]-2-methoxybenzamide The title compound was prepared according to the procedure as described in Example 71, substituting Example 77A for 3-(chloromethyl)-1,2,4-oxadiazole. $^1$H NMR (400 MHz, CDCl$_3$) δ ppm 1.48 (s, 6H) 3.38 (s, 2H) 3.88 (s, 3H) 4.89 (s, 2H) 6.34-6.37 (m, 2H) 6.89 (d, J=8.90 Hz, 1H) 7.33 (dd, J=8.90, 2.76 Hz, 1H) 7.39 (dd, J=1.84, 0.92 Hz, 1H) 8.03 (d, J=2.76 Hz, 1H); MS (DCI/NH$_3$) m/z 379 (M+H)$^+$.

Example 78

5-chloro-N-{(2Z)-3-[(5-fluoropyridin-3-yl)methyl]-5,5-dimethyl-1,3-thiazolidin-2-ylidene}-2-methoxybenzamide

Example 78A (5-fluoropyridin-3-yl)methyl methanesulfonate

The title compound was prepared according to the procedure as described in Example 77A, substituting (5-fluoropyridin-3-yl)methanol for furan-2-ylmethanol.

Example 78B 5-chloro-N-{(2Z)-3-[(5-fluoropyridin-3-yl)methyl]-5,5-dimethyl-1,3-thiazolidin-2-ylidene}-2-methoxybenzamide The title compound was prepared according to the procedure as described in Example 71 substituting Example 78A for 3-(chloromethyl)-1,2,4-oxadiazole. $^1$H NMR (400 MHz, CDCl$_3$) δ ppm 1.48 (s, 6H) 3.33 (s, 2H) 3.86-3.90 (s, 3H) 4.93 (s, 2H) 6.90 (d, J=8.90 Hz, 1H) 7.34 (dd, J=8.90, 2.76 Hz, 1H) 7.51 (dt, J=8.90, 2.76, 1.84 Hz, 1H) 7.90 (d, J=2.76 Hz, 1H) 8.42 (brs, 1H) 8.45 (d, J=2.76 Hz, 1H); MS (DCI/NH$_3$) m/z 408 (M+H)$^+$.

Example 79

5-chloro-N-{(2Z)-3-[(2-fluoropyridin-3-yl)methyl]-5,5-dimethyl-1,3-thiazolidin-2-ylidene}-2-methoxybenzamide

Example 79A (2-fluoropyridin-3-yl)methyl methanesulfonate

The title compound was prepared according to the procedure as described in Example 77A substituting (2-fluoropyridin-3-yl)methanol for furan-2-ylmethanol.

Example 79B 5-chloro-N-{(2Z)-3-[(2-fluoropyridin-3-yl)methyl]-5,5-dimethyl-1,3-thiazolidin-2-ylidene}-2-methoxybenzamide The title compound was prepared according to the procedure as described in Example 71 substituting Example 79A for 3-(chloromethyl)-1,2,4-oxadiazole. $^1$H NMR (500 MHz, CHLOROFORM-D) δ ppm 1.49 (s, 6H) 3.47 (s, 2H) 3.88 (s, 3H) 4.90 (s, 2H) 6.90 (d, J=8.85 Hz, 1H) 7.22 (ddd, J=4.88, 1.83 Hz, 1H) 7.35 (dd, J=8.85, 2.75 Hz, 1H) 7.91 (d, J=3.05

Hz, 1H) 7.96 (ddd, J=7.32, 1.83 Hz, 1H) 8.19 (d, J=4.58 Hz, 1H); MS (DCI/NH$_3$) m/z 408 (M+H)$^+$.

Example 80

5-chloro-N-{(2Z)-3-[(6-fluoropyridin-3-yl)methyl]-5,5-dimethyl-1,3-thiazolidin-2-ylidene}-2-methoxy-benzamide

Example 80A (6-fluoropyridin-3-yl)methyl methanesulfonate

The title compound was prepared according to the procedure as described in Example 77A substituting (6-fluoropyridin-3-yl)methanol for furan-2-ylmethanol.

Example 80B 5-chloro-N-{(2Z)-3-[(6-fluoropyridin-3-yl)methyl]-5,5-dimethyl-1,3-thiazolidin-2-ylidene}-2-methoxy-benzamide The title compound was prepared according to the procedure as described in Example 71, substituting Example 80A for 3-(chloromethyl)-1,2,4-oxadiazole. $^1$H NMR (500 MHz, CDCl$_3$) δ ppm 1.47 (s, 6H) 3.32 (s, 2H) 3.89 (s, 3H) 4.91 (s, 2H) 6.90 (d, J=8.85 Hz, 1H) 6.95 (dd, J=8.54, 3.05 Hz, 1H) 7.35 (dd, J=8.85, 2.75 Hz, 1H) 7.87 (td, J=7.93, 2.44 Hz, 1H) 7.94 (d, J=2.75 Hz, 1H) 8.21 (d, J=2.14 Hz, 1H); MS (DCI/NH$_3$) m/z 408 (M+H)$^+$.

Example 81

5-chloro-N-[(2Z)-5,5-dimethyl-3-(2-pyridin-2-yl-ethyl)-1,3-thiazolidin-2-ylidene]-2-methoxybenzamide The title compound was prepared according to the procedure as described in Example 71, substituting 2-(2-bromoethyl)pyridine hydrobromide for 3-(chloromethyl)-1,2,4-oxadiazole. $^1$H NMR (400 MHz, CDCl$_3$) δ ppm 1.38 (s, 6H) 3.22 (t, J=7.06 Hz, 2H) 3.33 (s, 2H) 3.88 (s, 3H) 4.09 (t, J=7.06 Hz, 2H) 6.89 (d, J=8.90 Hz, 1H) 7.14 (dd, J=7.36, 4.91 Hz, 1H) 7.23-7.29 (m, 1H) 7.34 (dd, J=8.90, 3.07 Hz, 1H) 7.62 (td, J=7.67, 1.84 Hz, 1H) 8.00 (d, J=2.76 Hz, 1H) 8.55 (d, J=4.30 Hz, 1H); MS (DCI/NH$_3$) m/z 404 (M+H)$^+$.

Example 82

5-chloro-N-[(2Z)-3-(3-furylmethyl)-5,5-dimethyl-1,3-thiazolidin-2-ylidene]-2-methoxybenzamide

Example 82A furan-3-ylmethyl methanesulfonate

The title compound was prepared according to the procedure as described in Example 77A substituting furan-3-ylmethanol for furan-2-ylmethanol.

Example 82B 5-chloro-N-[(2Z)-3-(3-furylmethyl)-5,5-dimethyl-1,3-thiazolidin-2-ylidene]-2-methoxybenzamide The title compound was prepared according to the procedure as described in Example 71, substituting Example 82A for 3-(chloromethyl)-1,2,4-oxadiazole. $^1$H NMR (400 MHz, CDCl$_3$) δ ppm 1.47 (s, 6H) 3.32 (s, 2H) 3.88 (s, 3H) 4.76 (s, 2H) 6.41 (brs, 1H) 6.89 (d, J=8.90 Hz, 1H) 7.33 (dd, J=8.90, 2.76 Hz, 1H) 7.41 (d, J=1.53 Hz, 1H) 7.45 (brs, 1H) 7.99 (d, J=2.76 Hz, 1H); MS (DCI/NH$_3$) m/z 379 (M+H)$^+$.

Example 83

5-chloro-N-[(2Z)-5,5-dimethyl-3-(thien-3-ylmethyl)-1,3-thiazolidin-2-ylidene]-2-methoxybenzamide

Example 83A thiophen-3-ylmethyl methanesulfonate

The title compound was prepared according to the procedure as described in Example 77A, substituting thiophen-3-ylmethanol for furan-2-ylmethanol.

Example 83B 5-chloro-N-[(2Z)-5,5-dimethyl-3-(thien-3-ylmethyl)-1,3-thiazolidin-2-ylidene]-2-methoxybenzamide The title compound was prepared according to the procedure as described in Example 71, substituting Example 83A for 3-(chloromethyl)-1,2,4-oxadiazole. $^1$H NMR (400 MHz, CDCl$_3$) δ ppm 1.45 (s, 6H) 3.31 (s, 2H) 3.88 (s, 3H) 4.91 (s, 2H) 6.89 (d, J=8.90 Hz, 1H) 7.08 (dd, J=5.22, 1.23 Hz, 1H) 7.23 (d, J=2.76 Hz, 1H) 7.31 (d, J=2.76 Hz, 1H) 7.33 (dd, J=3.99, 2.76 Hz, 1H) 7.99 (d, J=2.76 Hz, 1H); MS (DCI/NH$_3$) m/z 395 (M+H)$^+$.

Example 84

(Z)—N-(5-tert-butyl-3-butyloxazolidin-2-ylidene)-5-chloro-2-methoxybenzamide

Example 84A (Z)—N-(5-tert-butyl-3-butyloxazolidin-2-imine

The title compound was obtained according to the procedure outlined in Example 2A, substituting 2-tert-butyloxirane for 2,2-dimethyl-thiirane.

Example 84B (Z)—N-(5-tert-butyl-3-butyloxazolidin-2-ylidene)-5-chloro-2-methoxybenzamide The title compound was obtained according to the procedure outlined in Example 2B, substituting Example 84B for Example 2A. $^1$H NMR (500 MHz, CDCl$_3$) δ ppm 0.86 (s, 9H) 0.97 (t, J=7.32 Hz, 3H) 1.34-1.43 (m, 2H) 1.56-1.64 (m, 2H) 3.35 (dd, J=9.15, 7.63 Hz, 1H) 3.42 (td, J=7.02, 3.05, 2.44 Hz, 2H) 3.51 (t, J=9.46 Hz, 1H) 3.82 (s, 3H) 4.32 (dd, J=9.15, 7.63 Hz, 1H) 6.82 (d, J=8.85 Hz, 1H) 7.26 (dd, J=8.85, 3.36 Hz, 1H) 7.65 (d, J=2.75 Hz, 1H); MS (DCI/NH$_3$) m/z 367 (M+H)$^+$. Anal. Calculated for $C_{19}H_{27}ClN_2O_3$: C, 62.20; H, 7.42; N, 7.64. Found: C, 62.01; H, 7.58; N, 7.50.

We claim:
1. A compound of formula (I),

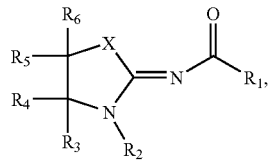

or a pharmaceutically acceptable salt thereof, wherein
X is S;
$R_1$ is
  phenyl substituted with 1, 2, 3, 4, or 5 substituents as represented by N,
$R_j$ at each occurrence is independently alkenyl, alkoxy, alkoxyalkoxy, alkoxyalkoxyalkyl, alkoxyalkyl, alkoxycarbonyl, alkoxycarbonylalkyl, alkyl, alkylcarbonyl, alkylcarbonylalkyl, alkylcarbonyloxy, alkylsulfinyl, alkylsulfinylalkyl, alkyl-S(O)$_2$—, alkyl-S(O)$_2$-alkyl-, cyanoalkyl, formyl, =N—O(alkyl), =N—OH, alkylthio, alkylthioalkyl, alkynyl, carboxy, carboxyalkyl, cyano, halogen, haloalkyl, haloalkoxy, hydroxy, hydroxyalkyl, nitro, $R_hR_k$—N—, $(R_mR_nN)$carbonyl, cycloalkyloxy, cycloalkylalkoxy, or cycloalkyl;
$R_2$ is n-butyl, sec-butyl, iso-butyl, tert-butyl, n-pentyl, isopentyl (3-methylbutyl), neopentyl, n-hexyl, 3-methylhexyl, 2,2-dimethylpentyl, 2,3-dimethylpentyl, n-heptyl, n-octyl, n-nonyl, n-decyl, alkoxy-(C$_2$-C$_6$ alkylene)-, alkoxyalkoxy-(C$_2$-C$_6$ alkylene)-, alkenyl, alkynyl, cycloalkylalkyl, cycloalkyloxyalkyl, cycloalkylalkoxyalkyl, cyanoalkyl, nitroalkyl, haloalkyl, haloalkoxyalkyl, hydroxyalkyl, $R_aR_bN$—(C$_2$-C$_6$ alkylene)-, $R_cS$—(C$_2$-C$_6$ alkylene)-, $R_c$—SO$_2$-alkylene-, $R_c$—C(O)-alkylene-, $R_dC(=N$—OR$_f)$—(C$_2$-C$_6$ alkylene)-, $R_dR_eN$—SO$_2$-alkylene-, or $R_dR_eN$—C(O)-alkylene-;
$R_3$ and $R_4$ are each independently hydrogen, alkyl, cycloalkyl, haloalkyl, or hydroxyalkyl or $R_3$ and $R_4$ taken together with the carbon atom to which they are attached form a monocyclic cycloalkyl;
$R_5$ and $R_6$ are each independently hydrogen, alkyl, aryl, cycloalkyl, haloalkyl, or hydroxyalkyl; or
$R_5$ and $R_6$ taken together with the carbon atom to which they are attached form a monocyclic cycloalkyl ring; or
$R_3$ and $R_5$ taken together with the atoms to which they are attached form a monocyclic cycloalkyl;
$R_a$ and $R_b$, at each occurrence, are each independently hydrogen, alkyl, haloalkyl, alkylcarbonyl, alkylsulfonyl, aryl, arylcarbonyl, arylsulfonyl, or cycloalkyl;
$R_c$, at each occurrence, is independently alkyl, haloalkyl, aryl, or arylalkyl;
$R_d$ and $R_e$, at each occurrence, are each independently hydrogen, alkyl, haloalkyl, aryl, or arylalkyl;
$R_f$ is hydrogen, alkyl, or haloalkyl;
$R_h$ and $R_k$, at each occurrence, are each independently hydrogen, alkyl, haloalkyl, alkylcarbonyl, alkylsulfonyl, aryl, arylcarbonyl, arylsulfonyl, or cycloalkyl; and
$R_m$ and $R_n$, at each occurrence, are each independently hydrogen, alkyl, haloalkyl, aryl, or arylalkyl.

2. The compound of claim 1 or a pharmaceutically acceptable salt thereof, wherein
$R_5$ and $R_6$ are each independently hydrogen, alkyl, or aryl;
$R_3$ and $R_4$ are each independently hydrogen or alkyl; and
$R_2$ is n-butyl, sec-butyl, iso-butyl, or tert-butyl.

3. The compound of claim 1 or a pharmaceutically acceptable salt thereof, wherein
$R_5$ and $R_6$ are each independently hydrogen, alkyl, or aryl;
$R_3$ and $R_4$ are each independently hydrogen or alkyl; and
$R_2$ is alkoxy-(C$_2$-C$_6$ alkylene)-.

4. The compound of claim 1 or a pharmaceutically acceptable salt thereof, wherein
$R_5$ and $R_6$ are each independently hydrogen, alkyl, or aryl;
$R_3$ and $R_4$ are each independently hydrogen or alkyl; and
$R_2$ is cycloalkylalkyl.

5. The compound of claim 1 or a pharmaceutically acceptable salt thereof, wherein
$R_5$ and $R_6$ are each independently hydrogen, alkyl, or aryl;
$R_3$ and $R_4$ are each independently hydrogen or alkyl; and
$R_2$ is n-pentyl, isopentyl (3-methylbutyl), neopentyl, n-hexyl, 3-methylhexyl, 2,2-dimethylpentyl, or 2,3-dimethylpentyl.

6. The compound of claim 1 or a pharmaceutically acceptable salt thereof, selected from the group consisting of
5-chloro-2-methoxy-N-[(2Z)-3-(2-methoxyethyl)-5,5-dimethyl-1,3-thiazolidin-2-ylidene]benzamide;
N-[(2Z)-3-butyl-5,5-dimethyl-1,3-thiazolidin-2-ylidene]-5-chloro-2-methoxybenzamide;
N-[(2Z)-3-butyl-5-tert-butyl-1,3-thiazolidin-2-ylidene]-5-chloro-2-methoxybenzamide;
N-[(2Z)-3-butyl-5-tert-butyl-1,3-thiazolidin-2-ylidene]-4-chloro-2-methoxybenzamide;
4-bromo-N-[(2Z)-3-butyl-5-tert-butyl-1,3-thiazolidin-2-ylidene]-2-methoxybenzamide;
N-[(2Z)-3-butyl-5-tert-butyl-1,3-thiazolidin-2-ylidene]-5-chloro-2-(trifluoromethoxy)benzamide;
N-[(2Z)-3-butyl-5-propyl-1,3-thiazolidin-2-ylidene]-5-chloro-2-methoxybenzamide;
N-[(2Z)-3-butyl-5-ethyl-5-methyl-1,3-thiazolidin-2-ylidene]-5-chloro-2-methoxybenzamide;
N-[(2Z)-3-butyl-5-methyl-1,3-thiazolidin-2-ylidene]-5-chloro-2-methoxybenzamide;
N-[(2Z)-3-butyl-5-(4-fluorophenyl)-1,3-thiazolidin-2-ylidene]-5-chloro-2-methoxybenzamide;
N-[(2Z)-3-butyl-5-tert-butyl-5-methyl-1,3-thiazolidin-2-ylidene]-5-chloro-2-methoxybenzamide;
N-[(2Z)-3-butyl-5-tert-butyl-5-methyl-1,3-thiazolidin-2-ylidene]-4-chloro-2-methoxybenzamide;
4-bromo-N-[(2Z)-3-butyl-5-methyl-1,3-thiazolidin-2-ylidene]-2-methoxybenzamide;
N-[(2Z)-3-butyl-1-thia-3-azaspiro[4.4]non-2-ylidene]-5-chloro-2-methoxybenzamide;
N-[(2Z)-3-butyl-1-thia-3-azaspiro[4.5]dec-2-ylidene]-5-chloro-2-methoxybenzamide;
trans-N-[(2Z)-3-butyl-4,5-dimethyl-1,3-thiazolidin-2-ylidene]-5-chloro-2-methoxybenzamide;
cis-N-[(2Z)-3-butyl-4,5-dimethyl-1,3-thiazolidin-2-ylidene]-5-chloro-2-methoxybenzamide;
5-chloro-N-[(2Z)-3-(2,4-difluorobenzyl)-5,5-dimethyl-1,3-thiazolidin-2-ylidene]-2-methoxybenzamide;
5-chloro-N-[(2Z)-3-(3-fluorobenzyl)-5,5-dimethyl-1,3-thiazolidin-2-ylidene]-2-methoxybenzamide;
5-chloro-N-[(2Z)-3-isobutyl-5,5-dimethyl-1,3-thiazolidin-2-ylidene]-2-methoxybenzamide;
5-chloro-N-[(2Z)-3-(cyclobutylmethyl)-5,5-dimethyl-1,3-thiazolidin-2-ylidene]-2-methoxybenzamide;
N-[(2Z)-3-butyl-5,5-dimethyl-1,3-thiazolidin-2-ylidene]-5-chloro-2-(trifluoromethoxy)benzamide;
4-bromo-N-[(2Z)-3-butyl-5,5-dimethyl-1,3-thiazolidin-2-ylidene]-2-methoxybenzamide;
N-[(2Z)-3-butyl-5,5-dimethyl-1,3-thiazolidin-2-ylidene]-4-chloro-2-methoxybenzamide;

trans-N-[(2Z)-3-butylhexahydro-1,3-benzothiazol-2(3H)-ylidene]-5-chloro-2-methoxybenzamide;
N-[(2Z)-3-butyl-5-methyl-1,3-thiazolidin-2-ylidene]-5-chloro-2-methoxybenzamide
N-[(2Z)-3-butyl-5-isopropyl-1,3-thiazolidin-2-ylidene]-5-chloro-2-methoxybenzamide;
N-[(2Z)-3-butyl-5-ethyl-1,3-thiazolidin-2-ylidene]-5-chloro-2-methoxybenzamide;
5-chloro-N-[(2Z)-5,5-dimethyl-3-neopentyl-1,3-thiazolidin-2-ylidene]-2-methoxybenzamide;
N-[(2Z)-3-butyl-5,5-diethyl-1,3-thiazolidin-2-ylidene]-5-chloro-2-methoxybenzamide;
5-chloro-N-[(2Z)-3-(2-fluorobenzyl)-5,5-dimethyl-1,3-thiazolidin-2-ylidene]-2-methoxybenzamide;
5-chloro-N-[(2Z)-3-(2,6-difluorobenzyl)-5,5-dimethyl-1,3-thiazolidin-2-ylidene]-2-methoxybenzamide;
5-chloro-N-[(2Z)-3-(4-fluorobenzyl)-5,5-dimethyl-1,3-thiazolidin-2-ylidene]-2-methoxybenzamide;
5-chloro-N-[(2Z)-5,5-dimethyl-3-pentyl-1,3-thiazolidin-2-ylidene]-2-methoxybenzamide;
5-chloro-N-[(2Z)-3-(3,4-difluorobenzyl)-5,5-dimethyl-1,3-thiazolidin-2-ylidene]-2-methoxybenzamide;
5-chloro-N-[(2Z)-3-(2,5-difluorobenzyl)-5,5-dimethyl-1,3-thiazolidin-2-ylidene]-2-methoxybenzamide;
5-chloro-N-[(2Z)-3-(3,5-difluorobenzyl)-5,5-dimethyl-1,3-thiazolidin-2-ylidene]-2-methoxybenzamide;
5-chloro-N-[(2Z)-5,5-dimethyl-3-(3-methylbutyl)-1,3-thiazolidin-2-ylidene]-2-methoxybenzamide;
5-chloro-N-[(2Z)-3-(2,3-difluorobenzyl)-5,5-dimethyl-1,3-thiazolidin-2-ylidene]-2-methoxybenzamide;
5-chloro-N-[(2Z)-5,5-dimethyl-3-(4,4,4-trifluorobutyl)-1,3-thiazolidin-2-ylidene]-2-methoxybenzamide;
N-[(6Z)-7-butyl-5-thia-7-azaspiro[3.4]oct-6-ylidene]-5-chloro-2-methoxybenzamide;
4-bromo-N-[(6Z)-7-butyl-5-thia-7-azaspiro[3.4]oct-6-ylidene]-2-methoxybenzamide;
N-[(2Z)-3-butyl-4,4-dimethyl-1,3-thiazolidin-2-ylidene]-5-chloro-2-methoxybenzamide; and
4-bromo-N-[(2Z)-3-butyl-4,4-dimethyl-1,3-thiazolidin-2-ylidene]-2-methoxybenzamide.

7. A pharmaceutical composition comprising a therapeutically effective amount of a compound of formula (I) according to claim 1 or a pharmaceutically acceptable salt thereof, in combination with a pharmaceutically acceptable carrier.

\* \* \* \* \*

UNITED STATES PATENT AND TRADEMARK OFFICE
CERTIFICATE OF CORRECTION

PATENT NO. : 8,158,663 B2  
APPLICATION NO. : 11/954956  
DATED : April 17, 2012  
INVENTOR(S) : Carroll et al.

Page 1 of 1

It is certified that error appears in the above-identified patent and that said Letters Patent is hereby corrected as shown below:

Column 69, line 17, Claim 1: Delete "N," insert -- $R_j$, --

Signed and Sealed this  
Eighteenth Day of December, 2012

David J. Kappos  
*Director of the United States Patent and Trademark Office*